United States Patent
Defossa et al.

(10) Patent No.: US 6,337,344 B1
(45) Date of Patent: Jan. 8, 2002

(54) INDOLE DERIVATIVES AS INHIBITORS OR FACTOR XA

(75) Inventors: Elisabeth Defossa, Idstein; Uwe Heinelt, Wiesbaden; Otmar Klingler, Rodgau; Gerhard Zoller, Schöneck, all of (DE); Fahad A. Al-Obeidi; Armin Walser, both of Tucson, AR (US); Peter Wildgoose, Oberursel; Hans Matter, Langenselbold, both of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/582,344

(22) PCT Filed: Dec. 10, 1998

(86) PCT No.: PCT/EP98/08030

§ 371 Date: Aug. 14, 2000

§ 102(e) Date: Aug. 14, 2000

(87) PCT Pub. No.: WO99/33800

PCT Pub. Date: Jul. 8, 1999

(30) Foreign Application Priority Data

Dec. 24, 1997 (EP) .............................................. 97122901

(51) Int. Cl.[7] ........................ A61K 31/44; A61K 31/40; C07D 209/02; C07D 209/36

(52) U.S. Cl. ...................... 514/415; 514/339; 514/418; 514/419; 546/277.1; 548/483; 548/484

(58) Field of Search ................................ 514/339, 415, 514/418, 419; 546/277; 548/483, 484

(56) References Cited

U.S. PATENT DOCUMENTS 6,184,244 B1 * 2/2001 Karanewsky
6,200,969 B1 * 3/2001 Fritz

FOREIGN PATENT DOCUMENTS

| DD | 235 866 A1 | 5/1986 |
|---|---|---|
| WO | WO 95/29189 | 11/1995 |
| WO | WO 97/08165 | 3/1997 |
| WO | WO 97/21437 | 6/1997 |
| WO | WO 97/30971 | 8/1997 |

OTHER PUBLICATIONS

Kitano, CA 125:58312, 1996.*
Elliott, CA 125: 142551, 1996.*
Beach, et al., "Two Step Synthesis of Substituted Indolo[1, 2-a]-Quinoxalin-6-Ones," *Synthetic Communications*, 25(14), pp. 2165–2183 (1995).
Bergeron, et al., "Total Synthesis of (±)-15–Deoxyspergualin," *J. Org. Chem.*, 52, pp. 1700–1703 (1987).
Borne, et al., "Conformational Analogues of Antihypertensive Agents Related to Guanethidine," *Journal of Medicinal Chemistry*, 20 (6), pp. 771–776 (1977).

Bornstein, et al., "Facile Hydrolysis of the Trifluoromethyl Group in the Presence of Base. Some Trifluoromethylated Indoles, Hydrolysis of Trifluoromethyl Group in Base," *J. Amer. Chem. Soc.*, 79, pp. 1745–1748 (1957).

Broughton, et al., "Antiallergic Activity of 2–Phenyl–8–azapurin–6–ones," *Journal of Medicinal Chemistry*, 18 (11), pp. 1117–1122 (1975).

Burton and Stoves, "The Synthesis of 5– and 6–Benzyloxy- indoles and Attempts to Prepare 5– and 6– Hydroxyindoles Therefrom," *J. Chem. Soc.*, pp. 1726–1728 (1937).

Chemical Abstracts, 32 Heterocyclic Compounds, 3441i–3442b (1962).

Cheng, et al., "Relationship Between the Inhibition Constant ($K_1$) and the Concentration of Inhibitor Which Causes 50 Per Cent Inhibition ($I_{50}$) of an Enzymatic Reaction," *Biochemical Pharmacology*, 22, pp. 3099–3108 (1973).

Chikvaidze, et al., "Synthesis of Some New Sulfur–Containing Derivatives of Indole," *Khimiya Geterotsiklicheskikh Soedinenii*, 11, pp. 1508–1511 (1991).

(List continued on next page.)

Primary Examiner—D. Margaret Seaman
(74) Attorney, Agent, or Firm—Finnegan, Henderson, Farabow, Garrett & Dunner, LLP

(57) ABSTRACT

The present invention relates to the inhibition of blood clotting proteins, and more particularly, to indole derivatives of formula (I), in which $R^{1a}$, $R^{1b}$, $R^{1c}$ $R^{1d}$, $R^2$, $R^3$, $R^4$ and A are defined as indicated in the claims. The compounds of formula (I) are inhibitors of the blood clotting enzyme factor Xa. The invention also relates to processes for the preparation of the compounds of formula (I), to methods of inhibiting factor Xa activity and of inhibiting blood clotting, to use of the compounds of formula (I) in the treatment and prophylaxis of diseases which can be cured or prevented by the inhibition of factor Xa activity such as thromboembolic diseases, and to the use of the compounds of formula (I) in the preparation of medicaments to be applied in such diseases. The invention further relates to compositions containing a compound of formula (I) in admixture or otherwise in association with an inert carrier, in particular pharmaceutical compositions containing a compound of formula (I) together with pharmaceutically acceptable carrier substances and/or auxiliary substances.

(I)

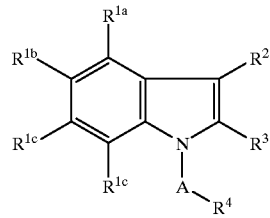

16 Claims, No Drawings

OTHER PUBLICATIONS

Eustache, et al., "N,N'–Bis(benzyloxycarbonyl)acetamidine, a Versatile Reagent for the Conversion of Amines and Alcohols to Acetamidines," *Tetrahedron Letters*, 36 (12), pp. 2045–2046 (1995).

Gray, et al., "Novel Indole–2–carboxylates as Ligands for the Strychnine–Insensitive N–Methyl–D–aspartate–Linked Glycine Receptor," *J. Med. Chem.*, 34, pp. 1283–1292 (1991).

Glamkowski, et al., "3–(1–Indolinyl)benzylamines: A New Class of Analgesic Agents," *J. Med. Chem.*, 28, pp. 66–73 (1985).

Hafner, et al., "Preparation of 2–Imino–and 2–Nitrimino–1, 3–diazacycloalkanes," *J. Org. Chem.*, 24, pp. 1157–1159 (1959).

Hauptmann, et al., "Comparison of the Antigoagulant and Antithrombotic Effects of Synthetic Thrombin and Factor Xa Inhibitors," *Thrombosis and Haemostasis*, 63 (2), pp. 220–223 (1990).

Hiremath, et al., "Synthesis & Reaction of Indole–1, 2–dicarboxaldehydes with Hydrazine & Hydroxylamine," *Indian Journal of Chemistry*, 19B, pp. 770–774 (1980).

Katakura, et al., "A Novel Factor Xa Inhibitor: Structure––Activity Relationships and Selectivity Between Factor Xa and Thrombin," *Biochemical and Biophysical Research Communications*, 197 (2), pp. 965–972 (1993).

Kim, et al., "Monosubstituted Guanidines from Primary Amines and Aminoiminomethanesulfonic Acid," *Tetrahedron Letters*, 29 (26), pp. 3183–3186 (1988).

Lindwall, et al., "Synthesis and Reactions of Indole Carboxylic Acids; Pyridindolones from Indole–2–Carboxyacetalylbenzylamides," *J. Org. Chem.*, 18, pp. 345–357 (1993).

Miki, et al., "Reaction of Indole–2,3–Dicarboxylic Anhydride with Grignard Reagents: Synthesis of 2–Acylindoles," *Heterocycles*, 45 (6), pp. 1143–1150 (1997).

Mull, et al., "Preparation of Amidines by Catalytic Reduction of Amidoximes," *J. Med. Pharm. Chem.*, 5, pp. 651–653 (1962).

Powers, J.C., "Chloroindoles," *J. Org. Chem.*, 31, pp. 2627–2631 (1966).

Salituro, et al., "3–(2–Carboxyindol–3–yl)propionic Acid Derivatives; Antagonists of the Strychnine–Insensitive Glycine Receptor Associated with the N–Methyl–D–aspartate Receptor Complex," *J. Med. Chem.*, 33, pp. 2946–2948 (1990).

Scott, et al., "Studies in the Pyrazole Series. III. Substituted Guanidines," *J. Amer. Chem. Soc.*, 75, pp. 4053–4054 (1953).

Shibata, et al., "Synthesis of Optically Active 3–Mercaptopyrrolidine Derivatives. Synthetic Intermediates of Carbapenem RS–533 and Its Isomer," *Heterocycles*, 24 (5), pp. 1331–1346 (1986).

Smith III, et al., "A Novel and Selective Method for the N–Arylation of Indoles Mediated by $KF/Al_2O_3$" *Tetrahedron Letters*, 37 (3), pp. 299–302 (1996).

Stürzebecher, et al., "Synthetic Inhbitors of Bovine Factor Xa and Thrombin Comparison of Their Anticoagulant Efficiency," *Thrombosis Research*, 54, pp. 245–252 (1989).

Unangst, et al., "Synthesis of Novel 5–Hydroxy–3–alkoxy– and 5–Hydroxy–3–alkylthio–indole–2–carboxamides," *J. Heterocycl. Chem.*, 33, pp. 1627–1630 (1996).

Wagner, et al., "Synthese von 3–[Amidinophenyl]–alaninen und 3–[Amidinophenyl]–milchsäuren," *Sektion Pharmazie*, 29 (H.1), pp. 12–15 (1974).

Weiss, et al., "Zur Guanylierung von Aminen mit O–Methyl–Isoharnstoff–sulfat," *Chemiker–Zeitung*, 98 (N: 12), pp. 617–618 (1974).

Wollweber, et al., "2–(Guanidino)–anilide und Verwandte Verbindungen," *Arzheim–Forsch./Drug Res.*, 34(I), pp. 531–542 (1984).

Zhang, et al., "Pictet–Spengler Reaction in Trifluoroacetic Acid. Large Scale Synthesis of Pyridoindolobenzodiazepine as an Atypical Antipsychotic Agent," *Tetrahedron Letters*, 36 (46), pp. 8387–8390 (1995).

* cited by examiner

INDOLE DERIVATIVES AS INHIBITORS OR FACTOR XA

The present invention relates to the inhibition of blood clotting proteins, and more particularly, to indole derivatives of the formula I.

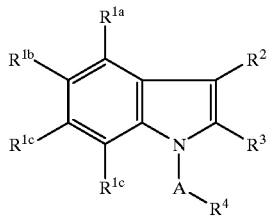

I in which $R^{1a}$, $R^{1b}$, $R^{1c}$, $R^{1d}$, $R^2$, $R^3$, $R^4$ and A are defined as indicated below. The compounds of the formula I are inhibitors of the blood clotting enzyme factor Xa. The invention also relates to processes for the preparation of the compounds of the formula I, to methods of inhibiting factor Xa activity and of inhibiting blood clotting, to the use of the compounds of formula I in the treatment and prophylaxis of diseases which can be cured or prevented by the inhibition of factor Xa activity such as thromboembolic diseases, and to the use of the compounds of formula I in the preparation of medicaments to be applied in such diseases. The invention further relates to compositions containing a compound of the formula I in admixture or otherwise in association with an inert carrier, in particular pharmaceutical compositions containing a compound of the formula I together with pharmaceutically acceptable carrier substances and/or auxiliary substances.

The ability to form blood clots is vital to survival. In certain disease states, however, the formation of blood clots within the circulatory system is itself a source of morbidity. It is nevertheless not desirable in such disease states to completely inhibit the clotting system because life threatening hemorrhage would ensue. In order to reduce the instances of the intravascular formation of blood clots those skilled in the art have endeavored to develop an effective inhibitor of factor Xa, or prothrombinase, the enzyme which is incorporated into the prothrombinase complex where it serves to activate thrombin during clot formation. Appropriate concentrations of such an inhibitor would increase the level of prothrombinase forming agents required to initiate clotting, but would not unduly prolong the clotting process once a threshold concentration of thrombin had been obtained.

Blood coagulation is a complex process involving a progressively amplified series of enzyme activation reactions in which plasma zymogens are sequentially activated by limited proteolysis. Mechanistically the blood coagulation cascade has been divided into intrinsic and extrinsic pathways, which converge at the activation of factor X; subsequent generation of the thrombin proceeds through a single common pathway (see Scheme 1).

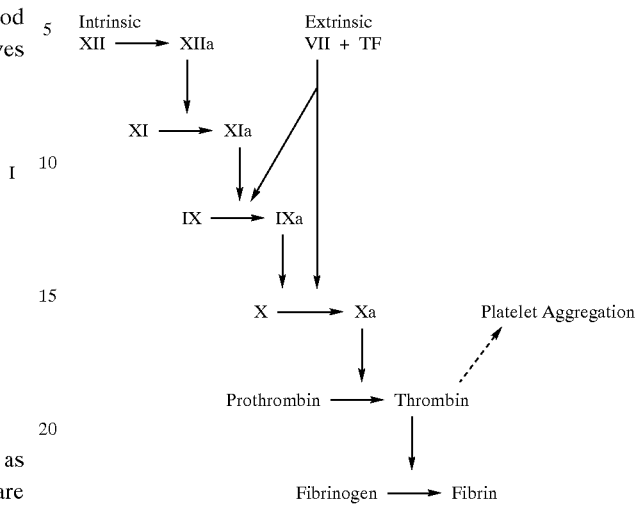

Present evidence suggests that the intrinsic pathway plays an important role in the maintenance and growth of fibrin formation, while the extrinsic pathway is critical in the initiation phase of blood coagulation. It is generally accepted that blood coagulation is physically initiated upon formation of a tissue factor/factor VIIa complex. Once formed, this complex rapidly initiates coagulation by activating factors IX and X. The newly generated activated factor X, i.e. factor Xa, then forms a one-to-one complex with factor Va and phospolipids to form a prothrombinase complex, which is responsible for converting soluble fibrinogen to insoluble fibrin via the activation of thrombin from its precursor prothrombin. As time progresses, the activity of the factor VIIa/tissue factor complex (extrinsic pathway) is suppressed by a Kunitz-type protease inhibitor protein, TFPI, which, when complexed to factor Xa, can directly inhibit the proteolytic activity of factor VIIa/tissue factor. In order to maintain the coagulation process in the presence of an inhibited extrinsic system, additional factor Xa is produced via the thrombin-mediated activity of the intrinsic pathway. Thus, thrombin plays a dual autocatalytic role, mediating its own production and the conversion of fibrinogen to fibrin.

The autocatalytic nature of thrombin generation is an important safeguard against uncontrolled bleeding and it ensures that, once a given threshold level of prothrombinase is present, blood coagulation will proceed to completion, effecting, for example, an end of the hemorrhage. Thus, it is most desirable to develop agents that inhibit coagulation without directly inhibiting thrombin. However, despite the long standing recognition of the desirability of such an inhibitor, there is at present no effective specific Xa inhibitor in clinical use.

In many clinical applications there is a great need for the prevention of intravascular blood clots or for some anti-coagulant treatment. The currently available drugs are not satisfactory in many specific clinical applications. For example, nearly 50% of patients who have undergone a total hip replacement develop deep vein thrombosis (DVT). The currently approved therapies are fixed dose low molecular weight heparin (LMWH) and variable dose heparin. Even with these drug regimes 10% to 20% of patients develop DVT and 5% to 10% develop bleeding complications.

Another clinical situation for which better anticoagulants are needed concerns subjects undergoing transluminal coronary angioplasty and subjects at risk for myocardial infarction or suffering from crescendo angina. The present, conventionally accepted therapy, which consists of administering heparin and aspirin, is associated with a 6% to 8% abrupt vessel closure rate within 24 hours of the procedure. The rate of bleeding complications requiring transfusion therapy due to the use of heparin also is approximately 7%. Moreover, even though delayed closures are significant, administration of heparin after termination of the procedures is of little value and can be detrimental.

The most widely used blood-clotting inhibitors are heparin and the related sulfated polysaccharides, LMWH and heparin sulfate. These molecules exert their anti-clotting effects by promoting the binding of a natural regulator of the clotting process, anti-thrombin III, to thrombin and to factor Xa. The inhibitory activity of heparin primarily is directed toward thrombin, which is inactivated approximately 100 times faster than factor Xa. Although relative to heparin, heparin sulfate and LMWH are somewhat more potent inhibitors of Xa than of thrombin, the differences in vitro are modest (3 to 30 fold) and effects in vivo can be inconsequential. Hirudin and hirulog are two additional thrombin-specific anticoagulants presently in clinical trials. However, these anticoagulants, which inhibit thrombin, also are associated with bleeding complications.

Preclinical studies in baboons and dogs have shown that specific inhibitors of factor Xa prevent clot formation without producing the bleeding side effects observed with direct thrombin inhibitors. Such factor Xa inhibitors include, for example, 2,7-bis-(4-amidinobenzylidene)-cycloheptanone and N($\alpha$)-tosyl-glycyl-3-amidinophenylaianine methyl ester ("TENSTOP"), which have effective inhibitory concentrations (Ki's) of about 20 nM and 800 nM, respectively. (+)-(2S)-2-(4-({(3S)-1-acetimidoyl-3-pyrrolidinyl}oxy)phenyl)-3-(7-amidino-2-naphthyl)propanoic acid also is representative of a class of factor Xa inhibitors (Katakura et al., Biochem. Biophys. Res. Comm. 197 (1993), 965–972). Thus far, however, these compounds have not been developed clinically.

Several specific inhibitors of factor Xa have been reported. Both synthetic and protein inhibitors of factor Xa have been identified including, for example, antistasin ("ATS") and tick anticoagulant peptide ("TAP"). ATS, which is isolated from the leech, *Haementerin officinalis*, contains 119 amino acids and has a Ki for factor Xa of 0.05 nM. TAP, which is isolated from the tick, *Ornithodoros moubata*, contains 60 amino acids and has a Ki for factor Xa of about 0.5 nM.

The effectiveness of recombinantly-produced ATS and TAP have been investigated in a number of animal model systems. Both inhibitors decrease bleeding time compared to other anticoagulants, and prevent clotting in a thromboplastin-induced, ligated jugular vein model of deep vein thrombosis. The results achieved in this model correlate with results obtained using the current drug of choice, heparin.

Subcutaneous ATS also was found to be an effective treatment in a thromboplastin-induced model of disseminated intravascular coagulation (DIC). TAP effectively prevents "high-shear" arterial thrombosis and "reduced flow" caused by the surgical placement of a polyester ("DACRON") graft at levels that produced a clinically acceptable prolongation of the activated partial thromboplastin time (aPTT), i.e., less than about two fold prolongation. By comparison, standard heparin, even at doses causing a five fold increase in the aPTT, did not prevent thrombosis and reduced flow within the graft. The aPTT is a clinical assay of coagulation which is particularly sensitive to thrombin inhibitors.

ATS and TAP have not been developed clinically. One major disadvantage of these two inhibitors is that administration of the required repeated doses causes the generation of neutralizing antibodies, thus limiting their potential clinical use. Moreover, the sizes of TAP and ATS render oral administration impossible, further restricting the number of patients able to benefit from these agents.

Other compounds having a factor Xa inhibitory activity have been described. WO-A-95/29 189, for example, discloses factor Xa inhibitors which have a peptide like structure, and WO-A-97/08 165 discloses cyclic guanidines which inhibit factor Xa. In WO-A-97/21 437 naphthyl-substituted benzimidazoles are described which have an inhibitory activity against factor Xa and factor IIa and which can be used as anti-coagulants, and in WO-A-97/30 971 factor Xa inhibitory m-amidino phenyl analogs are described. But there is still a need for further factor Xa inhibitors having improved properties like a favorable pharmacological activity profile.

A specific inhibitor of factor Xa would have substantial practical value in the practice of medicine. In particular, a factor Xa inhibitor would be effective under circumstances where the present drugs of choice, heparin and related sulfated polysaccharides, are ineffective or only marginally effective. Thus, there exists a need for a low molecular weight factor Xa-specific blood clotting inhibitor that is effective, but does not cause unwanted side effects. The present invention satisfies this need by providing novel factor Xa activity inhibiting indole derivatives of the formula I and by providing related advantages as well.

As used herein, the term "factor Xa activity" refers to the ability of factor Xa, by itself or in the assembly of subunits known as the prothrombinase complex, to catalyze the conversion of prothrombin to thrombin. When used in reference to factor Xa activity, the term "inhibition" includes both the direct and indirect inhibition of factor Xa activity. Direct inhibition of factor Xa activity can be accomplished, for example, by the binding of a compound of the formula I to factor Xa or to prothrombinase so as to prevent the binding of prothrombin to the prothrombinase complex active site. Indirect inhibition of factor Xa activity can be accomplished, for example, by the binding of a compound of the invention to soluble factor Xa so as to prevent its assembly into the prothrombinase complex. As used herein, the term "specific" when used in reference to the inhibition of factor Xa activity means that a compound of the formula I can inhibit factor Xa activity without substantially inhibiting the activity of other specified proteases, including plasmin and thrombin (using the same concentration of the inhibitor). Such proteases are involved in the blood coagulation and fibrinolysis cascade. The present invention provides novel compounds which inhibit factor Xa activity but do not substantially inhibit the activity of other proteases involved in the blood coagulation pathway.

Thus, a subject of the present invention are indole derivatives of the formula I,

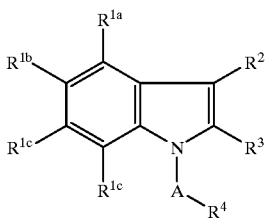

wherein two of the residues $R^{1a}$, $R^{1b}$, $R^{1c}$ and $R^{1d}$ independent of one another are hydrogen, F, Cl, Br, I, $(C_1-C_4)$-alkyl, $CF_3$, phenyl, phenyl-$(C_1-C_4)$-alkyl-, $(C_1-C_4)$-alkoxy, phenyloxy-, phenyl-$(C_1-C_4)$-alkoxy-, OH, $NO_2$, —$NR^{5a}R^{5b}$, —$NR^{5b}$—$SO_2$—$R^{6a}$, —S—$R^{6b}$, —$SO_nR^{6c}$ where n is 1 or 2, —$SO_2$—$NR^{5a}R^{5b}$, —CN or —CO—$R^7$, and are identical or different, and the other two of the residues $R^{1a}$, $R^{1b}$, $R^{1c}$ and $R^{1d}$ are hydrogen;

$R^{5a}$ is hydrogen, $(C_1-C_4)$-alkyl, phenyl, phenyl-$(C_1-C_4)$-alkyl-, formyl, $((C_1-C_4)$-alkyl)carbonyl-, phenylcarbonyl-, phenyl-$((C_1-C_4)$-alkyl)carbonyl-, $((C_1-C_4)$-alkoxy)carbonyl- or phenyl-$((C_1-C_4)$-alkoxy)carbonyl-;

$R^{5b}$ is hydrogen, $(C_1-C_4)$-alkyl, phenyl or phenyl-$(C_1-C_4)$-alkyl-;

$R^{6a}$ is $(C_1-C_4)$-alkyl, phenyl, phenyl-$(C_1-C_4)$-alkyl- or phenyl-NH-;

$R^{6b}$ is $(C_1-C_4)$-alkyl, phenyl or phenyl-$(C_1-C_4)$-alkyl-;

$R^{6c}$ is hydroxy, $(C_1-C_4)$-alkyl, phenyl or phenyl-$(C_1-C_4)$-alkyl-;

$R^7$ is hydroxy, $(C_1-C_4)$-alkoxy, phenyl-$(C_1-C_4)$-alkoxy- or —$NR^{5a}R^{5b}$;

where all residues $R^{5a}$, $R^{5b}$, $R^{6a}$, $R^{6b}$, $R^{6c}$ and $R^7$ if present more than one time in the molecule, are independent of one another and can each be identical or different;

and where phenyl present in the residues $R^{1a}$, $R^{1b}$, $R^{1c}$, $R^{1d}$, $R^{5a}$, $R^{5b}$, $R^{6a}$, $R^{6b}$, $R^{6c}$ and $R^7$ denotes an unsubstituted phenyl residue or a phenyl residue which is substituted by one or two identical or different substituents selected from the series consisting of $(C_1-C_4)$-alkyl, F, Cl, Br, $CF_3$, $(C_1-C_4)$-alkoxy, $NO_2$, OH, $NH_2$ and CN;

one of the residues $R^2$ and $R^3$ is —$(CH_2)_p$—CO—$R^8$ and the other is hydrogen, F, Cl, Br, $(C_1-C_4)$-alkyl or —$(CH_2)_p$—CO—$R^8$, or $R^2$ and $R^3$ together form a group of the formula —$CH_2$—$CH_2$—N(—CO—$R^{20}$)—$CH_2$— wherein $R^{20}$ is phenyl, phenyl-$(C_1-C_4)$-alkyl-, pyridyl or pyridyl-$(C_1-C_4)$-alkyl- and where each phenyl residue is unsubstituted or substituted by $R^{15a}$ and each pyridyl residue is unsubstituted or substituted at the nitrogen atom by $R^{14}$;

p is 0, 1 or 2;

$R^8$ is —$NR^9R^{10}$, —$OR^{10}$ or —S—$(C_1-C_4)$-alkyl, where residues $R^8$ if present more than one time in the molecule, are independent of each other and can be identical or different;

$R^9$ is hydrogen, $(C_1-C_4)$-alkyl-, hydroxycarbonyl-$(C_1-C_4)$-alkyl-, $((C_1-C_4)$-alkoxy)carbonyl-$(C_1-C_4)$-alkyl- or aminocarbonyl-$(C_1-C_4)$-alkyl-;

$R^{10}$ is hydrogen, $(C_1-C_{10})$-alkyl-, phenyl, naphthyl, phenyl-$(C_1-C_4)$-alkyl-, naphthyl-$(C_1-C_4)$-alkyl-, pyridyl or the residue Het, where the $(C_1-C_{10})$-alkyl-residue and each phenyl and naphthyl residue is unsubstituted or substituted by one, two or three identical or different residues $R^{11}$, and where the pyridyl residue is unsubstituted or substituted at the nitrogen atom by $R^{14}$, and where Het is unsubstituted or substituted by $R^{15a}$;

or $R^9$ and $R^{10}$ together with the nitrogen atom to which they are bonded form a 5-membered or 6-membered saturated heterocyclic ring which can contain an additional nitrogen atom in the ring and which is unsubstituted or substituted by $R^{15a}$ or by —CO—$R^7$;

Het is the residue of a 5-membered or 6-membered saturated heterocyclic ring containing 1 or 2 identical or different ring heteroatoms selected from the series consisting of nitrogen, oxygen and sulfur;

$R^{11}$ is —$N(R^{12})_2$, —$OR^{12}$, —CO—$N(R^{13})_2$, —CO—$R^7$, $R^{15b}$, $(C_1-C_{14})$-alkyl, phenyl which is unsubstituted or substituted by one, two or three identical or different residues $R^{15b}$, naphthyl which is unsubstituted or substituted by one, two or three identical or different residues $R^{15b}$, quinolinyl which is unsubstituted or substituted by one, two or three identical or different residues $R^{15b}$ and/or substituted at the nitrogen atom by $R^{14}$, isoquinolinyl which is unsubstituted or substituted by one, two or three identical or different residues $R^{15b}$ and/or substituted at the nitrogen atom by $R^{14}$, pyridyl which is unsubstituted or substituted at the nitrogen atom by $R^{14}$, or Het which is unsubstituted or substituted by $R^{15a}$, where residues $R^{11}$ if present more than one time in the molecule, are independent of each other and can be identical or different;

each residue $R^{12}$ independent of the denotation of another residue $R^{12}$ is hydrogen, $(C_1-C_4)$-alkyl, phenyl, phenyl-$(C^1-C_4)$-alkyl-, naphthyl, naphthyl-$(C_1-C_4)$-alkyl-, pyrrolidinyl, piperidinyl, pyrrolidinyl-$(C_1-C_4)$-alkyl- or piperidinyl-$(C_1-C_4)$-alkyl-, where each pyrrolidinyl residue and each piperidinyl residue is unsubstituted or substituted at the nitrogen atom by phenyl-$(C_1-C_4)$-alkyl- or $R^{15a}$;

each residue $R^{13}$ independent of the denotation of another residue $R^{13}$ is hydrogen, $(C_1-C_4$-alkyl, phenyl, phenyl-$(C^1-C_4)$-alkyl-, naphthyl or naphthyl-$(C_1-C_4)$-alkyl-, or the two residues $R^{13}$ together with the nitrogen atom to which they are bonded form a 5-membered or 6-membered saturated heterocyclic ring which can contain an additional nitrogen atom or oxygen atom in the ring where the additional nitrogen atom in the ring is unsubstituted or substituted by $(C_1-C_4)$-alkyl or phenyl-$(C_1-C_4)$-alkyl-;

$R^{14}$ is $(C_1-C_6)$-alkyl, $(C_1-C_6)$-alkenyl, $(C_1-C_6)$-alkynyl, phenyl-$(C_1-C_6)$-alkyl- or $((C_1-C_8)$-alkoxy)carbonyl-$(C_1-C_6)$-alkyl-, where phenyl present in $R^{14}$ denotes an unsubstituted phenyl residue, the substitution by these residues at the nitrogen atom of the heterocyclic residue leading to a positively charged group having $X^-$ as the counterion; or $R^{14}$ is oxido this substitution at the nitrogen atom of the heterocyclic residue leading to an N-oxide; and where residues $R^{14}$ if present more than one time in the molecule, are independent of each other and can be identical or different;

$R^{15a}$ is $(C_1-C_6)$-alkyl, $((C_1-C_6)$-alkyl)-C(=NH)—, —$(CH_2)_r$—$N(R^{16})_2$, —$(CH_2)_r$—$N^+(R^{16a})_2(-O^-)$, —$(CH_2)_r$—$N^+(R^{16a})_3X^-$, —$(CH_2)_r$—$NHR^{17}$, —$(CH_2)_r$—CN, —$(CH_2)_r$—CS—$N(R^{18})_2$, —$(CH_2)_r$—C(=$NR^{17}$)—$NHR^{17}$ or —$(CH_2)_r$—NH—C(=$NR^{17}$)—

NHR$^{17}$, where ((C$_1$–C$_6$)-alkyl)-C(=NH)— is bonded to a ring nitrogen atom, and where residues R$^{15a}$ if present more than one time in the molecule, are independent of each other and can be identical or different;

R$^{15b}$ is (C$_1$–C$_6$)-alkyl, hydroxy, (C$_1$–C$_4$)-alkoxy, F, Cl, Br, I, NO$_2$, —(CH$_2$)$_t$—N(R$^{16}$)$_2$, —(CH$_2$)$_t$—N$^+$(R$^{16a}$)$_2$(—O$^-$), —(CH$_2$)$_t$—N$^+$(R$^{16}$)$_3$X$^-$, —(CH$_2$)$_t$—NHR$^{17}$, —(CH$_2$)$_t$—CO—OR$^{18}$, —(CH$_2$)$_t$—CO—N(R$^{18}$)$_2$, —(CH$_2$)$_t$—CN, —(CH$_2$)$_t$—CS—N(R$^{18}$)$_2$, —(CH$_2$)$_t$—C(=NR$^{17}$)—NHR$^{17}$ or —(CH$_2$)$_t$—NH—C(=NR$^{17}$)—NHR$^{17}$, where alkyl can be substituted 1, 2, 3, 4, 5, 6, or 7 times by fluoro, and where residues R$^{15b}$ if present more than one time in the molecule, are independent of each other and can be identical or different;

t is 0, 1, 2 or 3, where numbers t, if present more than one time in the molecule, are independent of each other and can be identical or different;

each residue R$^{16}$ independent of the denotations of another residue R$^{16}$ is hydrogen, (C$_1$–C$_6$)-alkyl, (C$_1$–C$_6$)-alkenyl, (C$_1$–C$_6$)-alkynyl, phenyl-(C$_1$–C$_6$)-alkyl- or or ((C$_1$–C$_6$)-alkoxy)carbonyl-(C$_1$–C$_6$)-alkyl-, where phenyl present in R$^{16}$ denotes an unsubstituted phenyl residue, and where groups containing residues R$^{18}$ if present more than one time in the molecule, are independent of each other and can be identical or different;

each residue R$^{16a}$ independent of the denotations of another residue R$^{16a}$ is (C$_1$–C$_6$)-alkyl, (C$_1$–C$_6$)-alkenyl, (C$_1$–C$_6$)-alkynyl, phenyl-(C$_1$–C$_6$)-alkyl- or ((C$_1$–C$_6$)-alkoxy)carbonyl-(C$_1$–C$_6$)-alkyl-, where phenyl present in R$^{16a}$ denotes an unsubstituted phenyl residue, and where groups containing residues R$^{16a}$, if present more than one time in the molecule, are independent of each other and can be identical or different;

each residue R$^{17}$ independent of the denotation of another residue R$^{17}$ is hydrogen, (C$_1$–C$_6$)-alkyl, (C$_1$–C$_6$)-alkylcarbonyl-, (C$_1$–C$_6$)-alkoxycarbonyl-, (C$_1$–C$_6$)-alkylcarbonyloxy-(C$_1$–C$_6$)-alkoxycarbonyl-, phenylcarbonyl-, phenoxycarbonyl-, phenyl-(C$_1$–C$_6$)-alkoxycarbonyl-, hydroxy, (C$_1$–C$_6$)-alkoxy, phenyl-(C$_1$–C$_6$)-alkoxy- or amino, and additionally in the groups —(CH$_2$)$_t$—C(=NR$^{17}$)—NHR$^{17}$ and —(CH$_2$)$_t$—NH—C(=NR$^{17}$)—NHR$^{17}$ the two residues R$^{17}$ together with the C(=N)—NH group to which they are bonded, can form a 5-membered or 6-membered heterocyclic ring, and where phenyl present in R$^{17}$ denotes an unsubstituted phenyl residue, and where groups containing residues R$^{17}$ if present more than one time in the molecule, are independent of each other and can be identical or different;

each residue R$^{18}$ independent of the denotation of another residue R$^{18}$ is hydrogen or (C$_1$–C$_4$)-alkyl;

A is a direct linkage, a divalent —(C$_1$–C$_4$)-alkyl- residue which is saturated or which contains a double bond or a triple bond, —CO—, —SO$_r$— wherein r is 1 or 2, —CO—(C$_1$–C$_4$)-alkyl-, —(C$_1$–C$_4$)-alkyl-CO— or —(C$_1$–C$_4$)-alkyl-CO—NH— wherein the nitrogen is bonded to R$^4$;

R$^4$ is phenyl which is substituted by one residue R$^{15c}$ and which can additionally be substituted by one or two substituents from the series consisting of (C$_1$–C$_4$)-alkyl, F, Cl and Br, or R$^4$ is pyridyl which is unsubstituted or substituted at the nitrogen atom by R$^{14}$, or R$^4$ is the residue Het which is substituted by R$^{15d}$;

R$^{15c}$ is —(CH$_2$)$_t$—N(R$^{16}$)$_2$, —(CH$_2$)$_t$—N$^+$(R$^{16a}$)$_2$(—O$^-$), —(CH$_2$)$_t$—N$^+$(R$^{16a}$)$_3$X$^-$, —(CH$_2$)$_t$—NHR$^{17}$, —(CH$_2$)$_t$—CN, —(CH$_2$)$_t$—CS—N(R$^{18}$)$_2$, —(CH$_2$)$_t$—C(=NR$^{17}$)—NHR$^{17}$ or —(CH$_2$)$_t$—NH—C(=NR$^{17}$)—NHR$^{17}$;

R$^{15d}$ is ((C$_1$–C$_6$)-alkyl)-C(=NH)—, —(CH$_2$)$_t$—N(R$^{16}$)$_2$, —(CH$_2$)$_t$—N$^+$(R$^{16a}$)$_2$(—O$^-$), —(CH$_2$)$_t$—N$^+$(R$^{16a}$)$_3$X$^-$, —(CH$_2$)$_t$—NHR$^{17}$, —(CH$_2$)$_t$—CN, —(CH$_2$)$_t$—CS—N(R$^{18}$)$_2$, —(CH$_2$)$_t$—C(=NR$^{17}$)—NHR$^{17}$ or —(CH$_2$)$_t$—NH—C(=NR$^{17}$)—NHR$^{17}$, where ((C$_1$–C$_6$)-alkyl)-C(=NH)— is bonded to a ring nitrogen atom;

X$^-$ is a physiologically acceptable anion;

in all their stereoisomeric forms and mixtures thereof in any ratio, and their physiologically acceptable salts.

In general, residues or substituents which can occur more than once in compounds of the formula I can all independently of one another have the meanings indicated, and can in all cases be identical or different.

Alkyl residues present in the compounds of the formula I can be straight-chain or branched. This also applies when they carry substituents or occur as substituents in other residues such as, for example, in alkoxy residues, alkylcarbonyl residues, alkoxycarbonyl residues or phenylalkyl residues. An alkyl residue like (C$_1$–C$_6$)-alkyl comprises alkyl residues having 1, 2, 3, 4, 5 or 6 carbon atoms, an alkyl residue like (C$_1$–C$_6$)-alkyl in addition alkyl residues having 7, 8, 9 or 10 carbon atoms, an alkyl residue like (C$_1$–C$_{14}$)-alkyl in addition alkyl residues having 11, 12, 13 or 14 carbon atoms. Examples of alkyl residues are methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, isopropyl, isobutyl, isopentyl, isohexyl, isooctyl, neopentyl, 3-methylpentyl, sec-butyl, tert-butyl and tert-pentyl. A group of preferred alkyl residues is formed by the residues methyl, ethyl, n-propyl, isopropyl, n-butyl, isobutyl, sec-butyl and tert-butyl. Examples of fluoro-substituted alkyl groups are trifluoromethyl, pentafluoroethyl, heptafluoropropyl or 2,2,2-trifluoroethyl, in particular trifluoromethyl.

Further, as used herein, the term alkyl comprises acyclic alkyl residues as well as alkyl residues which contain one or more alicyclic ring system. Thus, in addition to acyclic alkyl residues the term alkyl expressly also comprises cycloalkyl residues which are bonded via a ring carbon atom, and cycloalkyl-alkyl residues which are bonded via a carbon atom in an acyciic subunit. This also applies when alkyl residues carry substituents or occur as substituents in other residues such as, for example, in alkoxy residues, alkylcarbonyl residues, alkoxycarbonyl residues or phenylalkyl residues. Cycloalkyl residues representing alkyl residues or being contained in alkyl residues can be monocyclic or polycyclic, for example monocyclic, bicyclic or tricyclic. Of course, the term alkyl comprises only such cyclic residues which are stable in view of the number of carbon atoms present in the alkyl residue considered. As monocylic alkyl residues have to contain at least three carbon atoms in the ring a (C$_1$–C$_4$)-alkyl residue, for example, comprises also (C$_3$–C$_4$)-monocycloalkyl residues, a (C$_1$–C$_6$)-alkyl residue comprises also (C$_3$–C$_6$)-monocycloalkyl residues, a (C$_1$–C$_{10}$)-alkyl residue comprises also (C$_3$–C$_{10}$)-monocycloalkyl residues or a (C$_1$–C$_{14}$)-alkyl residue comprises also (C$_3$–C$_{14}$)-monocycloalkyl residues. Bicyclic and tricyclic alkyl residues preferably contain 6, 7, 8, 9, 10, 11, or 12 carbon atoms. Thus, a (C$_1$–C$_{10}$)-alkyl residue, for example, comprises also (C$_6$–C$_{10}$)-bicycloalkyl residues and (C$_6$–C$_{10}$)-tricycloalkyl residues, or a (C$_1$–C$_{14}$)-alkyl residue comprises also (C$_6$–C$_{14}$)-bicycloalkyl residues and (C$_6$–C$_{14}$)-tricycloalkyl residues, both preferably comprising bicycloalkyl residues and tricycloalkyl residues having 7 or more carbon atoms. Examples of cyclic alkyl residues or of alkyl-substituted alkyl residues wherein the alkyl group regarded as a substituent is a cyclic residue, are cyclopropyl, cyclopropylmethyl, cyclopropylethyl, cyclopropylpropyl, cyclopropylbutyl, cyclopropylpentyl, cyclopropylhexyl, cyclopropylheptyl, cyclobutyl, cyclobutylmethyl, cyclobutylethyl, cyclobutylpropyl, cyclobutylbutyl, cyclobutylpentyl, cyclobutylhexyl, cyclopentyl, cyclopentylmethyl, cyclopentylethyl, cyclopentylpropyl, cyclopentylbutyl, cyclopentylpentyl, cyclohexyl, cyclohexyimethyl, cyclohexylethyl, cyclohexylpropyl, cyclohexylbutyl, cycloheptyl, cyclooctyl, octahydroindenyl, bicyclo[4.2.0]octyl, octahydropentalenyl, bicyclo[3.3.1]nonyl, tetradecahydrophenanthryl, dodecahydrophenalenyl, octahydro-1,4-ethano-indenyl, adamantyl or adamantylmethyl, wherein the ethyl, propyl, butyl, pentyl, hexyl and heptyl groups carrying the cyclic groups can be straight-chain or branched as described above. The cyclic groups can be bonded via any suitable carbon atom. Residues derived from bridged hydrocarbons can be bonded via bridgehead carbon atoms or carbon atoms in the bridges. Adamantyl, for example, can be 1-adamantyl or 2-adamantyl.

Alkenyl residues and alkynyl residues can also be straight-chain or branched. Examples of alkenyl residues are vinyl, 1-propenyl, 2-propenyl (=allyl), butenyl, 3-methyl-2-butenyl, pentenyl and hexenyl, examples of alkynyl residues are ethynyl, 1-propynyl, 2-propynyl (=propargyl), butynyl, pentynyl and hexynyl.

The above statements relating to alkyl, alkenyl and alkynyl residues correspondingly apply to divalent alkyl residues, alkenyl residues and alkynyl residues, i.e. to alkylene residues or alkanediyl residues, alkenylene residues or alkenediyl residues and alkynylene residues or alkynediyl residues occurring, for example, in the residue A which can be a divalent alkyl residue which is saturated or contains a double bond or a triple bond. Examples of saturated divalent alkyl residues are methylene (—$CH_2$—), methylmethylene (—$CH(CH_3)$—), dimethylmethylene (—$C(CH_3)_2$—), ethylene (—$CH_2$—$CH_2$—), methylethylene (—$CH(CH_3)$—$CH_2$— and —$CH_2$—$CH(CH_3)$—), trimethylene —$(CH_2)_3$— or tetramethylene —$(CH_2)_4$—, examples of unsaturated residues are vinylene (—CH=CH—), 1-propenylene and 2-propenylene (—CH=CH—$CH_2$— and —$CH_2$—CH=CH—), 2-butenylene (—$CH_2$—CH=CH—$CH_2$—), 2,3-dimethyl-2-butenylene (—$CH_2$—$C(CH_3)$=$C(CH_3)$—$CH_2$—), 1-propynylene and 2-propynylene (—C≡C—$CH_2$— and —$CH_2$—C≡C—), or 2-butynylene (—$CH_2$—C≡C—$CH_2$—).

In monosubstituted phenyl residues the substituent can be located in the 2-position, the 3-position or the 4-position, with the 3-position and the 4-position being preferred. If phenyl is substituted twice, the substituents can be in the 2,3-position, the 2,4-position, the 2,5-position, the 2,6-position, the 3,4-position or the 3,5-position. In phenyl residues carrying three substituents the substituents can be in the 2,3,4-position, 2,3,5-position, 2,3,6-position, 2,4,5-position, 2,4,6-position, or 3,4,5-position.

Naphthyl residues can be 1-naphthyl and 2-naphthyl. In substituted naphthyl residues the substituents can be in any positions, i.e. in monosubstituted 1-naphthyl residues in the 2-, 3-, 4-, 5-, 6-, 7-, or 8-position and in monosubstituted 2-naphthyl residues in the 1-, 3-, 4-, 5-, 6-, 7-, or 8-position.

Examples of pyridyl residues are 2-pyridyl, 3-pyridyl and 4-pyridyl. Also if a pyridyl residue present in a compound of the formula I is substituted at the nitrogen atom by an oxido group —$O^-$, i.e. if a pyridine N-oxide residue is present in a compound of the formula I, it can be bonded via the 2-position, the 3-position or the 4-position of the pyridine ring. This also applies to pyridyl residues in which the nitrogen atom is substituted by an alkyl group etc. this substitution leading to a positively charged pyridinium group.

Quinolinyl and isoquinolinyl residues can be 2-, 3-, 4-, 5-, 6-, 7- or 8-quinolinyl and 1-, 3-, 4-, 5-, 6-, 7- or 8-isoquinolinyl, respectively. In substituted quinolinyl and isoquinolinyl residues the substituents can be present in any desired positions, for example in a monosubstituted 4-quinolinyl residue in the 2-, 3-, 5-, 6-, 7- or 8-position and in a monosubstituted 1-isoquinolinyl residue in the 3-, 4-, 5-, 6-, 7- or 8-position. Also if a quinolinyl or isoquinolinyl residue present in a compound of the formula I is substituted at the nitrogen atom by an oxido group —$O^-$, i.e. if a quinoline or isoquinoline N-oxide residue is present in a compound of the formula I, it can be bonded via any desired position. This also applies to quinolinyl and isoquinolinyl residues in which the nitrogen atom is substituted by an alkyl group etc. this substitution leading to a positively charged quinolinium or isoquinolinium group.

Groups like alkyl groups, phenyl groups, naphthyl groups, quinolinyl groups or isoquinolinyl groups which occur in or which represent groups like $R^{10}$ or $R^{11}$ and which can carry as substituents one or more of the groups representing $R^{15b}$, can preferably carry not more than two, in particular not more than one of the groups —$(CH_2)_t$—$N(R^{16})_2$, —$(CH_2)_t$—$N^+(R^{16a})_2(-O^-)$, —$(CH_2)_t$—$N^+(R^{16a})_3X^-$, —$(CH_2)_t$—$NHR^{17}$, —$(CH_2)_t$—CO—$OR^{18}$, —$(CH_2)_t$—CO—$N(R^{18})_2$, —$(CH_2)_t$—CN, —$(CH_2)_t$—CS—$N(R^{18})_2$, —$(CH_2)_t$—C(=$NR^{17}$)—$NHR^{17}$ and —$(CH_2)_t$—NH—C(=$NR^{17}$)—$NHR^{17}$. Of groups like ($C_1$–$C_6$)-alkyl, hydroxy, ($C_1$–$C_4$)-alkoxy, F, Cl, Br, I, $NO_2$, and fluoro-substituted alkyl which can be present as substituents in such alkyl groups, phenyl groups etc., there usually can be present also more than one or more than two groups, for example one, two or three identical or different groups, either in addition to the first listed groups —$(CH_2)_t$—$N(R^{16})_2$ etc., or without one of the first listed groups being present.

Unless stated otherwise, aryl groups like phenyl or naphthyl that are present in the compounds of the formula I can in general be unsubstituted or can be substituted in any desired positions by one or more, for example one, two or three, identical or different substituents, for example substituents like ($C_1$–$C_4$)-alkyl such as methyl or tert-butyl, hydroxy, ($C_1$–$C_4$)-alkoxy such as methoxy, ethoxy or tert-butoxy, methylenedioxy, ethylenedioxy, F, Cl, Br, I, cyano, nitro, trifluoromethyl, hydroxymethyl, formyl, acetyl, amino, mono- or di-($C_1$–$C_4$)-alkylamino, (($C_1$–$C_4$)-alkyl)carbonylamino, hydroxycarbonyl, (($C_1$–$C_4$)-alkoxy)carbonyl, carbamoyl, phenyl, benzyl, phenoxy or benzyloxy.

In general, not more than two nitro groups can be present in the compounds of the formula I.

Examples of the 5-membered or 6-membered saturated heterocyclic rings that can be formed by $R^9$ and $R^{10}$ together with the nitrogen atom to which they are bonded are pyrrolidine, piperidine, pyrazolidine, imidazolidine, hexahydropyrimidine and piperazine. Substituents present in this ring can be bonded to any position unless stated otherwise. Examples of the 5-membered or 6-membered saturated heterocyclic rings that can be formed by the two residues $R^{13}$ together with the nitrogen atom to which they are bonded are pyrrolidine, piperidine, piperazine or morpholine.

Examples of Het are pyrrolidine, piperidine, perhydroazepine, tetrahydrofuran, perhydropyrane, tetrahydrothiophene, perhydrothiopyran, pyrazolidine, imidazolidine, hexahydropyridazine, hexahydropyrimidine, piperazine, dioxolane, perhydrodioxane, oxazolidine, isoxazolidine, thiazolidine, isothiazolidine, perhydro-1,2-oxazine, perhydro-1,3-oxazine, perhydro-1,4-oxazine (morpholine), perhydro-1,3-thiazine and perhydro-1,4-thiazine (thiomorpholine). Preferred groups Het include, for example, groups containing one nitrogen atom as ring heteroatom like pyrrolidine or piperidine. Substituents present in Het can be bonded to any position unless stated otherwise. A ring nitrogen atom present in Het can carry one or two substituents. When a ring nitrogen atom carries two substituents, i.e. when it is quaternized, it is positively charged, and the compound of the formula I then also comprises an anion X$^-$ as counterion. In general a group Het can carry one or more than one substituents, for example one, two, three, four or five identical or different substituents. Of the groups representing $R^{15a}$ which can be present as substituents in a group Het, preferably only one or two, in particular not more than one, of the groups ($(C_1-C_6)$-alkyl)-C(=NH)—, —(CH$_2$)$_r$—N(R$^{16}$)$_2$, —(CH$_2$)$_r$—N$^+$(R$^{16a}$)$_2$(—O$^-$), —(CH$_2$)$_r$—N$^+$(R$^{16a}$)$_3$X$^-$, —(CH$_2$)$_r$—NHR$^{17}$, —(CH$_2$)$_r$—CN, —(CH$_2$)$_r$—CS—N(R$^{18}$)$_2$, —(CH$_2$)$_r$—C(=NR$^{17}$)—NHR$^{17}$ and —(CH$_2$)$_r$—NH—C(=NR$^{17}$)—NHR$^{17}$ can be present as a substituent in Het whereas, for example, $(C_1-C_6)$-alkyl substituents can be present once or more than once in Het, for example one, two, three or four times, either without a substituent from the first group being present or in addition to substituents from the first group. Similarly, a group Het representing $R^4$ preferably carries only one of the residues representing $R^{15d}$. These statements correspondingly apply to substituents in other heterocyclic rings. A group Het and similar heterocyclic groups can in general be substituted by substituents like, for example, $(C_1-C_6)$-alkyl groups and also other substituents, for example phenyl-$(C_1-C_4)$-alkyl- groups like a benzyl group.

Examples of 5-membered or 6-membered heterocyclic rings which can be formed by two residues $R^{17}$ together with the C(=N)—NH group to which they are bonded, are 4,5-dihydro-1H-imidazole and 1,4,5,6-tetrahydropyrimidine.

Examples of the substituent (($C_1-C_6$)-alkyl)-C(=NH)— which is attached to the ring nitrogen atom of a heterocycle are the acetimidoyl residue, i.e. the residue CH$_3$—C(=NH)—, or the residues CH$_3$—CH$_2$—C(=NH)—, CH$_3$—CH$_2$—CH$_2$—C(=NH)— or (CH$_3$)$_2$CH—C(=NH)—.

In the following some groups containing the substituent (($C_1-C_6$)-alkyl)-C(=NH)— are listed which can be present in the residues $R^2$ and/or $R^3$. Similar groups can be present in the residue $R^4$. The following groups correspond to the group $R^8$ in the definition of the compounds of the formula I and are bonded to the CO group in the group —(CH$_2$)$_p$—CO—R$^6$ via the nitrogen atom or the oxygen atom having a free bond which is indicated in the following formulae by the line starting from an oxygen atom or an NH group. In the following formulae the substituent (($C_1-C_6$)-alkyl)-C(=NH)— is abbreviated as Aim.

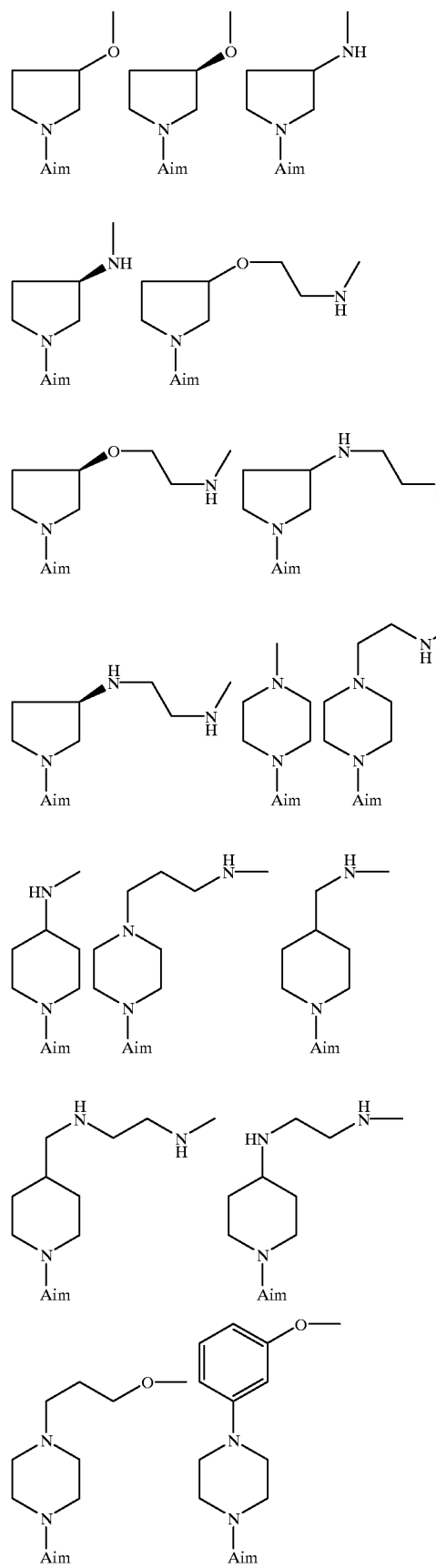

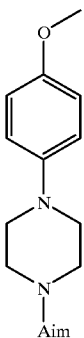

A residue represented by the formula —$(CH_2)_r$—$N^+(R^{16a})_2$(—$O^-$) is the residue of an amine oxide.

Physiologically acceptable anions $X^-$ which are present in the compounds of the formula I when a positively charged group like a quaternary ammonium group or a pyridinium, quinolinium or isoquinolinium group is present, can be anions derived from suitable inorganic acids or organic carboxylic acids or sulfonic acids. Suitable acids are, in particular, pharmaceutically utilizable or non-toxic acids. Examples of such acids are those given below as examples of acids which can form physiologically acceptable salts with compounds of the formula I containing basic groups. If a compound of the formula I contains an anion $X^-$ and simultaneously is present as an acid addition salt formed at a basic group, the anion $X^-$ can be the same as or different from the anion introduced by salt formation.

Physiologically acceptable salts of the compounds of the formula I are, in particular, pharmaceutically utilizable or non-toxic salts. Such salts are formed, for example, from compounds of the formula I which contain acid groups, for example carboxylic acid or sulfonic acid groups. Examples of such salts are salts containing cations of alkali metals or alkaline earth metals, such as, for example, sodium, potassium, magnesium or calcium salts, or salts containing the unsubstituted ammonium cation $NH_4^+$ or organic ammonium cations, the latter including cations obtained from physiologically acceptable organic amines, such as, for example, methylamine, ethylamine, triethylamine, ethanolamine, tris(2-hydroxyethyl)amine or amino acids by protonation, and suitable quaternary ammonium cations like, for example, tetramethylammonium.

Compounds of the formula I which contain basic groups, for example one or more amino groups and/or amidino groups and/or guanidino groups, form acid addition salts with, for example, inorganic acids, organic carboxylic acids and organic sulfonic acids. Examples of such acids the anions of which can be present in physiologically acceptable salts of the compounds of formula I are hydrochloric acid, hydrobromic acid, sulfuric acid, phosphoric acid, acetic acid, benzoic acid, oxalic acid, malonic acid, succinic acid, maleic acid, fumaric acid, malic acid, tartaric acid, citric acid, methanesulfonic acid, p-toluenesulfonic acid or naphthalenesulfonic acids.

The present invention also covers inner salts, zwitterions or betaines of the compounds of the formula I.

Physiologically acceptable salts of the compounds of formula I can be prepared according to standard procedures, for example by combining the compound of the formula I with the desired base, for example with an alkaline metal hydroxide or carbonate or hydrogen carbonate or an amine, or with the desired acid in a solvent or diluent. A physiologically acceptable salt of a compound of the formula I can also be prepared from another salt by cation exchange or anion exchange by standard procedures. Moreover, the present invention also covers salts of the compounds of the formula I which are, for example, obtained during the chemical synthesis of the compounds and which are less suitable for the desired use of the compounds of the formula I but which can be used as starting materials for the subsequent preparation of a desired physiologically acceptable salt. The present invention further covers solvates of the compounds of the formula I, for example hydrates or alcoholates.

The compounds of the formula I can be present in stereoisomeric forms. The present invention covers all possible stereoisomers. For example, the compounds of the formula I according to the invention can contain optically active carbon atoms which independently of one another can have R configuration or S configuration. The compounds of the formula I can thus be present in the form of individual enantiomers or individual diastereomers or in the form of enantiomeric mixtures including racemates or diastereomeric mixtures. The present invention relates both to pure enantiomers and mixtures of enantiomers in all ratios, and to pure diastereomers and mixtures of diastereomers in all ratios. The invention covers mixtures of two stereoisomers as well as mixtures of more than two stereoisomers, and all ratios of stereoisomers in the mixtures. The compounds of the formula I can also be present as E isomers or Z isomers (or cis isomers or trans isomers). The present invention relates to both pure E isomers and Z isomers and to mixtures of E isomers and Z isomers in all ratios.

Diastereomers, including E/Z isomers, can be separated into the individual isomers, for example by chromatography. Mixtures of enantiomers including racemates can be separated into the two enantiomers by chromatography on chiral phases or by resolution according to standard procedures like crystallization of diastereomeric salts obtained with auxiliary agents. Stereochemically pure compounds, for example pure enantiomers, can also be obtained by employing into the synthesis optically active starting materials, or by using stereoselective reactions.

The compounds of the formula I according to the invention can further contain mobile hydrogen atoms, i.e. they can be present in various tautomeric forms. The present invention relates to all these tautomers.

The present invention further covers derivatives of the compounds of the formula I in which functional groups are masked or protected by suitable groups, for example by common protective groups. Such functional groups are, for example, carboxylic acid groups which can be present as ester groups or amide groups, or acylatable nitrogen containing groups which can be present as acyl derivatives. The present invention also covers other derivatives and prodrugs of the compounds of the formula I which may be designed in order to enhance the property profile of the compounds of the formula I and which may be prepared according to techniques well known to one skilled in the art, and it covers active metabolites of the compounds of the formula I.

A specific group of compounds of the formula I is formed by those compounds wherein two of the residues $R^{1a}$, $R^{1b}$, $R^{1c}$ and $R^{1d}$ independently of each other are hydrogen, F, Cl, Br, I, $(C^1-C_4)$-alkyl, $CF_3$, phenyl, phenyl-$(C_1-C_4)$-alkyl-, $(C_1-C_4)$-alkoxy, phenyloxy-, phenyl-$(C_1-C_4)$-alkoxy-, OH, $NO_2$, —$NR^{5a}R^{5b}$, —$NR^{5b}$—$SO_2$—$R^{6a}$, —S—$R^{6b}$, —$SO_n$—$R^{6c}$ where n is 1 or 2, —$SO_2$—$NR^{5a}R^{5b}$, —CN or —CO—$R^7$, and the other two of the residues $R^{1a}$, $R^{1b}$, $R^{1c}$ and $R^{1d}$ are hydrogen;

$R^{5a}$ is hydrogen, $(C_1-C_4)$-alkyl, phenyl, phenyl-$(C_1-C_4)$-alkyl-, formyl, (($C_1-C_4$)-alkyl)carbonyl-, phenylcarbonyl-, phenyl-(($C_1$–$C_4$)-alkyl)carbonyl-, (($C_1$–$C_4$)-alkoxy)carbonyl- or phenyl-(($C_1$–$C_4$)-alkoxy)carbonyl-;

$R^{5b}$ is hydrogen, ($C_1$–$C_4$)-alkyl, phenyl or phenyl-($C_1$–$C_4$)-alkyl-;

$R^{6a}$ is ($C_1$–$C_4$)-alkyl, phenyl, phenyl-($C_1$–$C_4$)-alkyl- or phenyl-NH—;

$R^{6b}$ is ($C_1$–$C_4$)-alkyl, phenyl or phenyl-($C_1$–$C_4$)-alkyl-;

$R^{6c}$ is hydroxy, ($C_1$–$C_4$)-alkyl, phenyl or phenyl-($C_1$–$C_4$)-alkyl-;

$R^7$ is hydroxy, ($C_1$–$C_4$)-alkoxy, phenyl-($C_1$–$C_4$)-alkoxy- or —$NR^{5a}R^{5b}$;

where all residues $R^{5a}$, $R^{5b}$, $R^{6a}$, $R^{6b}$, $R^{6c}$ and $R^7$ if present more than one time in the molecule, are independent of one another and can each be identical or different;

phenyl present in the residues $R^{1a}$, $R^{1b}$, $R^{1c}$, $R^{1d}$, $R^{5a}$, $R^{5b}$, $R^{6a}$, $R^{6b}$, $R^{6c}$ and $R^7$ denotes an unsubstituted phenyl residue or a phenyl residue which is substituted by one or two substituents selected from the series consisting of ($C_1$–$C_4$)-alkyl, F, Cl, Br, $CF_3$, ($C_1$–$C_4$)-alkoxy, $NO_2$, OH, $NH_2$ and CN;

one of the residues $R^2$ and $R^3$ is —$(CH_2)_p$—CO—$R^8$ and the other is hydrogen, F, Cl, Br, ($C_1$–$C_4$)-alkyl or —$(CH_2)_p$—CO—$R^8$, or $R^2$ and $R^3$ together form a group of the formula —$CH_2$—$CH_2$—N(—CO—$R^{20}$)—$CH_2$— wherein $R^{20}$ is phenyl, phenyl-($C_1$–$C_4$)-alkyl-, pyridyl or pyridyl-($C_1$–$C_4$)-alkyl- and where each phenyl residue is unsubstituted or substituted by $R^{15a}$ and each pyridyl residue is unsubstituted or substituted at the nitrogen atom by $R^{14}$;

p is 0, 1 or 2;

$R^8$ is —$NR^9R^{10}$ or —$OR^{10}$, where residues $R^8$ if present more than one time in the molecule, are independent of each other and can be identical or different;

$R^9$ is hydrogen, ($C_1$–$C_4$)-alkyl-, hydroxycarbonyl-($C_1$–$C_4$)-alkyl-, (($C_1$–$C_4$)-alkoxy)carbonyl-($C_1$–$C_4$)-alkyl- or aminocarbonyl-($C_1$–$C_4$)-alkyl-;

$R^{10}$ is hydrogen, ($C_1$–$C_8$)-alkyl-, phenyl, naphthyl, phenyl-($C_1$–$C_4$)-alkyl-, naphthyl-($C_1$–$C_4$)-alkyl-, pyridyl or the residue Het, where the ($C_1$–$C_8$)-alkyl-residue residue and each phenyl and naphthyl residue is unsubstituted or substituted by one or two identical or different residues $R^{11}$, and where the pyridyl residue is unsubstituted or substituted at the nitrogen atom by $R^{14}$, and where Het is unsubstituted or substituted by $R^{15a}$;

or $R^9$ and $R^{10}$ together with the nitrogen atom to which they are bonded form a 5-membered or 6-membered saturated heterocyclic ring which can contain an additional nitrogen atom in the ring and which is unsubstituted or substituted by $R^{15a}$ or by —CO—$R^7$;

Het is the residue of a 5-membered or 6-membered saturated heterocyclic ring containing 1 or 2 identical or different ring heteroatoms selected from the series consisting of nitrogen, oxygen and sulfur;

$R^{11}$ is —$NHR^{12}$, —$OR^{12}$, —CO—$N(R^{13})_2$, —CO—$R^7$, $R^{15b}$, cyclohexyl, phenyl which is unsubstituted or substituted by $R^{15b}$, naphthyl which is unsubstituted or substituted by $R^{15b}$, pyridyl which is unsubstituted or substituted at the nitrogen atom by $R^{14}$, or Het which is unsubstituted or substituted by $R^{15a}$, where residues $R^{11}$ if present more than one time in the molecule, are independent of each other and can be identical or different;

$R^{12}$ is hydrogen, pyrrolidinyl, piperidinyl, pyrrolidinyl-($C_1$–$C_4$)-alkyl- or piperidinyl-($C_1$–$C_4$)-alkyl-, where each pyrrolidinyl residue and each piperidinyl residue is unsubstituted or substituted at the nitrogen atom by phenyl-($C_1$–$C_4$)-alkyl- or $R^{15a}$;

each residue $R^{13}$ independently of the denotation of another residue $R^{13}$ is hydrogen, ($C_1$–$C_4$)-alkyl or phenyl-($C_1$–$C_4$)-alkyl-, or the two residues $R^{13}$ together with the nitrogen atom to which they are bonded form a 5-membered or 6-membered saturated heterocyclic ring which can contain an additional nitrogen atom or oxygen atom in the ring where the additional nitrogen atom in the ring is unsubstituted or substituted by ($C_1$–$C_4$)-alkyl or phenyl-($C_1$–$C_4$)-alkyl-;

$R^{14}$ is ($C_1$–$C_6$)-alkyl, ($C_1$–$C_6$)-alkenyl, ($C_1$–$C_6$)-alkynyl, phenyl-($C_1$–$C_6$)-alkyl or (($C_1$–$C_6$)-alkoxy)carbonyl-($C_1$–$C_6$)-alkyl-, where phenyl present in $R^{14}$ denotes an unsubstituted phenyl residue, the substitution by these residues at the nitrogen atom of the pyridyl residue leading to a pyridinium group having $X^-$ as the counterion; or $R^{14}$ is oxido this substitution at the nitrogen atom of the pyridyl residue leading to a pyridine N-oxide; and where residues $R^{14}$ if present more than one time in the molecule, are independent of each other and can be identical or different;

$R^{15a}$ is ($C_1$–$C_6$)-alkyl, (($C_1$–$C_6$)-alkyl)-C(=NH)—, —$(CH_2)_t$—$N(R^{16})_2$, —$(CH_2)_t$—$N^+(R^{16a})_2(-O^-)$, —$(CH_2)_t$—$N^+(R^{16a})_3X^-$, —$(CH_2)_t$—$NHR^{17}$, —$(CH_2)_t$—CN, —$(CH_2)_t$—CS—$N(R^{18})_2$, —$(CH_2)_t$—C(=$NR^{17}$)—$NHR^{17}$ or —$(CH_2)_t$—NH—C(=$NR^{17}$)—$NHR^{17}$, where (($C_1$–$C_6$)-alkyl)-C(=NH)— is bonded to a ring nitrogen atom, and where residues $R^{15a}$ if present more than one time in the molecule, are independent of each other and can be identical or different;

$R^{15b}$ is ($C_1$–$C_6$)-alkyl, hydroxy, F, Cl, Br, —$(CH_2)$, —$N(R^{16})_2$, —$(CH_2)_t$—$N^+(R^{16a})_2(-O^-)$ —$(CH_2)_t$—$N^+(R^{16a})_3X^-$, —$(CH_2)_t$—$NHR^{17}$, —$(CH_2)_t$—CN, —$(CH_2)_t$—CS—$N(R^{18})_2$, —$(CH_2)_t$—C(=$NR^{17}$)—$NHR^{17}$ or —$(CH_2)_t$—NH—C(=$NR^{17}$)—$NHR^{17}$, where residues $R^{15b}$ if present more than one time in the molecule, are independent of each other and can be identical or different;

t is 0, 1, 2 or 3, where numbers t, if present more than one time in the molecule, are independent of each other and can be identical or different;

each residue $R^{16}$ independently of the denotations of another residue $R^{16}$ is hydrogen, ($C_1$–$C_6$)-alkyl, ($C_1$–$C_6$)-alkenyl, ($C_1$–$C_6$)-alkynyl, phenyl-($C_1$–$C_6$)-alkyl- or (($C_1$–$C_6$)-alkoxy)carbonyl-($C_1$–$C_6$)-alkyl-, where phenyl present in $R^{16}$ denotes an unsubstituted phenyl residue, and where groups containing residues $R^{16}$ if present more than one time in the molecule, are independent of each other and can be identical or different;

each residue $R^{16a}$ independently of the denotations of another residue $R^{16a}$ is ($C_1$–$C_6$)-alkyl, ($C_1$–$C_6$)-alkenyl, ($C_1$–$C_6$)-alkynyl, phenyl-($C_1$–$C_6$)-alkyl- or (($C_1$–$C_6$)-alkoxy)carbonyl-($C_1$–$C_6$)-alkyl-, where phenyl present in $R^{16a}$ denotes an unsubstituted phenyl residue, and where groups containing residues $R^{16a}$ if present more than one time in the molecule, are independent of each other and can be identical or different;

each residue $R^{17}$ independently of the denotation of another residue $R^{17}$ is hydrogen, ($C_1$–$C_6$)-alkyl, ($C_1$–$C_6$)-alkylcarbonyl-, ($C_1$–$C_6$)-alkoxycarbonyl-, ($C_1$–$C_6$)-alkylcarbonyloxy-($C_1$–$C_6$)-alkoxycarbonyl-, phenylcarbonyl-, phenoxycarbonyl-, phenyl-$(C_1-C_6)$-alkoxycarbonyl-, hydroxy, $(C_1-C_6)$-alkoxy, phenyl-$(C_1-C_6)$-alkoxy- or amino, and additionally in the groups —$(CH_2)_t$—$C(=NR^{17})$—$NHR^{17}$ and —$(CH_2)_t$—NH—$C(=NR^{17})$—$NHR^{17}$ the two residues $R^{17}$ together with the $C(=N)$—NH group to which they are bonded, can form a 5-membered or 6-membered heterocyclic ring, and were phenyl present in $R^{17}$ denotes an unsubstituted phenyl residue, and where groups containing residues $R^{17}$ if present more than one time in the molecule, are independent of each other and can be identical or different;

each residue $R^{18}$ independently of the denotation of another residue $R^{18}$ is hydrogen or $(C_1-C_4)$-alkyl;

A is a direct linkage, —$(C_1-C_4)$-alkyl- which is saturated or which contains a double bond or a triple bond, —CO—, —$SO_r$— wherein r is 1 or 2, —CO—$(C_1-C_4)$-alkyl-, —$(C_1-C_4)$-alkyl-CO— or —$(C_1-C_4)$-alkyl-CO—NH— wherein the nitrogen is bonded to $R^4$;

$R^4$ is phenyl which is substituted by $R^{15c}$ and which additionally can be substituted by one or two substituents from the series consisting of $(C_1-C_4)$-alkyl, F, Cl and Br, or $R^4$ is pyridyl which is unsubstituted or substituted at the nitrogen atom by $R^{14}$, or $R^4$ is the residue Het which is substituted by $R^{15d}$;

$R^{15c}$ is —$(CH_2)_t$—$N(R^{16})_2$, —$(CH_2)_t$—$N^+(R^{16a})_2(—O^-)$, —$(CH_2)_t$—$N^+(R^{16a})_3 X^-$, —$(CH_2)_t$—$NHR^{17}$, —$(CH_2)_t$—CN, —$(CH_2)_t$—CS—$N(R^{18})_2$, —$(CH_2)_t$—$C(=NR^{17})$—$NHR^{17}$ or —$(CH_2)_t$—NH—$C(=NR^{17})$—$NHR^{17}$;

$R^{15d}$ is $((C_1-C_6)$-alkyl$)$-$C(=NH)$—, —$(CH_2)_t$—$N(R^{16})_2$, —$(CH_2)_t$—$N^+(R^{16a})_2(—O^-)$, —$(CH_2)_t$—$N^+(R^{16a})_3 X^-$, —$(CH_2)_t$—$NHR^{17}$, —$(CH_2)_t$—CN, —$(CH_2)_t$—CS—$N(R^{18})_2$, —$(CH_2)_t$—$C(=NR^{17})$—$NHR^{17}$ or —$(CH_2)_t$—NH—$C(=NR^{17})$—$NHR^{17}$, where $((C_1-C_6)$-alkyl$)$-$C(=NH)$— is bonded to a ring nitrogen atom;

$X^-$ is a physiologically acceptable anion;

in all their stereoisomeric forms and mixtures thereof in any ratio, and their physiologically acceptable salts.

As with any group of structurally related compounds which possess a particular generic utility, certain groups and configurations are preferred for compounds of the formula I in their end-use application.

Preferred compounds of the formula I are those wherein the residues $R^{1a}$, $R^{1b}$, $R^{1c}$ and $R^{1d}$ independently of one another are selected from the series consisting of hydrogen, methyl, F, Cl, Br, I, hydroxy, $(C_1-C_4)$-alkoxy, phenyl-$(C_1-C_4)$-alkoxy- and —$NR^{5a}R^{5b}$, in particular from the series consisting of hydrogen, methyl, F, Br, hydroxy, methoxy, benzyloxy and —$NHR^{5a}$.

Preferred compounds of the formula I are also those wherein three or all four of the residues $R^{1a}$, $R^{1b}$, $R^{1c}$ and $R^{1d}$ are hydrogen. Preferred compounds of the formula I are also those wherein the residues $R^{1c}$ and $R^{1d}$ are hydrogen.

Preferred compounds of the formula I are also those wherein the residues $R^{1a}$ and $R^{1b}$ are hydrogen or one or two of the residues $R^{1a}$ and $R^{1b}$ are different from hydrogen. Particularly preferred compounds of the formula I are those wherein one of the residues $R^{1a}$ and $R^{1b}$ is hydrogen and the other of the residues $R^{1a}$ and $R^{1b}$ is hydrogen or is different from hydrogen. Especially preferred are compounds of the formula I wherein one of the residues $R^{1a}$ and $R^{1b}$ is selected from the series consisting of hydrogen, methyl, F, Br, hydroxy, methoxy, benzyloxy and —$NHR^{5a}$ and the other of the residues $R^{1a}$ and $R^{1b}$ as well as the residues $R^{1c}$ and $R^{1d}$ are hydrogen.

Preferred compounds of the formula I are also those wherein the residue $R^{5a}$ is hydrogen or $((C_1-C_4)$-alkoxy$)$carbonyl-, in particular hydrogen or tert-butyloxycarbonyl.

Preferred compounds of the formula I are also those wherein the residue $R^{5b}$ is hydrogen.

Preferred compounds of the formula I are also those wherein one of the residues $R^2$ and $R^3$ is —$(CH_2)_p$—CO—$R^8$ and the other is hydrogen, F, Cl, Br, $(C_1-C_4)$-alkyl or —$(CH_2)_p$—CO—$R^8$. Particularly preferred compounds of the formula I are those wherein $R^3$ is —$(CH_2)_p$—CO—$R^8$, very particularly —CO—$R^8$. Particularly preferred compounds of the formula I are also those wherein $R^2$ is hydrogen, Cl or Br. Especially preferred compounds of the formula I are those wherein $R^2$ is hydrogen, Cl or Br and $R^3$ is —$(CH_2)_p$—CO—$R^8$, in particular $R^3$ is -CO-$R^8$.

Preferred compounds of the formula I are also those wherein p is 0 or 1, in particular 0.

Preferred compounds of the formula I are also those wherein $R^8$ is —$NR^9R^{10}$ or —$OR^{10}$, in particular —$NR^9R^{10}$.

Preferred compounds of the formula I are also those wherein $R^9$ is hydrogen.

Particularly preferred compounds of the formula I are those wherein $R_2$ is hydrogen, Cl or Br and $R^3$ is —CO—$NR^9R^{10}$ or —CO—$OR^{10}$, especially $R^3$ is —CO—$NR^9R^{10}$, more especially $R^3$ is —CO—$NHR^{10}$.

Preferred compounds of the formula I are also those wherein $R^{10}$ is $(C_1-C_{10})$-alkyl, phenyl-$(C_1-C_4)$-alkyl- or naphthyl-$(C_1-C_4)$-alkyl-, where the $(C_1-C_{10})$-alkyl residue, the phenyl residue and the naphthyl residue are unsubstituted or substituted by one, two or three identical or different residues $R^{11}$, and particularly the $(C_1-C_{10})$-alkyl residue and the phenyl residue are substituted by one, two or three identical or different residues $R^{11}$ and the naphthyl residue is unsubstituted or substituted by one, two or three identical or different residues $R^{11}$, and more particularly the $(C_1-C_{10})$-alkyl residue and the phenyl residue are substituted by one, two or three identical or different residues $R^{11}$ and the naphthyl residue is unsubstituted.

Preferred compounds of the formula I are also those wherein $R^{11}$ is $R^{15b}$, $(C_1-C_{14})$-alkyl, quinolinyl, isoquinolinyl or pyridyl, where quinolinyl, isoquinolinyl, and pyridyl are unsubstituted or substituted at the nitrogen atom by $R^{14}$. A $(C_1-C_4)$-alkyl residue representing $R^{11}$ preferably has up to 12, more preferably up to 10 carbon atoms.

Preferred compounds of the formula I are also those wherein $R^{14}$ is $(C_1-C_6)$-alkyl.

Preferred compounds of the formula I are also those wherein $R^{15b}$ is $(C_1-C_6)$-alkyl where the alkyl residue can be substituted 1, 2, 3, 4, 5, 6 or 7 times by fluoro, or $R^{15b}$ is F, Cl, I, —$(CH_2)_t$—$N^+(R^{16a})_3 X^-$ or —$(CH_2)_t$—$C(=NR^{17})$—$NHR^{17}$.

Preferred compounds of the formula I are also those wherein t is 0 or 1, in particular 0, where numbers t, if present more than one time in the molecule, are independent of each other and are identical or different.

Preferred compounds of the formula I are also those wherein $R^{16a}$ is $(C_1-C_6)$-alkyl, $(C_1-C_6)$-alkynyl or phenyl-$(C_1-C_6)$-alkyl.

Preferred compounds of the formula I are also those wherein $R^{17}$ is hydrogen.

Preferred compounds of the formula I are also those wherein A is a divalent —$(C_1-C_4)$-alkyl- residue, in particular a divalent —$(C_1-C_4)$-alkyl- residue which is saturated. Particulary preferred compounds of the formula I are those wherein A is the methylene residue —$CH_2$—.

Preferred compounds of the formula I are also those wherein $R^4$ is phenyl which is substituted by one residue $R^{15c}$ and which can additionally be substituted by one or two substituents from the series consisting of $(C_1-C_4)$-alkyl, F, Cl and Br, or $R^4$ is pyridyl which is unsubstituted or substituted at the nitrogen atom by $R^{14}$. Particularly preferred compounds of the formula I are also those wherein $R^4$ is phenyl which is substituted by one residue $R^{15c}$, especially by one residue $R^{15c}$ in the meta position or the para position.

Preferred compounds of the formula I are also those wherein $R^{15c}$ is —$(CH_2)_t$—C(=NR$^{17}$)—NHR$^{17}$, in particular —C(=NR$^{17}$)—NHR$^{17}$. Moreover preferred are compounds wherein $R^{15c}$ is —$(CH_2)_t$—C(=NH)—NH$_2$, in particular —C(=NH)—NH$_2$.

Particularly preferred compounds of the formula I are those wherein $R^4$ is phenyl which is substituted by —C(=NR$^{17}$)—NHR$^{17}$, especially those compounds of the formula I wherein $R^4$ is phenyl which is substituted by —C(=NR$^{17}$)—NHR$^{17}$ in the meta position or the para position, moreover preferred those substituted in the meta position. A preferred denotation of the residue $R^{17}$ present in such groups $R^4$ is hydrogen.

Especially preferred compounds of the formula I are those wherein two or more residues are defined as indicated before for preferred compounds of the formula I, or residues can have one or some of the specific denotations of the residues given in their general definitions or in the definitions of preferred compounds before. All possible combinations of definitions given for preferred definitions and of specific denotations of residues explicitly are a subject of the present invention.

Also with respect to all preferred compounds of the formula I all their stereoisomeric forms and mixtures thereof in any ratio and their physiologically acceptable salts explicitly are a subject of the present invention, as well as are their prodrugs. Similarly, also in all preferred compounds of the formula I all residues that are present more than one time in the molecule are independent of each other and can be identical or different.

The compounds of the formula I can be prepared by utilizing procedures and techniques which per se are well known and appreciated by one of ordinary skill in the art. Starting materials or building blocks for use in the general synthetic procedures that can be applied in the preparation of the compounds of formula I are readily available to one of ordinary skill in the art. In many cases they are commercially available or have been described in the literature. Otherwise they can be prepared from readily available precursor compounds analogously to procedures described in the literature, or by procedures or analogously to procedures described in this application.

In general, compounds of the formula I can be prepared, for example in the course of a convergent synthesis, by linking two or more fragments which can be derived retrosynthetically from the formula I. More specifically, suitably substituted starting indole derivatives are employed as building blocks in the preparation of the compounds of formula I. If not commercially available such indole derivatives can be prepared according to the well-known standard procedures for the formation of the indole ring system such as, for example, the Fischer indole synthesis, the Madelung indole synthesis, the indole synthesis starting from N-chloroanilines and β-ketosulfides described by Gassman et al., the Bischler indole synthesis, the Reissert indole synthesis, or the Nenitzescu indole synthesis. By choosing suitable precursor molecules, these indole syntheses allow the introduction of a variety of substituents into the various positions of the indole system which can then be chemically modified in order to finally arrive at the molecule of the formula I having the desired substituent pattern. As one of the comprehensive reviews in which numerous details and literature references on the chemistry of indoles and on synthetic procedures for their preparation can be found, volume 25, "Indoles, Part One", W. J. Houlihan (ed.), 1972, out of the series "The Chemistry of Heterocyclic Compounds", A. Weissberger and E. C. Taylor (ed.), John Wiley & Sons, is referred to.

Examples of the many commercially available indole derivatives that are suitable as starting materials for the preparation of the compounds of formula I, are the following (the acids listed are commercially available as the free acids themselves and/or as the methyl or ethyl esters): indole-2-carboxylic acid, indole-3-carboxylic acid, indole-3-acetic acid, 3-(3-indolyl)-propionic acid, indole-2,3-dicarboxylic acid, 3-ethoxycarbonylmethyl-indole-2-carboxylic acid, 3-methyl-indole-2-carboxylic acid, 5-fluoroindole-2-carboxylic acid, 5-chloro-indole-2-carboxylic acid, 5-bromo-indole-2-carboxylic acid, 5-methoxy-indole-2-carboxylic acid, 5-hydroxy-indole-2-carboxylic acid, 5,6-dimethoxy-indole-2-carboxylic caid, 4-benzyloxy-indole-2-carboxylic acid, 5-benzyloxy-indole-2-carboxylic acid, 6-benzyloxy-5-methoxy-indole-2-carboxylic acid, 5-methyl-indole-2-carboxylic acid, 5-ethyl-indole-2-carboxylic acid, 7-methyl-indole-2-carboxylic acid, 4-methoxy-indole-2-carboxylic acid, 6-methoxy-indole-2-carboxylic acid, 4,6-dimethoxy-indole-2-carboxylic acid, 4,6-dichloro-indole-2-carboxylic acid, 5-nitro-indole-2-carboxylic acid, 5-methylsulfonyl-indole-2-carboxylic acid, 7-nitro-indole-2-carboxylic acid, 7-tert-butylcarbonylamino-indole-2-carboxylic acid, 7-(3-trifluoro-methylbenzoylamino)-indole-2-carboxylic acid, 7-(4-methoxyphenylsulfonylamino)-indole-2-carboxylic acid, 5-bromo-3-methyl-indole-2-carboxylic acid, 3-(2-carboxyethyl)-6-chloroindole-2-carboxylic acid.

If starting indole derivatives are to be synthesized this can be done, for example, according to the well known indole syntheses mentioned above. In the following they are explained briefly, however, they are standard procedures comprehensively discussed in the literature, and are well known to one skilled in the art.

The Fischer indole synthesis comprises the acid cyclization of phenylhydrazones, for example of the general formula II,

II

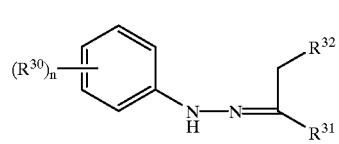

which can be obtained by various methods and in which $R^{30}$, $R^{31}$ and $R^{32}$ and n can have a wide variety of denotations. Besides hydrogen and alkyl, $R^{31}$ and $R^{32}$ can especially denote ester groups or methyl or ethyl groups carrying an ester group as substituent thus allowing the introduction into the indole molecule of the $(CH_2)_p$—CO moiety occurring in the groups $R^2$ and/or $R^3$ in the compounds of the formula I. As examples of the many literature references describing the synthesis of indole derivatives according to the Fischer synthesis, besides the above-mentioned book edited by Houlihan, the following articles are mentioned: F. G. Salituro et al., J. Med. Chem. 33 (1990), 2944; N. M. Gray et al., J. Med. Chem. 34 (1991); 1283; J. Sh. Chikvaidze et al., Khim. Geterotsikl. Soedin. (1991), 1508; S. P. Hiremath et al., Indian J. Chem. 19 (1980), 770; J. Bornstein, J. Amer. Chem. Soc. 79 (1957), 1745.

The Reissert indole synthesis comprises the reductive cyclization of o-nitrophenylpyruvic acids or esters therof, for example of the general formula

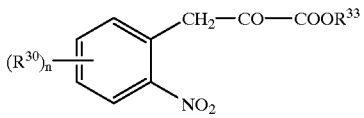

III in which the groups $R^{30}$ can have a wide variety of denotations and can be present in all positions of the benzene ring. The Reissert indole synthesis leads to derivatives of indole-2-carboxylic acids. The pyruvic acid derivatives of the formula III can be obtained by condensation of oxalic acid esters with substituted o-nitrotoluenes. As literature references, besides the above-mentioned book edited by Houlihan and the literature articles mentioned therein, for example the articles by H. G. Lindwall and G. J. Mantell, J. Org. Chem. 18 (1953), 345 or by H. Burton and J. L. Stoves, J. Chem. Soc. (1937), 1726 are mentioned.

According to the Bischler indole synthesis α-anilinoketones, for example of the general formula IV,

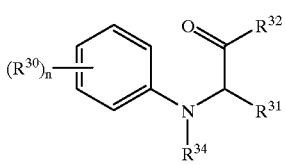

IV can be cyclized to indole derivatives.

The Nenitzescu indole synthesis provides a valuable route to indole-3-carboxylic acid derivatives carrying a hydroxy group in the 5-position. It comprises the reaction of a para-benzoquinone with a β-aminocrotonate, for example of the compounds of the formulae V and VI.

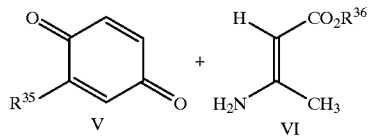

A further route to specifically substituted indole derivatives proceeds via 2,3-dihydroindoles (indolines) which can be easily obtained by reduction of indoles, for example by hydrogenation, or by cyclization of suitable phenylethylamine derivatives. Indolines can undergo a variety of electrophilic aromatic substitution reaction allowing the introduction of various substituents into the benzene nucleus which cannot directly be introduced by such reactions into the benzene nucleus of the indole molecule. The indolines can then be dehydrogenated to the corresponding indoles, for example with reagents like chloranil or palladium together with a hydrogen acceptor. Again, details on these syntheses can be found in the above-mentioned book edited by Houlihan.

Depending on the substituents in the starting materials, in certain indole syntheses mixtures of positional isomers may be obtained which, however, can be separated by modern separation techniques like, for example, preparative HPLC.

Further, in order to obtain the desired substituents in the benzene nucleus and in the heterocyclic nucleus of the indole ring system in the formula I, the functional groups introduced into the ring system during the indole synthesis can be chemically modified. For example, indoles carrying a hydrogen atom in the 2-position or the 3-position can also be obtained by saponification and subsequent decarboxylation of indoles carrying an ester group in the respective position. Carboxylic acid groups and acetic acid groups in the 2-position and the 3-position can be converted into their homologues by usual reactions for chain elongation of carboxylic acids. Halogen atoms can be introduced into the 2-position or the 3-position, for example by reacting the respective indolinone with a halogenating agent such as phosphorus pentachloride analogously to the method described by J. C. Powers, J. Org. Chem. 31 (1966), 2627. The starting indolinones for such a synthesis can be obtained from 2-aminophenyl acetic acids. Starting indole derivatives for the preparation of compounds of the formula I carrying a halogen substituent in the 3-position can also be obtained according to procedures described in the literature like the following. Chlorination of 1H-indole-2-carboxylic acid ethyl ester in the 3-position by reaction with sulfuryl chloride in benzene yields 3-chloro-1H-indole-2-carboxylic acid ethyl ester (Chem. Abstr. 1962, 3441i–3442b). 3-Bromo-1-(3-cyano-benzyl)-1H-indole-2-carboxylic acid ethyl ester can be synthesized analogously to J. Het. Chem 33 (1996), 1627 by reaction of 1-(3-cyano-benzyl)-1H-indole-2-carboxylic acid ethyl ester with pyridinium bromide perbromide in pyridine.

Especially the groups present in the benzene nucleus of the indole ring system can be modified by a variety of reactions and thus the desired residues $R^{1a}$, $R^{1b}$, $R^{1c}$ and $R^{1d}$ be obtained. For example, nitro groups can be reduced to amino group with various reducing agents, such as sulfides, dithionites, complex hydrides or by catalytic hydrogenation. A reduction of a nitro group may also be carried out at a later stage of the synthesis of a compound of the formula I, and a reduction of a nitro group to an amino group may also occur simultaneously with a reaction performed on another functional group, for example when reacting a group like a cyano group with hydrogen sulfide or when hydrogenating a group. In order to introduce the residues $R^{5a}$, $R^{5b}$ and $R^{6a}$—$SO_2$, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivates such as acid chlorides, anhydrides, activated esters or others or by reaction with carboxylic acids in the presence of an activating agent, or according to standard procedures for sulfonylation, for example by reaction with sulfonyl chlorides.

Ester groups present in the benzene nucleus can be hydrolyzed to the corresponding carboxylic acids which after activation can then be reacted with amines or alcohols under standard conditions. Ether groups present at the benzene nucleus, for example benzyloxy groups or other easily cleavable ether groups, can be cleaved to give hydroxy groups which then can be reacted with a variety of agents, for example etherification agents or activating agents allowing replacement of the hydroxy group by other groups. Sulfur-containing groups can be reacted accordingly.

The before-mentioned reactions for the conversion of functional groups are in general extensively described in textbooks of organic chemistry and in treatises like Houben-Weyl, "Methoden der Organischen Chemie" (Methods of Organic Chemistry), Georg Thieme Verlag, Stuttgart, Germany, or "Organic Reactions", John Wiley & Sons, New York, in which details on the reactions and primary source literature can be found. Due to the fact that in the present case the functional groups are attached to an indole ring it may in certain cases become necessary to specifically adapt reaction conditions or to choose specific reagents from a variety of reagents that can in principle be employed into a conversion reaction, or otherwise to take specific measures for achieving a desired conversion, for example to use protection group techniques. However, finding out suitable reaction variants and reaction conditions in such cases does not cause any problems for one skilled in the art.

The structural elements present in the residues in the 1-position of the indole ring in the compounds of the formula I and in the $COR^8$ group present in the 2-position and/or in the 3-position of the indole ring can be introduced into the starting indole derivative obtainable as outlined above by consecutive reaction steps like those outlines below using procedures which per se are well known to one skilled in the art.

The residues $R^8$ that can be present in $R^2$ and/or $R^3$ can be introduced, for example, by condensing a corresponding carboxylic acid of the formula VII or a derivative thereof with a compound or with compounds of the formula $HR^{8'}$, i.e. with an amine of the formula $HNR^{9'}R^{10'}$ and/or with an alcohol of the formula $HOR^{10'}$ and/or with a mercaptan of the formula $HS$—$(C_1$–$C_4)$-alkyl to give a compound of the formula VIII. The compound of the formula VIII thus obtained can already contain the desired final groups, i.e. the groups $R^8$ and $R^{40}$ can be the groups $R^8$ and $R^4$—A— defined as for the formula I, or optionally in the compound of the formula VIII thus obtained subsequently the residue or the residues $R^{8'}$ and the residue $R^{40}$ are converted into the residues $R^8$ and $R^4$—A—, respectively, to give the desired compound of the formula I.

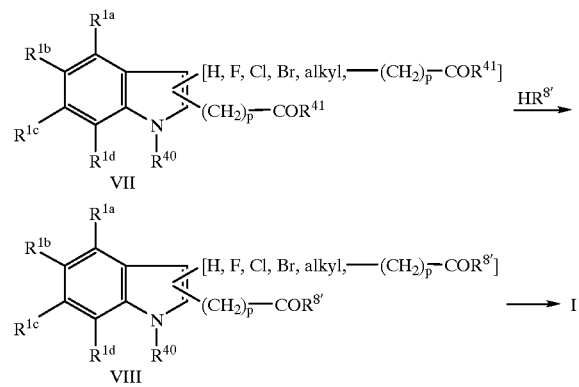

Thus, the residues $R^{8'}$ and the residues $R^{9'}$ and $R^{10'}$ contained therein can have the denotations of $R^8$, $R^9$ and $R^{10}$, respectively, given above or in addition in the residues $R^{8'}$, $R^{9'}$ and $R^{1'}$ functional groups can also be present in the form of groups that can subsequently be transformed into the final groups $R^8$, $R^9$ and $R^{10}$, i.e. functional groups can be present in the form of precursor groups or of derivatives, for example in protected form. Examples of precursor groups are cyano groups which may in a later step be transformed into carboxylic acid derivatives or by reduction into aminomethyl groups, or nitro groups which may be transformed by reduction like catalytic hydrogenation into amino groups.

The residue $R^{40}$ in the compounds of the formulae VII and VIII can denote the group —A—$R^4$ as defined above which finally is to be present in the desired target molecule of the formula I, or it can denote a group which can subsequently be transformed into the group —A—$R^4$, for example a precursor group or a derivative of the group —A—$R^4$ in which functional groups are present in protected form, or $R^{40}$ can denote a hydrogen atom or a protective group for the nitrogen atom of the indole ring. Similarly, the residues $R^{1a}$, $R^{1b}$, $R^{1c}$ and $R^{1d}$ and the numbers p in the formulae VII and VIII are defined as above, however, for the synthesis of the compounds of the formula I these residues, too, can in principle be present at the stage of the condensation of a compound of the formula VII with a compound of the formula $HR^{8'}$ giving a compound of the formula VIII in the form of precursor groups or in protected form.

The residues $R^{41}$ in the compounds of the formula VII which can be identical or different, can be, for example, hydroxy or $(C_1$–$C_4)$-alkoxy, i.e., the groups $COR^{41}$ present in the compounds of the formula VII can be, for example, the free carboxylic acids or esters thereof like alkyl esters as can be the groups $COR^8$ in the compounds of the formula I. The groups $COR^{41}$ can also be any other activated derivative of a carboxylic acid which allows amide formation, ester formation or thioester formation with a compound of the formula $HR^{8'}$. The group $COR^{41}$ can be, for example, an acid chloride, an activated ester like a substituted phenyl ester, an azolide like an imidazolide, an azide or a mixed anhydride, for example a mixed anhydride with a carbonic acid ester or with a sulfonic acid, which derivatives can all be prepared from the carboxylic acid by standard procedures and can be reacted with an amine, an alcohol or a mercaptan of the formula $HR^{8'}$ under standard conditions. A carboxylic acid group COOH representing $COR^{41}$ in a compound of the formula VII can be obtained, for example, from an ester group introduced into the indole system during an indole synthesis by standard hydrolysis procedures.

Compounds of the formula I in which a group $COR^8$ is an ester group can also be prepared from compounds of the formula VII in which $COR^{41}$ is a carboxylic acid group by common esterification reactions like, for example, reacting the acid with an alcohol under acid catalysis, or alkylation of a salt of the carboxylic acid with an electrophile like an alkyl halogenide, or by transesterification from another ester. Compounds of the formula I in which a group $COR^8$ is an amide group can be prepared from amines and compounds of the formula VII in which $COR^{41}$ is a carboxylic acid group or an ester thereof by common amination reactions. Especially for the preparation of amides the compounds of the formula VII in which $COR^{41}$ is a carboxylic acid group can be condensed under standard conditions with compounds of the formula $HR^{8'}$ which are amines by means of common coupling reagents used in peptide synthesis. Such coupling reagents are, for example, carbodiimides like dicyclohexylcarbodiimide (DCC) or diisopropylcarbodiimide, carbonyidiazoles like carbonyidiimidazole and similar reagents, propylphosphonic anhydride, O-((cyano-(ethoxycarbonyl)-methylene)amino)-N,N,N',N'-tetramethyluronium tetrafluoroborate (TOTU) and many others.

If in the compounds of the formula VII two identical groups $COR^{41}$, for example two COOH groups, are present and only one of them is to be condensed with the compound $HR^{8'}$, or if the two groups are to be condensed with two different compounds $HR^{8'}$, the condensation reaction has to be suitably adapted. Such an adaption will not constitute a problem for one skilled in the art. As a reference discussing such reactions, for example, Y. Miki, H. Hachiken and I. Yoshikawa, Heterocycles 45 (1997), 1143 may be mentioned. The desired result can, for example, be achieved by using reagents and/or reaction conditions which allow a selective reaction of the two groups, or by applying a protective group strategy. In the latter case one of the groups is first selectively protected, for example by transformation into an appropriate ester or another protected form of a carboxylic acid, then the other group is condensed with the compound of the formula HR$^{8'}$, and then the first group is deprotected and, if desired, is reacted with a second compound of the formula HR$^{8'}$. Different groups COR$^{41}$, for example one ester group and one free carboxylic acid group may, however, also be initially present in the starting indole derivative of the formula VII employed into the condensation reaction.

If the residue R$^4$—A— present in an indole of the formula I or the residue R$^{40}$ present in an indole of the formula VII, or a residue in which functional groups within the residue R$^4$—A— or R$^{40}$ are present in protected form or in the form of a precursor group, have not already been introduced during a preceding step, for example during a synthesis of the indole nucleus, these residues can, for example, be introduced into the 1-position of the indole system by conventional literature procedures well known to one skilled in the art for N-alkylation, N-arylation, N-acylation or N-sulfonylation of ring nitrogen atoms of heterocycles. The starting indole derivative that is to be employed in such a reaction carries a hydrogen atom in the 1-position. N-Alkylation of a ring nitrogen atom can, for example, be performed under standard conditions, preferably in the presence of a base, using an alkylating compound of the formula R$^4$—A—LG or of the formula R$^{40}$—LG, wherein the atom in the group A or in the group R$^{40}$ bonded to the group LG in this case is an aliphatic carbon atom of an alkyl moiety and LG is a leaving group, for example halogen like chlorine, bromine or iodine, or a sulfonyloxy group like tosyloxy, mesyloxy or trifluormethylsulfonyloxy. LG may, for example, also be a hydroxy group which, in order to achieve the alkylation reaction, is activated by a conventional activating agent. For the preparation of compounds in which A is a direct linkage and an aromatic group is directly bonded to the 1-position of the indole system, conventional arylation procedures can be used. For example aryl fluorides like nitroaryl fluorides or cyanoaryl fluorides can be employed as arylating agents which advantageously allow the subsequent formation of an amino group. Such processes are described, for example, in Tetrahedron Lett. 37 (1996), 299; Tetrahedron Lett. 36 (1995), 8387; Synth. Commun. 25 (1995), 2165; J. Med. Chem. 28 (1985), 66.

A guanidino function present in a compound of the formula I can be introduced by conversion of an amino function which, for example, may be obtained by reduction of a nitro function or a cyano function, using the following reagents:

1. O-Methylisourea (S. Weiss and H. Krommer, Chemiker-Zeitung 98 (1974), 617–618)
2. S-Methylisothiourea (R. F. Borne, M. L. Forrester and I. W. Waters, J. Med. Chem. 20 (1977), 771–776)
3. Nitro-S-methylisothiourea (L. S. Hafner and R. E. Evans, J. Org. Chem. 24 (1959), 1157)
4. Formamidinosulfonic acid (K. Kim, Y.-T. Lin and H. S. Mosher, Tetra. Lett. 29 (1988), 3183–3186)
5. 3,5-Dimethyl-1-pyrazolylformamidinium nitrate (F. L. Scott, D. G. O'Donovan and J. Reilly, J. Amer. Chem. Soc. 75 (1953), 4053–4054)
6. N,N'-Di-tert-butyloxycarbonyl-S-methylisothiourea (R. J. Bergeron and J. S. McManis, J. Org. Chem. 52 (1987), 1700–1703)
7. N-Alkoxycarbonyl-, N,N'-dialkoxycarbonyl-, N-alkylcarbonyl- and N,N'-dialkylcarbonyl-S-methylisothiourea (H. Wollweber, H. Kölling, E. Niemers, A. Widdig, P. Andrews, H.-P. Schulz and H. Thomas, Arzneim. Forsch./Drug Res. 34 (1984), 531–542).

Amidines can be prepared from the corresponding cyano compounds by addition of alcohols, for example methanol or ethanol, in an acidic anhydrous medium, for example dioxane, methanol or ethanol, and subsequent aminolysis, for example treatment with ammonia in alcohols such as, for example, isopropanol, methanol or ethanol (G. Wagner, P. Richter and Ch. Garbe, Pharmazie 29 (1974), 12–55). Further methods of preparing amidines are the addition of hydrogen sulfide to a cyano group, followed by alkylation, for example by methylation with an agent like methyl iodide, of the resulting thioamide and subsequent reaction with ammonia (GDR Patent No. 235 866), or the addition of hydroxylamine which may be obtained from a hydroxylammonium salt with a base, to the cyano group followed by conversion of the amidoxime to the amidine, for example by catalytic hydrogenation (see, for example, R. P. Mull et al., J. Med. Pharm. Chem. 5 (1962), 651; B. J. Broughton et al., J. Med. Chem. 18 (1975), 1117).

Compounds of the formula I in which a group (($C_1-C_6$)-alkyl)-C(=NH)— bonded to a nitrogen atom is present can be prepared from a precursor compound containing said nitrogen atom as an NH group, for example, by the following methods. The precursor compound containing the NH group is reacted with a mono- or bis-benzyloxycarbonyl (Z) protected alkylamidine of the formulae (($C_1-C_6$)-alkyl)-C(=NH)—NH—Z or (($C_1-C_6$)-alkyl)-C(=NZ)—NH—Z of which the bis-protected reagent is more reactive than the mono-protected one (Y. Sugimura et al., Heterocycles 24 (1986), 1331–1345; J. Eustache and A Grob, Tetrahedron Lett. 36 (1995), 2045–2046). In another method, the precursor compound containing the NH group is reacted with an imino ether, for example, of the formula (($C_1-C_6$)-alkyl)-C(=NH)—O—(($C_1-C_4$)-alkyl) which in turn is available under standard conditions from a nitrile of the formula (($C_1-C_6$)-alkyl)-CN by addition of an alcohol in the presence of an acid. If two or more NH groups are present in the compound to be reacted with the imino ether or the Z-protected alkylamidine protection group strategies can be used to achieve the desired result, as is well known to one skilled in the art.

An imino ether which can be regarded as an activated nitrile, is also a versatile intermediate in case it is prepared from a cyano group that is present in a compound which already contains the indole system and which has been obtained as an intermediate during the synthesis of a compound of the formula I. For example, a cyano group that is present in the residue R$^{40}$ in a compound of the formulae VII or VII or in another residue can be reacted according to standard procedures to give an imino ether. Such an imino ether can be reacted, for example, with hydroxylamine to give an amidoxime group, or it can be reacted with 1,2-diaminoethane to give an imidazoline group, i.e. a 4,5-dihydro-1H-imidazol-2-yl substituent standing in place of the former cyano group. Again, in such reactions as in all reactions employed in the synthesis of the compounds of the formula I, depending on the individual case it may be favorable in order to avoid undesired reactions or secondary reactions to apply protection group techniques and to temporarily block groups like, for example, amino groups or carboxylic acid groups by protective groups suited to the specific synthesis problem.

Compounds of the formula I in which an amine oxide moiety or a pyridine N-oxide, quinoline N-oxide or isoquinoline N-oxide moiety is present can be obtained by oxidation of the amines or of the nitrogen heterocycles according to standard procedures as are described, for example, in J. March, Advanced Organic Chemistry, 3. ed., p. 1088.

The compounds of the formula I can also be prepared, for example, by synthesizing the compounds stepwise on a solid phase according to customary methods of solid phase chemistry which are well known to one skilled in the art and which are illustrated by the examples below.

Compounds of the formula Ia in which $R^2$ and $R^3$ in the formula I together form a group of the formula —$CH_2$—$CH_2$—N(—CO—$R^{20}$)—$CH_2$— can be prepared according to the above procedures starting from suitably substituted compounds of the formula IX which are commercially available or which can be prepared according to or analogously to syntheses described in the literature. In the formulae Ia and IX the residues have the meanings defined above.

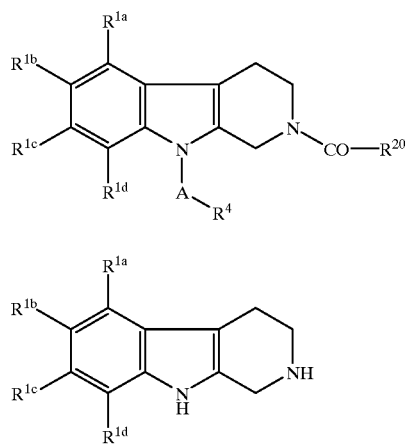

As is demonstrated in the pharmacological tests described below, the compounds of the formula I inhibit factor Xa activity. They can therefore advantageously be used as pharmaceuticals, especially when it is desired to reduce factor Xa activity or to produce effects that can be achieved by inhibiting factor Xa activity in a system, such as influencing coagulation or inhibiting blood clotting. Thus, the present invention also relates to the compounds of the formula I for use as pharmaceuticals as well as to the compounds of the formula I for use in the production of medicaments, especially of medicaments for treatment or prophylaxis of the conditions and diseases mentioned below and above. Further, the present invention provides a method of specifically inhibiting factor Xa activity by contacting factor Xa with a compound of the formula I, wherein a compound of the invention inhibits factor Xa catalytic activity either directly, within the prothrombinase complex or as a soluble subunit, or indirectly, by inhibiting the assembly of factor Xa into the prothrombinase complex. A preferred embodiment of the invention comprises such compounds of the formula I which can inhibit factor Xa activity with a Ki≦100 μM and, more preferably, with a Ki≦2 μM as determined in the factor Xa assay described below.

Inhibition of factor Xa activity or the production of effects achieved by such an inhibition can take place, for example, in vivo, i.e. in an individual. As used herein, the term "individual" means a vertebrate, including a mammal such as, for example a mouse, a rat, a rabbit, a dog, a pig and especially a human, in which factor Xa is involved in the coagulation cascade. It can also take place outside the body of an individual, for example, in an extracorporeal circulation or in the treatment of blood samples from an individual, and generally in vitro. In vitro uses of the compounds of the formula I are, for example, the use as a biochemical tool or reagent in scientific or analytical investigations or the use in in vitro diagnoses. Further, a compound of the formula I can advantageously be used as an anticoagulant which can be contacted with a blood sample to prevent coagulation. For example, an effective amount of a compound of the formula I can be contacted with a freshly drawn blood sample to prevent coagulation of the blood sample.

As used herein, the term "effective amount" when used in this connection means an amount of a compound of the formula I that inhibits factor Xa activity to the desired extent. The skilled artisan would recognize that an effective amount of a compound of the invention can be determined using the methods disclosed herein or otherwise known in the art.

In view of the disclosed utility of the compounds of the formula I, the skilled artisan also would recognize that an agent such as heparin can be replaced with a compound of the invention. Such a use of a compound of the formula I can result, for example, in a cost saving as compared to other anticoagulants, or in less side effects.

In a further embodiment, the present invention provides a method of inhibiting factor Xa in a patient in need thereof, comprising administering to said patient an effective factor Xa inhibitory amount of a compound of the formula I. As used herein, the term "patient" refers especially to a warmblooded animal including a mammal and particularly a human. A patient is in need of treatment to inhibit factor Xa when the patient is suffering from a disease state that can be beneficially influenced by inhibiting factor Xa activity or that is expected by the clinician to be beneficially influenced by inhibiting factor Xa acitivity. The identification of those patients who are in need of treatment to inhibit factor Xa is well within the ability and knowledge of one skilled in the art. A clinician skilled in the art can readily identify, for example by the use of clinical tests, physical examination and medical/family history, those patients who are in need of such a treatment.

Since a compound of the formula I can inhibit factor Xa activity, such a compound can be used for reducing or inhibiting blood clotting in an individual. Thus, the present invention further provides a method of reducing or inhibiting the formation of blood clots in an individual, especially in a patient in need thereof, by administering a therapeutically effective amount of a compound of the formula I.

A "therapeutically effective amount" relating to the production in an individual of an effect like inhibition or reduction of blood clotting, or an "effective factor Xa inhibitory amount" of a compound of the formula I means the amount or the dose of a compound of the formula I that has to be administered to an individual in order to achieve or to maintain the desired effect, or to inhibit factor Xa activity in the individual to the desired extent. Such an effective amount or dose to be administered has to be adjusted to the individual circumstances in each case. It can be readily determined by the use of conventional techniques using the methods described herein or otherwise known in the art, and by observing results obtained under analogous circumstances. In determining the effective dose, a number of factors are considered including, but not limited to the species of the patient; its size, age, and general health; the specific disease involved; the degree or the involvement or the severity of the disease; the response of the individual patient; the particular compound administered; the mode of administration; the bioavailability characteristics of the pharmaceutical preparation administered; the dose regimen selected; and the use of concomitant medication. An appropriate dosage can be established using clinical approaches well known in the medical art.

In general, in view of the above factors it is evident that the effective factor Xa inhibitory amount or the therapeutically effective amount of a compound of the formula I will vary and can be varied within wide limits. Usually, an effective amount of a compound of the formula I will vary from about 0.01 milligram per kilogram of body weight per day (mg/kg per day) to about 20 mg/kg per day. A daily dose of from about 0.1 mg/kg to about 10 mg/kg usually is preferred. These data refer to an adult human of about 75 kg of body weight. However, depending on the individual circumstances it may be necessary to deviate upward or downward from the doses given. In particular when administering relatively large quantities, it can be favorable to subdivide the daily dose into several, for example 2, 3 or 4 subdose administrations.

A compound of the formula I can be administered to an individual for the treatment of a variety of clinical conditions including, for example, the treatment and prophylaxis of cardiovascular disorders or complications associated, for example, with infection or surgery. Examples of cardiovascular disorders include restenosis, for example restenosis following angioplasty, reocclusion prophylaxis including reocclusion prophylaxis following lysis or dilatation (PTCA), conditions after coronary bypass operations, arterial, venous and microcirculatory disease states, cardiac infarction, angina pectoris including unstable angina pectoris, thromboembolic diseases, thromboses, embolism, adult respiratory distress syndrome, multi-organ failure, stroke and disseminated intravascular coagulation clotting disorder. Examples of related complications associated with surgery include, for example, deep vein and proximal vein thrombosis, which can occur following surgery. In general, a compound of the invention is useful as a medicament for reducing or inhibiting or preventing unwanted coagulation or blood clotting or thrombus formation in an individual.

The compounds of the formula I, their physiologically acceptable salts and other suitable derivatives thereof like prodrugs can be administered as medicaments or pharmaceuticals in the above-mentioned methods of treatment or prophylaxis on their own, in mixtures with each other or in the form of pharmaceutical compositions which comprise, as the active ingredient, an effective amount of at least one compound of the formula I and/or of a physiologically acceptable salt and/or another suitable derivative thereof in admixture or otherwise in association with a pharmaceutically acceptable carrier.

In effecting treatment of a patient, compounds of the formula I or pharmaceutical compositions comprising them can be administered in any form or mode which makes the compounds of the formula I bioavailable in effective amounts, including oral and parenteral routes. For example, they can be administered orally, subcutaneously, intramuscularly, intravenously, transdermally, intranasally, rectally, and the like. Oral administration is generally preferred but depending on the specific case other modes of administration can also be favorable, for example in an acute stage of a disease intravenous administration by means of injection or infusion. One skilled in the art can readily select the proper form and mode of administration depending upon the disease state to be treated, the stage of the disease, and other relevant circumstances.

Pharmaceutical compositions or medicaments comprising a compound of the formula I and/or a physiologically acceptable salt and/or another suitable derivative thereof can be made by combining by standard procedures the compounds of the formula I and/or their physiologically acceptable salts and/or other suitable derivatives thereof with one or more pharmaceutically acceptable carrier substances and/or auxiliary substances the proportion and nature of which are determined by the chosen route of administration and standard pharmaceutical practice. The pharmaceutical compositions or medicaments are prepared in a manner well known in the pharmaceutical art. The pharmaceutical compositions will, in general, contain an effective amount of one or more compounds of the formula I and/or their physiologically acceptable salt and/or other suitable derivatives thereof together with a suitable amount of a carrier so as to comprise the proper dosage for administration to an individual. The pharmaceutical compositions may be adapted for oral or parenteral use and may be administered to the patient in the form of, for example, tablets, capsules, suppositories, solutions, suspensions, ointments, tinctures, nasal sprays, aerosol mixtures, implants, rods, microcapsules or the like. Thus, together with the claimed compounds of the formula I the present invention provides useful pharmaceutical compositions or medicaments for inhibiting factor Xa activity, for inhibiting blood clotting and for the treatment and prophylaxis of the above-mentioned diseases in an individual. The present invention further encompasses a process for the preparation of pharmaceutical compositions or medicaments which comprise at least one compound of the formula I and/or a physiologically acceptable salt and/or another suitable derivative thereof, as well as it encompasses the use of the compounds of the formula I and/or physiologically acceptable salts and/or other suitable derivatives thereof for the preparation of medicaments, especially of medicaments for the treatment or prophylaxis of the above-mentioned diseases.

Pharmaceutically acceptable carrier and auxiliary substances are referred to as substances or compositions that are non-toxic to an individual or have acceptable toxicity as determined by the appropriate regulatory agency. The carrier substance or excipient may be a solid, semi-solid, or liquid material which can serve as a vehicle or medium for the active ingredient. As used herein, the term "pharmaceutically acceptable carrier" encompasses any of the standard pharmaceutical carriers such as liquid carriers, for example water, saline, phosphate buffered saline, an emulsion such as an oil/water or water/oil emulsion, or solid or semi-solid carriers such as, for example, lactose, corn starch, fats, waxes, etc. Suitable pharmaceutical carriers and their formulations are well known in the art and are described, for example, by Martin in Remington's Pharmaceutical Sciences, 15th Ed., Mack Publishing Co., Easton 1975, which is incorporated herein by reference also with respect to other aspects of the ingredients and of the preparation of pharmaceutical compositions.

Examples of auxiliary substances are fillers, disintegrants, binders, glidants, wetting agents, stabilizers, emulsifiers, preservatives, sweeteners, dyes, flavorants, aromatizing agents, thickeners, diluents, buffering substances, solubilizing agents, agents for achieving a slow-release effect, salts for altering the osmotic pressure, coating agents, antioxidants, etc.

For the purpose of oral administration, the compounds of the formula I and/or of their physiologically acceptable salts and/or other suitable derivatives thereof may be incorporated with excipients or inert diluents or edible carriers and used in the form of, for example, tablets, film tablets, coated tablets, pills, troches, capsules, granules, solutions, suspensions, emulsions, elixirs, syrups, wafers, chewing gums and the like, or they may be enclosed in gelatin capsule. The pharmaceutical compositions for oral administration may be varied depending upon the particular form. Usually such pharmaceutical compositions contain at least 1% of the active ingredient of the formula I and/or of a physiologically acceptable salt and/or another suitable derivative thereof and may conveniently contain up to about 90% of the weight of the unit. Preferably the content of the compounds of the formula I and/or their physiologically acceptable salts and/or other suitable derivatives is from about 4% to about 70% by weight. Preferably the amount of the active ingredient present in the compositions is such that a unit dosage form suitable for administration will be obtained.

The tablets, pills, capsules, troches and the like may also contain, for example, one or more of the following carrier and auxiliary substances: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide. Further, sweetening agents such as sucrose or saccharin may be added or flavoring agents such as peppermint, methyl salicylate or orange flavoring. When the dosage unit form is a capsule, it may contain, in addition to materials of the above type, a liquid carrier such as polyethylene glycol or a fatty oil. Other dosage unit forms may contain various other materials which modify the physical form of the dosage unit, for example, as coatings. Thus, tablets or pills may be coated with sugar, shellac, or other enteric coating agents. A syrup may contain, in addition to the active ingredient, for example sucrose as a sweetening agent and certain preservatives, dyes and colorings and flavors.

For the purpose of, for example, parenteral administration the compounds of the formula I and/or physiologically acceptable salts thereof and/or other suitable derivatives thereof may be incorporated into a solution or a suspension. The solutions or suspensions may, for example, also include one or more of the following carrier and auxiliary substances: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates; agents for the adjustment of toxicity such as sodium chloride or dextrose. The content of the compounds of the formula I and/or of their physiologically acceptable salt and/or other suitable derivatives thereof in the preparations for parenteral adminstration may be varied. Usually they contain at least 0.1% by weight of the compound of the formula I and/or of a physiologically acceptable salt and/or another suitable derivative thereof and up to 90% by weight. Preferably the content of the compound of the formula I and/or the physiologically acceptable salts thereof and/or other suitable derivatives thereof is from about 0.1% to 50%. The parenteral preparations can be enclosed, for example, in ampules, disposable syringes, multiple dose vials made of glass or plastic, or infusion bottles. Suitable excipients for microcapsuies, implants and rods are, for example, mixed polymers of glycolic acid and lactic acid.

Generally, the amount of the compounds of the formula I and/or physiologically acceptable salts thereof and/or other suitable derivatives thereof that is present in a pharmaceutical composition is from about 0.5 mg to about 1 g, preferably from about 1 mg to about 500 mg. Besides one or more compounds of the formula I and/or one or more physiologically acceptable salts thereof and/or one or more other suitable derivatives thereof as active compounds the pharmaceutical compositions according to present invention may also contain one or more other pharmacologically active compounds. Any materials used in preparing the various pharmaceutical compositions should be pharmaceutically pure and non-toxic in the amounts used.

In another, more general embodiment the present invention provides compositions comprising at least one compound of the formula I and/or a salt thereof and/or another suitable derivative thereof in admixture or otherwise in association with one or more inert carriers. These compositions are useful, for example, as assay standards, as convenient means of making bulk shipments, as pharmaceutical compositions or as starting materials for the production of pharmaceutical compositions. The amount of a compound of the formula I in such a composition will generally vary from about 0.001% to about 90% by weight. Inert carriers can be any material which does not degrade or otherwise covalently react with a compound of the formula I. Examples of suitable inert carriers are water; aqueous buffers, such as, for example, those which are generally useful in High Performance Liquid Chromatography (HPLC) analysis; organic solvents, such as acetonitrile, ethyl acetate, hexane and the like; and pharmaceutically acceptable carrier and/or auxiliary substances.

The compounds of the formula I can also be used as starting materials or chemical intermediates in the preparation of other compounds, especially in the preparation of other pharmacologically active compounds. Examples for such conversions of compounds of the invention into other compounds of the invention are discussed above and are given in detail below. For this use, besides the compounds of the formula I and their physiologically acceptable salts also other salts of the compounds of the formula I can be useful which are not suitable or less suitable for use as pharmaceuticals. Thus, the present invention also relates to compounds of the formula I and their salts in general as chemical intermediates, especially as intermediates in the preparation of pharmacologically active compounds. A subject of the invention also are intermediates which are used in the syntheses of the compounds of the formula I described above and below, and their use as chemical intermediates, especially as intermediates in the preparation of pharmacologically active compounds.

The following tests can serve to investigate the pharmacological activity and to illustrate the utility of the compounds of the present invention as factor Xa inhibitors.

Test 1: In Vitro Inhibition of Selected Purified Coagulation Enzymes and Other Serine Proteases The ability of a compound of the formula I to inhibit factor Xa, thrombin, plasmin, elastase and trypsin may be assessed by determining the concentration of the compound of the formula I that inhibits enzyme activity by 50% ($IC_{50}$). Purified enzymes are used in chromogenic assays. To determine the inhibition constant Ki, the $IC_{50}$ value is corrected for competition with substrate using the formula $$Ki' IC_{50} \times (1/\{1+((\text{substrate concentration})/\text{substrate Km})\})$$

wherein Km is the Michaelis-Menten constant (Chen and Prusoff, Biochem. Pharmacol. 22 (1973), 3099–3018 which is incorporated herein by reference).

a. Factor Xa Assay

TBS-PEG buffer (50 mM Tris-Cl, pH 7.8, 200 mM NaCl, 0.05% (w/v) PEG-8000, 0.02% (w/v) NaN$_3$) is used for this assay. The IC$_{50}$ is determined by combining in appropriate wells of a Costar half-area microtiter plate 25 μl human factor Xa (Enzyme Research Laboratories, Inc.; South Bend, Ind.) in TBS-PEG; 40 μl 10% (v/v) DMSO in TBS-PEG (uninhibited control) or various concentrations of the compound to be tested diluted in 10% (v/v) DMSO in TBS-PEG; and substrate S-2765 (N(α)-benzyloxycarbonyl-D-Arg-Giy-L-Arg-p-nitroanilide; Kabi Pharmacia, Inc.; Franklin Ohio) in TBS-PEG.

The assay is performed by pre-incubating the compound of formula I plus enzyme for 10 min. Then the assay is initiated by adding substrate to obtain a final volume of 100 μl. The initial velocity of chromogenic substrate hydrolysis is measured by the change in absorbance at 405 nm using a Bio-tek Instruments kinetic plate reader (Ceres UV900HDi) at 25° C. during the linear portion of the time course (usually 1.5 min after addition of substrate). The concentration of inhibitor that causes a 50% decrease in the rate of substrate hydrolysis is predicted by linear regression after plotting the relative rates of hydrolysis (compared to the uninhibited control) versus the log of the concentration of the compound of formula I. The enzyme concentration is 0.5 nM and substrate concentration is 140 μM.

b. Thrombin Assay

TBS-PEG buffer is used for this assay. The IC$_{50}$ is determined as above for the factor Xa assay, except that the substrate is S-2366 (L-PyroGlu-L-Pro-L-Arg-p-nitroanilide; Kabi) and the enzyme is human thrombin (Enzyme Research Laboratories, Inc.; South Bend Ind.). The enzyme concentration is 175 μM.

c. Plasmin Assay

TBS-PEG buffer is used for this assay. The IC$_{50}$ is determined as described above for the factor Xa assay, except that the substrate is S-2251 (D-Val-L-Leu-L-Lys-p-nitroanilide; Kabi) and the enzyme is human plasmin (Kabi). The enzyme concentration is 5 nM and the substrate concentration is 300 μM.

d. Trypsin Assay

TBS-PEG buffer containing 10 mM CaCl$_2$ is used for this assay. The IC$_{50}$ is determined as described above in the factor Xa assay, except that the substrate is BAPNA (benzoyl-L-Arg-p-nitroanilide; Sigma Chemical Co.; St. Louis Mo.) and the enzyme is bovine pancreatic trypsin (Type XIII, TPCK treated; Sigma). The enzyme concentration is 50 nM and the substrate concentration is 300 μM.

e. Elastase Assay

Tris-Cl buffer (pH 7.4, 300 mM NaCl, 2% (v/v) N-methyl-pyrrolidone, 0.01% (w/v) NaN$_3$) is used for this assay. The IC$_{50}$ is determined as described above for the assay for factor Xa, except that the substrate is succinyl-Ala-Ala-Ala-p-nitroanilide (Calbiochem-Nova Biochem Corp.; San Diego Calif.) and the enzyme is human neutrophil elastase (Athens Research and Technology, Inc.; Athens Ga.). The enzyme concentration is 75 nM and the substrate concentration is 600 μM. The control compound is "TENSTOP" (N(α)-tosyl-Gly-p-amidinophenylalanine methyl ester; American Diagnostica, Inc.; Greenwish Conn.), which is a reversible factor Xa inhibitor (Sturzebecher et al., Thromb. Res. 54 (1989), 245–252; Hauptmann et al., Thromb. Haem. 63 (1990), 220–223, each of which is incorporated herein by reference).

Test 2: Assays for Determining Inhibition of Coagulation

The effectiveness of the compounds of the formula I may be assessed by the in vitro prothrombin time (PT) assay using pooled human donor plasma. An ex vivo assay may also be used in which plasma is collected at various times after intravenous (iv) administration of a compound of the formula I to rats or to rabbits, or after intraduodenal (id) administration to rats, and analysis using the PT assay to determine plasma half-life. The PT assay is initiated with a thromboplastin dilution selected to obtain an extended and highly reproducible coagulation endpoint, referred to as the "dilute PT assay" as described below. The effectiveness of the compounds may also be determined using an in vivo rat arteriovenous shunt model of thrombosis.

a. In Vitro Dilute Prothrombin Time Assay

100 μl prewarmed (37° C.) pooled human platelet poor plasma (PPP) is added to a fibrometer cup (Baxter Diagnostics, Inc.; McGaw Park Ill.). 50 μl of various concentrations of a compound of the formula I in TBS-BSA with calcium (50 mM Tris-Cl, 100 mM NaCl, 0.1% (w/v) bovine serum albumin (BSA), 20 mM CaCl$_2$) is added. In control experiments, TBS-BSA with calcium but without a test compound of the formula I is added for measurement of uninhibited coagulation time. 150 μl diluted prewarmed rabbit thromboplastin (Baxter) with calcium is added to the fibrometer cup and the fibrometer timer is started. A rabbit thromboplastin dilution curve is obtained prior to treating the compound and is used to choose a thromboplastin dilution that allows approximately 30 sec PT time for uninhibited controls. The experimental concentration giving 50% inhibition of coagulation (EC$_{50}$) is calculated from the dilution curve times.

Alternatively, the dilute prothrombin time assay may be conducted using the "research" mode on an Instrumentation Laboratories (IL) ACL3000-plus automated coagulation instrument (IL; Milan, Italy). Thromboplastin is diluted until a clotting time of 30–35 seconds is achieved. This clotting time is taken as 100% activity. A standard curve for calibration is established by serial 2-fold dilution of the diluted thromboplastin reagent (rabbit brain IL-brand thromboplastin). During the assay, a 50 μl sample (plasma separated by centrifugation) is mixed with 100 μl thromboplastin reagent and nephelometric readings are taken over 169 sec. Coagulation time is determined from the maximal rate of change of light scatter calculated by the instrument. Inhibition is expressed as percent activity as determined by comparison with the calibration curve.

b. Ex Vivo Dilute Prothrombin Time Assay

A test compound of the formula I is administered iv either through the tail vein (rat) or ear vein (rabbit) following an approved protocol. Blood samples of 1 ml volume are removed at timed intervals after administration of the test compound from a cannulated carotid artery (rat) or auricular artery (rabbit). After centrifugation to obtain PPP, the plasma is immediately stored on ice or frozen.

For dilute prothrombin time determination, the plasma is prewarmed and assayed as described above. Percent inhibition is calculated from a thromboplastin dilution curve, which is run with each series of samples, and used to determine the time at which approximately 50% of the initial anticoagulant activity remains in the plasma (T$_{1/2}$).

The test compound of the formula I may also be administered to rats using an intraduodenal dosing protocol. Male Sprague-Dawley rats weighing approximately 300 g are anesthetized with a combination of ketamine/xylazine administered subcutaneously, following an approved protocol. The right carotid artery is cannulated for blood sampling. A laparotomy is performed and the duodenum is cannulated with a ball-tip needle and tied into place to ensure that the suture is distal to the point of insertion. An additional tie is placed proximal to the insertion point to prevent leakage of gastric contents. The effectiveness of the suture in preventing a compound from reaching the site of insertion is tested by pressure testing at the conclusion of each experiment. The point of insertion is approximately 4 cm from the duodenal-gastric junction. The compound is administered in 1 ml normal saline. A blood sample of 0.7 ml is drawn prior to administration of the test compound of the formula I and at 15, 30, 60, 90 and 120 min after administration. The plasma is separated by centrifugation and assayed for inhibition of coagulation using the dilute prothrombin time assay.

c. Rat Arteriovenous Shunt Model of Thrombosis

The anti-thrombotic efficacy of the compounds of the invention may be assessed using rat extracorporeal arteriovenous (AV) shunt. The AV shunt circuit consists of a 20 cm length of polyethylene (PE) 60 tubing inserted into the right carotid artery, a 6 cm length of PE 160 tubing containing a 6.5 cm length of mercerized cotton thread (5 cm exposed to blood flow), and a second length of PE 60 tubing (20 cm) completing the circuit into the left jugular vein. The entire circuit is filled with normal saline prior to insertion.

A test compound of the formula I is administered by continuous infusion into the tail vein using a syringe pump and butterfly catheter (infusion volume 1.02 ml/hr). The compound is administered for 30 min, then the shunt is opened and blood allowed to flow for a period of 15 min (total of 45 min infusion). At the end of the 15 min period, the shunt is clamped and the thread is carefully removed and weighed on an analytical balance. Percent inhibition of thrombus formation is calculated using the thrombus weight obtained from control rats, which are infused with saline.

In Table 1 some inhibition constants Ki for factor Xa inhibition by example compounds of the present invention are given. The inhibition constants were determined as described above (Test 1, a., Factor Xa Assay).

TABLE 1

Ki values for factor Xa inhibition

| Example | Ki (Xa) (µM) | Example | Ki (Xa) (µM) |
|---|---|---|---|
| 2 | 0.10 | 97 | 1.60 |
| 4 | 0.090 | 101 | 7.9 |
| 6 | 0.40 | 103 | 1.7 |
| 13 | 55 | 106 | 0.04 |
| 15 | 13 | 110 | 1.1 |
| 21(4) | 4.8 | 112 | 0.013 |
| 23 | 7.0 | 115 | 0.009 |
| 24 | 0.11 | 117 | 0.015 |
| 27 | 0.61 | 120 | 0.0048 |
| 35 | 0.009 | 121 | 0.13 |
| 39 | 0.007 | 124 | 0.025 |
| 47 | 0.007 | 125 | 0.009 |
| 56 | 0.082 | 132 | 2.0 |
| 58 | 0.014 | 133 | 0.05 |
| 77 | 0.009 | 137 | 0.011 |
| 78 | 0.21 | 141 | 0.72 |
| 81 | 63 | 146 | 0.013 |
| 84 | 0.90 | 149 | 3.3 |
| 87 | 110 | | |

As used herein, the following terms have the indicated meanings: "g" refers to grams; "mmol" refers to millimoles; "mM" refers to millimolar; "ml" refers to milliliters; "m.p." refers to melting point; "dec." refers to decomposition; "° C." refers to degrees Celsius; "µl" refers to microliters; "nM" refers to nanomolar and "µM" refers to micromolar.

EXAMPLES

The following examples present typical syntheses of the compounds of the formula I. These examples are understood to be illustrative only and are not intended to limit the scope of the present invention in any way. The compounds of the examples were characterized by mass spectra (MS) and/or NMR spectra and/or melting points.

Example 1

4-({[1-(3-Amidino-benzyl)-1H-indole-2-carbonyl]-amino}-methyl)-1-methylpyridinium trifluoroacetate trifluoroacetic acid salt

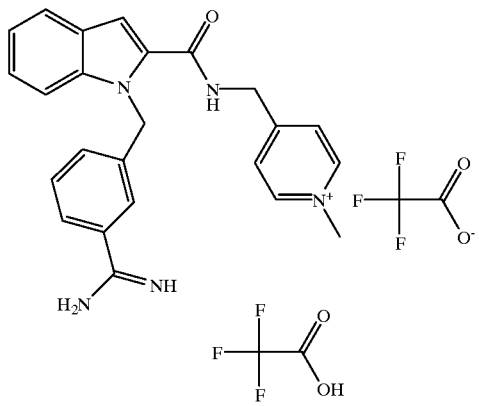

1.) 1-(3-Cyano-benzyl)-1H-indole-2-carboxylic acid ethyl ester

A solution of 1.9 g (10 mmol) of 1H-indole-2-carboxylic acid ethyl ester in 15 ml of dimethylformamide was treated with 1.2 g (10.5 mmol) of potassium tert-butoxide. The mixture was stirred at room temperature for 10 minutes to give a clear solution. 2 g (10 mmol) of 3-cyano-benzyl bromide was added and the mixture was slowly heated to 100° C., cooled, acidified with acetic acid and poured on ice-water. The precipitated product was filtered off and dissolved in methylene chloride. The solution was dried and evaporated and the residue was crystallized from methylene chloride/methanol to give 2.5 g of colorless crystals with m.p. 93–95° C.

2.) 1-(3-Cyano-benzyl)-1H-indole-2-carboxylic acid

A mixture of 0.61 g (2 mmol) of the above 1-(3-cyano-benzyl)-1H-indole-2-carboxylic acid ethyl ester, 25 ml of methanol, 2.5 ml of water, and 0.6 g of sodium hydroxide was heated to reflux for 15 minutes. The solvent was evaporated and the residue was partitioned between methylene chloride and 1 N hydrochloric acid. The organic phase was dried and evaporated. Crystallization from methylene chloride/hexane gave 0.53 g of colorless crystals with m.p. 226–228° C. (dec.).

3.) 1-(3-Cyano-benzyl)-N-[(4-pyridyl)methyl]-1H-indole-2-carboxamide

A mixture of 300 mg of the above 1-(3-cyano-benzyl)-1H-indole-2-carboxylic acid, 20 ml of methylene chloride, and 10 ml of thionyl chloride was heated to reflux for 4 hours. The solvent and excess reagent were evaporated, at the end azeotropically with toluene. The residue was dissolved in methylene chloride and the solution was treated with 0.3 ml of 4-aminomethylpyridine. The mixture was layered with 10% aqueous sodium carbonate solution and stirred vigorously for 15 minutes. The organic layer was dried and evaporated and the residue was crystallized from ethyl acetate/ether to yield 280 mg of colorless crystals with m.p. 154–156° C.

4.) N-[(4-pyridyl)methyl]-1-[(3-thiocarbamoyl-phenyl)methyl]-1H-indole-2-carboxamide Hydrogen sulfide was introduced for 15 minutes into an ice-water cooled solution of 250 mg of the above 1-(3-cyano-benzyl)-N-[(4-pyridyl)methyl]-1H-indole-2-carboxamide in 5 ml of pyridine and 4 ml of triethylamine. The mixture was stirred at room temperature for 18 hours in a sealed vial and then partitioned between toluene/pyridine and 10% aqueous sodium carbonate solution. The organic layer was dried and evaporated and the residue was crystallized from acetone/ether to yield 220 mg of light yellow crystals with m.p. 197–200° C. (dec.).

5.) 4-({[1-(3-Amidino-benzyl)-1H-indole-2-carbonyl]-amino}-methyl)-1-methylpyridinium trifluoroacetate trifluoroacetic acid salt A mixture of 220 mg of N-[(4-pyridyl)methyl]-1-[(3-thiocarbamoyl-phenyl)methyl]-1H-indole-2-carboxamide, 2 ml of dimethylsulfoxide, 5 ml of acetone, and 0.5 ml of methyl iodide was stirred in a sealed vial for 20 hours. The reaction mixture was diluted with toluene and evaporated. The residue was dissolved in acetone and the product was precipitated with ether. The solvents were decanted and the residue was stirred with fresh acetone/ether. The solids were separated and dried in vacuum. This material was dissolved in 20 ml of methanol and the solution was treated with 0.3 ml of acetic acid and 0.4 g of ammonium acetate. The mixture was heated to 55–60° C. for 2 hours in a sealed vial. The solvent was evaporated and the bulk of the ammonium acetate was removed under high vacuum. The residue was lyophilized from acetonitrile/water 1:1 containing 1% of trifluoroacetic acid. Final purification by reverse phase HPLC gave the product with a retention time of 16.14 min and correct molecular weight.

Example 2

(RS)-4-(1-{[1-(3-Amidino-benzyl)-1H-indole-2-carbonyl]-amino}-ethyl)-1-methylpyridinium trifluoroacetate trifluoroacetic acid salt

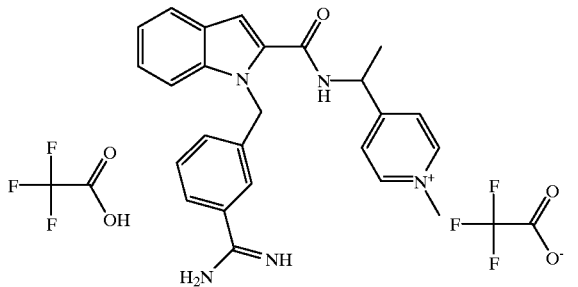

1.) (RS)-1-(3-Cyano-benzyl)-N-[1-(4-pyridyl)-1-ethyl]-1H-indole-2-carboxamide

A mixture of 280 mg of 1-(3-cyano-benzyl)-1H-indole-2-carboxylic acid (example 1/2), 10 ml of methylene chloride, and 4 ml of thionyl chloride was heated to reflux for 4 hours. The solvent and excess reagent were evaporated, at the end azeotropically with hexane. This acid chloride was dissolved in methylene chloride and added to a mixture of 0.3 g (RS)-1-(4-pyridyl)ethylamine dihydrochloride, 20 ml of methylene chloride, and 0.5 ml of diisopropylethylamine. After stirring for 15 minutes, the reaction mixture was layered with 10% aqueous sodium carbonate and stirred vigorously for another 15 minutes. The organic layer was dried and evaporated and the residue was crystallized from ethyl acetate/ether to yield 300 mg of colorless product with m.p. 176–180° C.

2.) (RS)-N-[1-(4-Pyridyl)-1-ethyl]-1-[(3-thiocarbamoyl-phenyl)methyl]-1H-indole-2-carboxamide Hydrogen sulfide was introduced for 15 minutes into an ice-water cooled solution of 250 mg of the above (RS)-1-(3-cyano-benzyl)-N-[-(4-pyridyl)-1-ethyl]-1H-indole-2-carboxamide in 5 ml of pyridine and 4 ml of triethylamine. The mixture was stirred at room temperature for 18 hours in a sealed vial and then evaporated. The residue was crystallized from acetone/ether to yield 220 mg of light yellow crystals with m.p. 197–200° C. (dec.).

3.) (RS)-4-(1-{[1-(3-Amidino-benzyl)-1H-indole-2-carbonyl]-amino}ethyl)-1-methylpyridinium trifluoroacetate trifluoroacetic acid salt A mixture of 200 mg of (RS)-N-[1-(4-pyridyl)-1-ethyl]-1-[(3-thiocarbamoyl-phenyl)methyl]-1H-indole-2-carboxamide, 1.5 ml of dimethylsulfoxide, 5 ml of acetone, and 0.8 ml of methyl iodide was stirred in a sealed vial for 18 hours. The reaction mixture was diluted with toluene and evaporated. The residue was dissolved in acetone and the product was precipitated with ether. The solvents were decanted and the residue was stirred with fresh acetone/ether. The solids were separated, dried in vacuum, and dissolved in 20 ml of methanol. After addition of 0.3 ml of acetic acid and 0.65 g of ammonium acetate the mixture was heated at 55° C. in a sealed vial for 3 hours. The solvent and excess ammonium acetate were removed in vacuum and the residue was lyophilized from acetonitrile/water containing 1% of trifluoroacetic acid. The crude material was purified by reverse phase HPLC to give the desired product with retention time of 16.6 min and correct molecular weight.

Example 3

1-(3-Amidino-benzyl)-N-(4-amidino-benzyl)-1H-indole-2-carboxamide trifluoroacetic acid salt

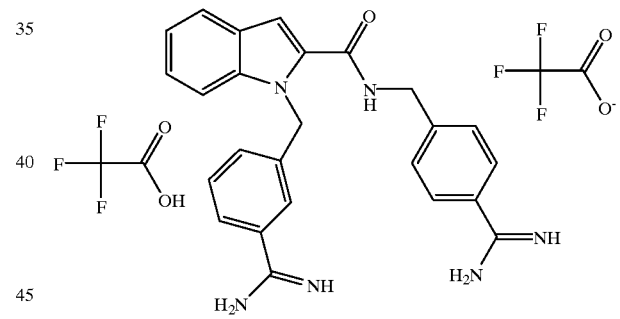

1.) 1-(3-Cyano-benzyl)-N-(4-cyano-benzyl)-1H-indole-2-carboxamide

A mixture of 275 mg (1 mmol) of 1-(3-cyano-benzyl)-1H-indole-2-carboxylic acid (example 1/2), 350 mg of diphenylphosphoryl azide, 200 mg of 4-cyano-benzylamine hydrochloride, 5 ml of dimethylformamide, and 0.4 ml of diisopropylethylamine was stirred at room temperature for 20 hours. The solvent was evaporated and the residue was dissolved in methylene chloride. The solution was washed with 1 N hydrochloric acid and 10% aqueous sodium carbonate, dried, and evaporated. The residue was passed over 10 g of silica gel using methylene chloride for elution. Crystallization from methylene chloride/hexane gave 310 mg of colorless crystals with m.p. 160–162° C.

2.) 1-[(3-Thiocarbamoyl-phenyl)methyl]-N-[4-(thiocarbamoyl-phenyl)methyl]-1H-indole-2-carboxamide A solution of 150 mg of the above 1-(3-cyano-benzyl)-N-(4-cyano-benzyl)-1H-indole-2-carboxamide in 4 ml of pyridine and 2 ml of triethylamine was cooled in ice water and saturated with hydrogen sulfide. After stirring in a sealed vessel for 18 hours at room temperature, the solvent was evaporated and the residue was crystallized from acetone/methylene chloride/ether to yield 180 mg of light yellow crystals with m.p. 225–230° C. (dec.).

3.) 1-(3-Amidino-benzyl)-N-(4-amidino-benzyl)-1H-indole-2-carboxamide trifluoroacetic acid salt A mixture of 160 mg of 1-[(3-thiocarbamoyl-phenyl)methyl]-N-[4-(thiocarbamoyl-phenyl)methyl]-1H-indole-2-carboxamide, 5 ml acetone, 1 ml of dimethylsulfoxide, and 0.4 ml of methyl iodide was stirred at room temperature for 18 hours. It was diluted with toluene and evaporated. The residue was stirred with acetone/ether and the solvent was decanted. The residue was dissolved in acetone/methanol and the product was precipitated by addition of ether. The solids were filtered off, dried, and dissolved in 20 ml of methanol. The solution was treated with 0.3 ml of acetic acid and 0.6 g of ammonium acetate and the mixture was heated in a sealed vial for 3 hours to 55° C. The solvent was evaporated and the bulk of ammonium acetate was removed under high vacuum. The residue was lyophilized from acetonitrile and water containing 1% of trifluoroacetic acid. Purification by HPLC yielded the title compound with retention time of 17.46 min and the correct molecular weight.

Example 4

[4-({[1-(3-Amidino-benzyl)-1H-indole-2-carbonyl]-amino}-methyl)-phenyl]-trimethyl-ammonium trifluoroacetate trifluoroacetic acid salt

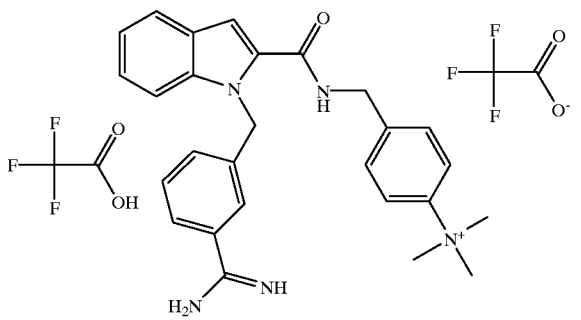

1.) 1-[3-Cyano-benzyl]-N-[4-(dimethylaminophenyl)methyl]-1H-indole-2-carboxamide A mixture of 275 mg (1 mmol) of 1-(3-cyano-benzyl)-1H-indole-2-carboxylic acid (example 1/2), 350 mg of diphenylphosphoryl azide, 250 mg of 4-(dimethylamino)benzylamine dihydrochloride, 5 ml of dimethylformamide, and 0.5 ml of diisopropylethylamine was stirred at room temperature for 20 hours. The solvent was evaporated and the residue was dissolved in methylene chloride. The solution was washed with 10% aqueous sodium carbonate, dried, and evaporated. Crystallization of the residue from methylene chloride/ether/hexane gave 330 mg of colorless crystals with m.p. 153–155° C.

2.) N-[4-(Dimethylaminophenyl)methyl]-1-[(3-thiocarbamoyl-phenyl)methyl]-1H-indole-2-carboxamide Hydrogen sulfide was introduced into an ice-water cooled solution of 200 mg of the above 1-(3-cyano-benzyl)-N-[4-(dimethylaminophenyl)methyl]-1H-indole-2-carboxamide in 5 ml of pyridine and 3 ml of triethylamine. The mixture was stored in a sealed vial in the refrigerator for 3 days. The solvents were evaporated and the residue was crystallized from methylene chloride/ether/hexane to leave 170 mg of yellowish product with m.p. 152–154° C.

3.) [4-({[1-(3-Amidino-benzyl)-1H-indole-2-carbonyl]-amino}-methyl)-phenyl]-trimethyl-ammonium trifluoroacetate trifluoroacetic acid salt A mixture of 160 mg of N-[4-(dimethylaminophenyl)methyl]-1-[(3-thiocarbamoylphenyl)methyl]-1H-indole-2-carboxamide, 5 ml of acetone, and 0.4 ml of methyl iodide was stirred in a sealed vial for 18 hours at room temperature. The product was precipitated by addition of ether and collected by filtration. The solids were washed with acetone/ether and dried. This material was dissolved in 10 ml of methanol and the solution was treated with 0.25 ml of acetic acid and 0.5 g of ammonium acetate. The mixture was heated at 55° C. for 3 hours in a sealed vial. The solvent was evaporated and the residue was lyophilized from acetonitrile and water containing 1% of trifluoroacetic acid. Purification by HPLC gave the title compound with retention time of 17.38 min and correct molecular weight.

Example 5

4-({[1-(3-Amidino-benzyl)-1H-indole-2-carbonyl]-ethyl-amino}-methyl)-1-methyl-pyridinium trifluoroacetate trifluoroacetic acid salt

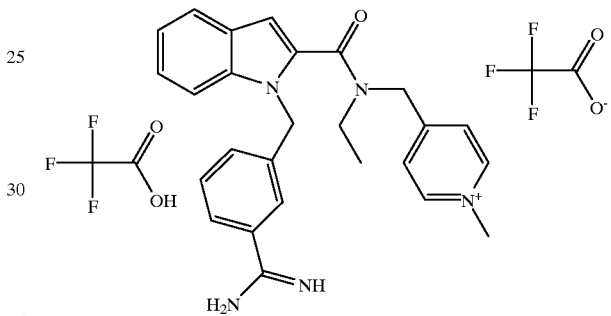

1.) 1-(3-Cyano-benzyl)-N-ethyl-N-[(4-pyridyl)methyl]-1H-indole-2-carboxamide

A mixture of 276 mg of 1-(3-cyano-benzyl)-1H-indole-2-carboxylic acid (example 1/2), 10 ml of methylene chloride, and 5 ml of thionyl chloride was heated to reflux for 4 hours. The solvent and excess reagent were evaporated, at the end azeotropically with hexane. The crystalline residue was dried in vacuum and dissolved in 20 ml of methylene chloride. (4-Ethylaminomethyl)pyridine, 0.3 ml, was added and the mixture was layered with 10% aqueous sodium carbonate solution and stirred vigorously for 15 minutes. The organic phase was dried and evaporated and the residue was chromatographed over 13 g of silica gel using 30% acetone in methylene chloride for elution. The product (240 mg) was obtained as a colorless viscous oil which was used in the next step.

2.) N-Ethyl-N-[(4-pyridyl)methyl]-1-[(3-thiocarbamoyl-phenyl)methyl]-1H-indole-2-carboxamide The above material was dissolved in 8 ml of pyridine and 4 ml of triethylamine. The solution was saturated with hydrogen sulfide while cooled in ice-water. The mixture was stirred in a sealed vial for 24 hours and then partitioned between toluene and 10% aqueous sodium carbonate solution. The organic layer was dried and evaporated and the residue was crystallized from acetone/hexane to yield 215 mg of light yellow crystals with m.p. 180–184° C.

3.) 4-({[1-(3-Amidino-benzyl)-1H-indole-2-carbonyl]-ethyl-amino}-methyl)-1-methyl-pyridinium trifluoroacetate trifluoroacetic acid salt A mixture of 200 mg of N-ethyl-N-[(4-pyridyl)methyl]-1-[(3-thiocarbamoyl-phenyl)methyl]-1H-indole-2- carboxamide, 5 ml of acetone, 1 ml of dimethylsulfoxide, and 0.7 ml of methyl iodide was stirred in a sealed vial for 20 hours at room temperature. The solvents were evaporated and the residue was stirred with ether. The solvent was decanted and the gummy residue was stirred with acetone/ether. The solids were separated and dried. This material was dissolved in 20 ml of methanol and the solution was treated with 0.25 ml of acetic acid and 0.6 g of ammonium acetate. The mixture was heated at 55° C. for 3 hours in a sealed vial. The solvent was evaporated and the residue was lyophilized from acetonitrile and water containing 1% of trifluoroacetic acid. Purification by HPLC gave pure product with retention time of 16.80 min and correct molecular weight.

Example 6

[4-({[1-(3-Amidino-benzyl)-1H-indole-2-carbonyl]-amino}-methyl)-benzyl]-trimethyl-ammonium trifluoroacetate trifluoroacetic acid salt

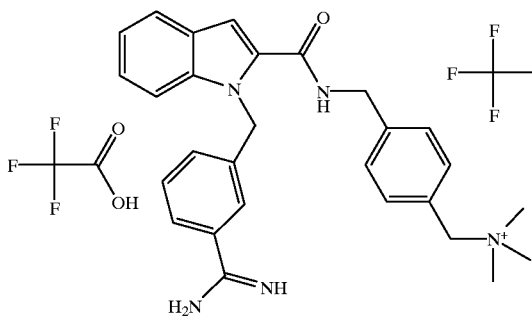

1.) 1-(3-Cyano-benzyl)-N-{[4-(dimethylaminomethyl)phenyl]methyl}-1H-indole-2-carboxamide A mixture of 275 mg (1 mmol) of 1-(3-cyano-benzyl)-1H-indole-2-carboxylic acid (example 1/2), 350 mg of diphenylphosphoryl azide, 250 mg of 4-(dimethylaminomethyl)benzylamine dihydrochloride, 5 ml of dimethylformamide, and 0.2 ml of diisopropylethylamine was stirred at room temperature for 3 days. The solvent was evaporated and the residue was partitioned between methylene chloride and 10% aqueous sodium carbonate solution. The organic phase was dried and evaporated. The residue was stirred with ether/hexane to yield 240 mg of colorless crystals with m.p. 127–128° C.

2.) N-{[4-(Dimethylaminomethyl)phenyl]-methyl}-1-[(3-thiocarbamoyl-phenyl)methyl]-1H-indole-2-carboxamide A solution of 240 mg of the above 1-(3-cyano-benzyl)-N-{[4-(dimethylaminomethyl)phenyl]-methyl}-1H-indole-2-carboxamide in 5 ml of pyridine and 3 ml of triethylamine was saturated with hydrogen sulfide while cooled in ice-water. The mixture was allowed to sit for 20 hours at room temperature in a sealed vial. The solvents were evaporated and the residue was stirred with ether to yield 200 mg of yellow crystals with m.p. 120–125° C.

3.) [4-({[1-(3-Amidino-benzyl)-1H-indole-2-carbonyl]-amino}-methyl)-benzyl]-trimethyl-ammonium trifluoroacetate trifluoroacetic acid salt A mixture of 200 mg of N-{[4-(dimethylaminomethyl)phenyl]-methyl}-1-[(3-thiocarbamoyl-phenyl)methyl]-1H-indole-2-carboxamide, 6 ml of acetone, 1 ml of dimethylsulfoxide, and 0.8 ml of methyl iodide was stirred in a sealed vial for 20 hours. After evaporation the residue was dissolved in acetone and the product was precipitated with ether. The solids were reprecipitated from acetone with ether. After drying the product was dissolved in 20 ml of methanol. The solution was treated with 0.3 ml of acetic acid and 0.6 g of ammonium acetate and the mixture was heated at 55° C. for 3 hours. The solvent was evaporated and the residue was lyophilized from acetonitrile/water containing 1% of trifluoroacetic acid. The crude product was purified by HPLC to give the title compound with a retention time of 17.96 min and the correct molecular weight.

Example 7

4-({[1-(3-Amidino-benzyl)-5-fluoro-1H-indole-2-carbonyl]-amino}-methyl)-1-methyl-pyridinium trifluoroacetate trifluoroacetic acid salt

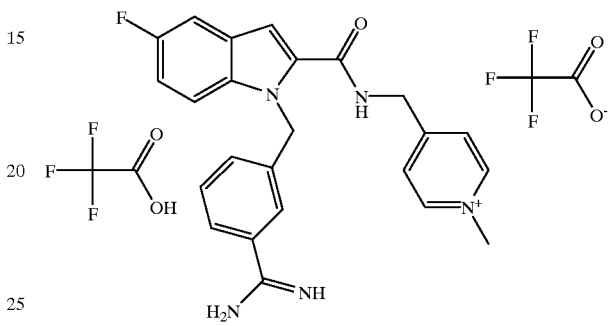

1.) 1-(3-Cyano-benzyl)-5-fluoro-1H-indole-2-carboxylic acid methyl ester

A solution of 0.96 g (5 mmol) of 5-fluoro-1H-indole-2-carboxylic acid methyl ester in 20 ml of dimethylformamide was treated with 0.6 g (5.25 mmol) of potassium tert-butoxide. The mixture was stirred at room temperature for 10 minutes to give a clear solution. 3-Cyano-benzyl bromide, 1 g (5 mmol), was added and the mixture was slowly heated to 100° C., cooled, acidified with acetic acid and poured on ice-water. The precipitated product was filtered off and dissolved in methylene chloride. The solution was dried and evaporated and the residue was crystallized from methanol to give 1.3 g of colorless crystals with m.p. 148–148° C.

2.) 1-(3-Cyano-benzyl)-5-fluoro-1H-indole-2-carboxylic acid

A mixture of 1 g of the above 1-(3-cyano-benzyl)-5-fluoro-1H-indole-2-carboxylic acid methyl ester, 30 ml of methanol, 3 ml of water, and 0.5 g of sodium hydroxide was heated to reflux for 20 minutes. The solvent was partially evaporated and the residue was acidified with 2 N hydrochloric acid. The precipitated crystals were filtered off and dissolved in methylene chloride/2-propanol. The solution was dried and evaporated and the residue was crystallized from acetone/hexane to give 0.9 g of colorless crystals with m.p. 247–250° C. (dec.).

3.) 1-(3-Cyano-benzyl)-5-fluoro-N-[(4-pyridyl)methyl]-1H-indole-2-carboxamide

This compound was prepared by converting the above carboxylic acid to the acid chloride and reacting it with 4-aminomethylpyridine as described for the desfluoro analog in example 1/3. It was crystallized from ethyl acetate/ether/hexane to yield colorless crystals with m.p. 160–162° C.

4.) 5-Fluoro-N-[(4-pyridyl)methyl]-1-[(3-thiocarbamoyl-phenyl)methyl]-1H-indole-2-carboxamide This thioamide was obtained by reaction of the above nitrile with hydrogen sulfide as described in example 1/4 for the desfluoro analog. It was obtained as a yellow crystalline solid from acetone with m.p. 220–223° C.

5.) 4-({[1-(3-Amidino-benzyl)-5-fluoro-1H-indole-2-carbonyl]-amino}-methyl)-1-methyl-pyridinium trifluoroacetate trifluoroacetic acid salt This compound was similarly prepared by treatment of 5-fluoro-N-[(4-pyridyl)methyl]-1-[(3-thiocarbamoyl-phenyl)methyl]-1H-indole-2-carboxamide with methyl iodide and subsequently with ammonium acetate as described in example 1/5. The product was purified by HPLC and had a retention time of 16.64 min and the correct molecular weight.

Example 8

4-(2-{[1-(3-Amidino-benzyl)-1H-indole-2-carbonyl]-amino}-ethyl)-1-methyl-pyridinium trifluoroacetate trifluoroacetic acid salt

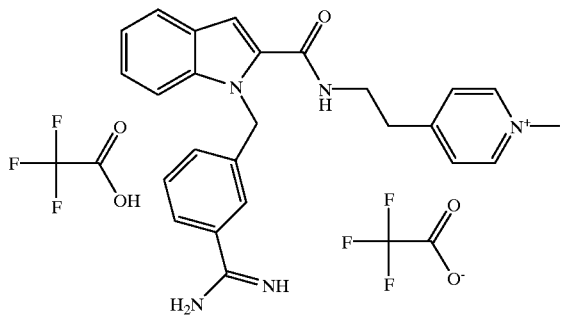

1.) 1-(3-Cyano-benzyl)-N-[2-(4-pyridyl)ethyl]-1H-indole-2-carboxamide 1-(3-Cyano-benzyl)-1H-indole-2-carboxylic acid (example 1/2), 280 mg, was converted to the acid chloride by means of thionyl chloride as described in example 1/3. This acid chloride was added to a mixture of 300 mg of 2-(4-pyridyl)ethylamine dihydrochloride and 0.4 ml of diisopropylethylamine in methylene chloride. After stirring for 10 minutes, the mixture was layered with 10% aqueous sodium carbonate and stirred for additional 10 minutes. The organic layer was dried and evaporated and the residue was chromatographed over 12 g of silica gel using methylene chloride/acetone 1:1 to yield 280 mg of resinous product.

2.) N-[2-(4-Pyridyl)ethyl]-1-[(3-thiocarbamoyl-phenyl)methyl]-1H-indole-2-carboxamide The above 1-(3-cyano-benzyl)-N-[2-(4-pyridyl)ethyl]-1H-indole-2-carboxamide was reacted with hydrogen sulfide as described in example 1/4. Crystallization from acetone/hexane gave 290 mg of yellowish crystals with m.p. 208–210° C.

3.) 4-(2-{[1-(3-Amidino-benzyl)-1H-indole-2-carbonyl)-amino}-ethyl)-1-methyl-pyridinium trifluoroacetate trifluoroacetic acid salt A mixture of 250 mg of N-[2-(4-pyridyl)ethyl]-1-[(3-thiocarbamoyl-phenyl)methyl]-1H-indole-2-carboxamide, 2 ml of dimethylsulfoxide, 10 ml of acetone, and 1 ml of methyl iodide was stirred in a sealed vial for 20 hours. The reaction mixture was diluted with toluene and evaporated. The residue was dissolved in acetone and the product was precipitated with ether. The solvents were decanted and the residue was reprecipitated from methanol with ether. The solids were separated and dried in vacuum. This material was dissolved in 25 ml of methanol and the solution was treated with 0.4 ml of acetic acid and 0.8 g of ammonium acetate. The mixture was heated to 55–60° C. for 2 hours in a sealed vial. The solvent was evaporated and the bulk of the ammonium acetate was removed under high vacuum. The residue was lyophilized from acetonitrile/water 1:1 containing 1% of trifluoroacetic acid. Final purification by reverse phase HPLC gave the product with a retention time of 16.23 min and correct molecular weight.

Example 9

4-[({1-[3-(4-Amidino-phenyl)-2-propynyl]-1H-indole-2-carbonyl}-amino)-methyl]-1-methyl-pyridinium trifluoroacetate trifluoroacetic acid salt

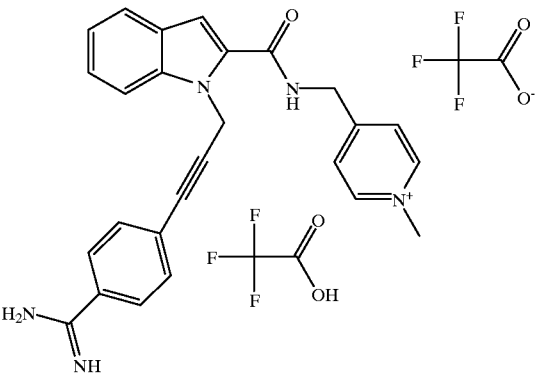

1.) 1-(2-Propynyl)-1H-indole-2-carboxylic acid methyl ester 1.25 g of potassium tert-butoxide was added to a solution of 1.75 g (10 mmol) of 1H-indole-2-carboxylic acid methyl ester in 20 ml of dimethylformamide cooled to 0° C. The mixture was stirred at this temperature for 10 minutes and treated with 2 ml of 80% solution of propargyl bromide in toluene. After stirring for 1 hour at room temperature, the mixture was poured into ice-water. The precipitated crystals were filtered off and dissolved in methylene chloride. The solution was dried and filtered over a plug of silica gel. The filtrate was evaporated and the residue was crystallized from hexane to yield 1.9 g of colorless crystals with m.p. 88–90° C.

2.) 1-(2-Propynyl)-1H-indole-2-carboxylic Acid

A mixture of 1.065 g (5 mmol) of 1-(2-propynyl)-1H-indole-2-carboxylic acid methyl ester, 30 ml of methanol, 3 ml of water, and 0.4 g of sodium hydroxide was heated to reflux for 40 minutes. The solvent was partially evaporated and the residue was acidified with acetic acid and diluted with water. The precipitate was filtered off and partitioned between methylene chloride/ether and 1 N hydrochloric acid. The organic phase was dried and evaporated and the residue was crystallized from methylene chloride/hexane to yield 0.87 g of colorless crystals with m.p. 190–193° C.

3.) 1-(2-Propynyl)-N-(4-pyridyl)methyl-1H-indole-2-carboxamide

A mixture of 0.5 g of the above 1-(2-propynyl)-1H-indole-2-carboxylic acid, 20 ml of methylene chloride, and 3 ml of thionyl chloride was heated to reflux for 3 hours. The solvent and excess reagent were evaporated, at the end azeotropically with hexane. The residue was dissolved in methylene chloride and added to a solution of 0.45 ml of 4-aminomethylpyridine in methylene chloride. The mixture was layered with 10% aqueous sodium carbonate and stirred for 15 minutes at room temperature. The organic layer was dried and evaporated and the residue was passed over 15 g of silica gel using methylene chloride/ethyl acetate 1:1 for elution. Crystallization from acetone/hexane gave 410 mg of crystals with m.p. 147–148° C.

4.) 1-{3-[4-(N-tert-butoxycarbonyl-amidino)phenyl]-2-propynyl}-N-[(4-pyridyl)methyl]-1H-indole-2-carboxamide A mixture of 290 mg (1 mmol) of the above 1-(2-propynyl)-N-(4-pyridyl)methyl-1H-indole-2-carboxamide, 350 mg (1 mmol) of 4-(N-tert-butoxycarbonyl-amidino)iodobenzene, 15 ml of acetonitrile, 1 ml of triethylamine, and 10 mg of cuprous iodide was degassed with nitrogen. Palladium bistriphenylphosphine dichloride, 20 mg, was then added and the mixture was stirred in a sealed vial at room temperature for 18 hours. The solvent was evaporated and the residue was partitioned between methylene chloride and 10% aqueous sodium carbonate solution. The organic layer was dried and evaporated and the residue was chromatographed over 15 g of silica gel using methylene chloride/acetone 1:1 for elution. The combined homogeneous fractions were evaporated to leave 225 mg of yellowish resin which was used in the next step.

The 4-(N-tert-butoxycarbonyl-amidino)iodobenzene required for the coupling reaction was obtained as follows.

4-Iodothiobenzamide

A mixture of 2.1 g of 4-iodobenzamide, 30 ml of tetrahydrofuran, and 2 g of Lawesson's reagent was heated to reflux for 1 hour. It was partitioned between toluene and 10% aqueous sodium carbonate solution. The organic phase was dried and evaporated. The crude product was passed over a plug of silica gel using acetone/hexane 1:1 for elution. Crystallization from methylene chloride/hexane gave 1.75 g of yellow crystals with m.p. 163–165° C.

4-(N-tert-butoxycarbonyl-amidino)iodobenzene

A mixture of the above 4-iodothiobenzamide 20 ml of acetone and 0.7 ml of methyl iodide was stirred at room temperature for 18 hours. The precipitated crystals were collected and washed with ether to leave 2.7 g of yellow crystals of the iodide salt of the S-methylated thiobenzamide with m.p. 213–215° C. (dec.).

A mixture of 2.43 g (6 mmol) of this iodide salt, 1 ml of acetic acid, 50 ml of methanol, and 5 g of ammonium acetate was stirred at room temperature for 24 hours. The solvent was evaporated and the residue was stirred with 10% aqueous sodium carbonate solution and 1 N sodium hydroxide. The precipitated crystals were collected and dried to leave 1.8 g of 4-iodobenzamidine.

Part of this material, 1 g, was dissolved in 20 ml of acetonitrile and stirred with 1 g of di-tert-butyl-dicarbonate and 5 ml of 10% aqueous sodium carbonate solution for 1 hour at room temperature. The mixture was partitioned between methylene chloride and water. The organic phase was dried and evaporated and the residue was crystallized from 2-propanol/water to leave 0.95 g of product with m.p. ca. 185–190° C. (dec.) and resolidification with m.p. >260° C.

5.) 4-[({1-[3-(4-Amidino-phenyl)-2-propynyl]-1H-indole-2-carbonyl}-amino)-methyl]-1-methyl-pyridinium trifluoroacetate trifluoroacetic acid salt A mixture of 125 mg of 1-{3-[4-(N-tert-butoxycarbonyl-amidino)phenyl]-2-propynyl]-N-[(4-pyridyl)methyl]-1H-indole-2-carboxamide, 5 ml of acetone, and 0.4 ml of methyl iodide was heated to 55° C. for 30 min. The solvent and excess reagent were evaporated and the residue was stirred with ether. The solids were collected and dried to leave 130 mg of product. Part of the material, 70 mg, was combined with 2 ml of methylene chloride and 2 ml of trifluoroacetic acid. After sitting at room temperature for 15 minutes, the solvents were evaporated and the residue was dissolved in 2-propanol and the solution was filtered. The filtrate was evaporated and the residue was stirred with ether. The separated solids were collected and dried to yield 75 mg of the title compound which had a HPLC retention time of 17.3 min and the correct molecular weight.

Example 10

4-({N-[1-(3-Amidino-benzyl)-1H-indole-2-carbonyl]-N-(methoxycarbonylmethyl)-amino}-methyl)-1-methyl-pyridinium trifluoroacetate trifluoroacetic acid salt

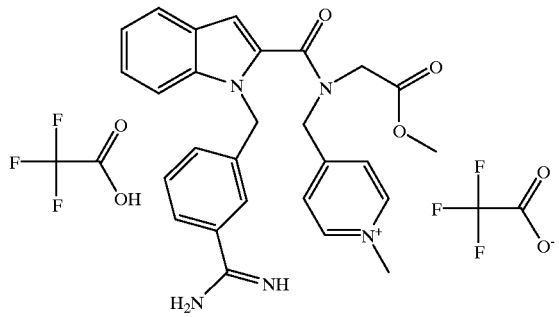

1.) N-(4-Pyridylmethyl)glycine methyl ester dihydrochloride

A mixture of glycine methyl ester hydrochloride (2.5 g, 20 mmol), 10 ml of acetic acid, 20 ml of 2-propanol, and 1.8 g (17 mmol) of 4-pyridinecarboxaldehyd was stirred at room temperature for 15 minutes. 1 g of sodium borohydride was added in small portions over a period of 15 minutes. After addition, the mixture was stirred for another 30 minutes and was then diluted with methylene chloride and made alkaline by addition of conc. ammonia and 1 N sodium hydroxide solution. The organic phase was dried and evaporated. The residue was dissolved in methanol and the solution was treated with 4 N hydrogen chloride in dioxane. The separated crystals were collected, washed with ethanol and ether, and dried to give 1.72 g of product with m.p. 194–196° C. (dec.).

2.) 1-(3-Cyano-benzyl)-N-(methoxycarbonylmethyl)-N-(4-pyridylmethyl)-1H-indole-2-carboxamide 280 mg of 1-(3-cyano-benzyl)-1H-indole-2-carboxylic acid was converted to the acid chloride by means of thionyl chloride as described in example 1/3. This acid chloride was added to a mixture of 340 mg (1.5 mmol) of N-(4-pyridylmethyl)glycine methyl ester dihydrochloride and 0.4 ml of diisopropylethylamine in 20 ml of methylene chloride. After stirring for 10 minutes, the mixture was layered with 10% aqueous sodium carbonate and stirred for additional 10 minutes. The organic layer was dried and evaporated and the residue was chromatographed over 13 g of silica gel using methylene chloride/acetone 1:1 to yield 300 mg of resinous product.

3.) N-(Methoxycarbonylmethyl)-N-(4-pyridylmethyl)-1-[(3-thiocarbamoyl-phenyl)methyl]-1H-indole-2-carboxamide 300 mg of the above resinous 1-(3-cyano-benzyl)-N-(methoxycarbonylmethyl)-N-(4-pyridylmethyl)-1H-indole-2-carboxamide was dissolved in 6 ml of pyridine and 3 ml of triethylamine. The solution was saturated with hydrogen sulfide while cooled in ice-water. After stirring at room temperature over night, the solvents were evaporated and the residue was dissolved in acetone and the product was precipitated by addition of ether and hexane. The solvents were removed and the solids were dried in vacuum to yield ca. 300 mg of yellow amorphous powder, which was further reacted without purification.

4.) 4-({N-[1-(3-Amidino-benzyl)-1H-indole-2-carbonyl]-N-(methoxycarbonylmethyl)-amino}-methyl)-1-methyl-pyridinium trifluoroacetate trifluoroacetic acid salt A mixture of 300 mg crude N-(methoxycarbonylmethyl)-N-(4-pyridylmethyl)-1-[(3-thiocarbamoyl-phenyl)methyl]-1H-indole-2-carboxamide, 10 ml of acetone, and 0.8 ml of methyl iodide was stirred in a sealed vial for 20 hours. The reaction mixture was diluted with toluene and evaporated. The residue was dissolved in acetone and the product was precipitated with ether. The solvents were decanted and the residue was stirred with fresh acetone/ether. The solids were separated and dried in vacuum. This material was dissolved in 20 ml of methanol and the solution was treated with 0.3 ml of acetic acid and 0.6 g of ammonium acetate. The mixture was heated to 55° C. for 2.5 hours in a sealed vial. The solvent was evaporated and the bulk of the ammonium acetate was removed under high vacuum. The residue was lyophilized from acetonitrile/water 1:1 containing 1% of trifluoroacetic acid. Final purification by reverse phase HPLC gave the product with a retention time of 16.75 min and correct molecular weight.

Example 11

4-({[1-(3-Amidino-benzyl)-3-methoxycarbonyl-1H-indole-2-carbonyl]-amino}-methyl)-1-methyl-pyridinium trifluoroacetate trifluoroacetic acid salt

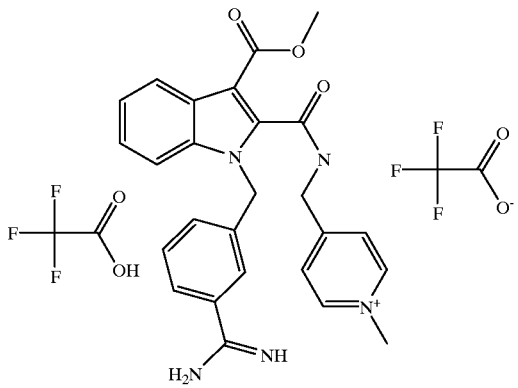

1.) 1-(3-Cyano-benzyl)-1H-indole-2,3-dicarboxylic acid dimethyl ester

A solution of 0.47 g (2 mmol) of 1H-indole-2,3-dicarboxylic acid dimethyl ester in 10 ml of dimethylformamide was treated with 0.23 g (2 mmol) of potassium tert-butoxide. After stirring for 5 minutes, 0.4 g (2 mmol) of 3-cyano-benzyl bromide was added and the mixture was heated to 95° C. After cooling, the mixture was partitioned between methylene chloride/hexane and aqueous sodium bicarbonate solution. The organic phase was dried and evaporated and the residue was chromatographed over 15 g of silica gel using 10% ether in methylene chloride for elution. The clean fractions were combined and evaporated to leave 0.6 g of colorless resin.

2.) 1-(3-Cyano-benzyl)-3-methoxycarbonyl-1H-indole-2-carboxylic acid

A mixture of 0.4 g of the above 1-(3-cyano-benzyl)-1H-indole-2,3-dicarboxylic acid dimethyl ester, 20 ml of methanol, 2 ml of water, and 0.4 g of sodium hydroxide was heated to reflux for 5 minutes. The solvent was partially removed and the residue was diluted with water and acidified with 2 N hydrochloric acid. The precipitated acid was extracted with methylene chloride. The extracts were dried and evaporated. Crystallization of the residue from methylene chloride/ether/hexane gave 370 mg of colorless crystals.

3.) 1-(3-Cyano-benzyl)-3-methoxycarbonyl-N-(4-pyridylmethyl)-1H-indole-2-carboxamide A mixture of 200 mg of 1-(3-cyano-benzyl)-3-methoxycarbonyl-1H-indole-2-carboxylic acid, 110 mg of 4-aminomethylpyridine, 210 mg of diphenylphosphoryl azide, 4 ml of dimethylformamide, and 0.3 ml of diisopropylethylamine was allowed to sit at room temperature for 18 hours. The solvent was evaporated and the residue was partitioned between methylene chloride and 10% aqueous sodium carbonate. The organic layer was dried and evaporated and the residue was chromatographed over 12 g silica gel using methylene chloride/ethyl acetate/acetone 2:2:1 for elution. Crystallization from ethyl acetateether/hexane gave 170 mg of colorless crystals with m.p. 152–154° C.

4.) 3-Methoxycarbonyl-N-[(4-pyridyl)methyl]-1-[(3-thiocarbamoyl-phenyl)methyl]-1H-indole-2-carboxamide A solution of 150 mg of 1-(3-cyano-benzyl)-3-methoxycarbonyl-N-(4-pyridylmethyl)-1H-indole-2-carboxamide in 4 ml of pyridine and 2 ml of triethylamine was cooled in ice-water and saturated with hydrogen sulfide. After sitting in a sealed vial for 4 hours at room temperature, the solvents were evaporated, at the end azeotropically with ethyl acetate. The residue was crystallized from methylene chloride/ether/hexane to leave 160 mg of light yellow product which was used in the subsequent step.

5.) 4-({[1-(3-Amidino-benzyl)-3-methoxycarbonyl-1H-indole-2-carbonyl]-amino}methyl)-1-methyl-pyridinium trifluoroacetate trifluoroacetic acid salt A mixture of 150 mg of 3-methoxycarbonyl-N-(4-pyridyimethyl)-1-[(3-thiocarbamoyl-phenyl)methyl]-1H-indole-2-carboxamide, 10 ml of acetone, 1 ml of dimethylsulfoxide, and 0.6 ml of methyl iodide was stirred at room temperature for 18 hours. It was then diluted with ethyl acetate and evaporated. The residue was stirred with ether and the solvent was decanted. The residue was precipitated from ethyl acetate with ether, collected and dried in vacuum. This material was dissolved in 15 ml of methanol, treated with 0.15 ml of acetic acid and 0.3 g of ammonium acetate, and heated at 55° C. for 2 hours. The solvent was evaported and the residue was lyophilized from water containing 1% of trifluoroacetic acid and acetonitrile (1:1). Purification by HPLC yielded the title compound with a retention time of 16.2 minutes and the correct molecular weight.

Example 12

4-({[1-(4-Amidino-benzyl)-1H-indole-2-carbonyl]-amino}-methyl)-1-methyl-pyridinium trifluoroacetate trifluoroacetic acid salt

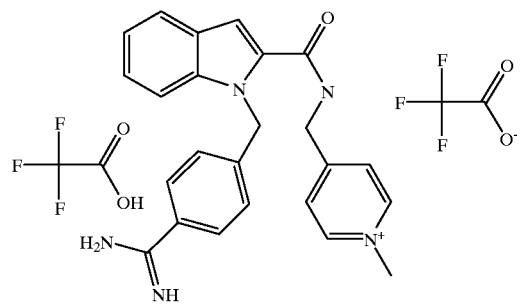

The starting material was prepared analogously to the 3-position isomer described in Example 1.

1.) 1-(4-Cyano-benzyl)-1H-indole-2-carboxylic acid ethyl ester

This compound was obtained as colorless crystals from methanol with m.p. 106–107° C. by alkylation of 1H-indole-2-carboxylic acid ethyl ester with 4-cyano-benzyl bromide.

2.) 1-(4-Cyano-benzyl)-1H-indole-2-carboxylic acid

This compound was prepared by alkaline hydrolysis of the above ester with methanol and aqueous sodium hydroxide. Crystallization from methylene chloride/hexane yielded colorless crystals with m.p. 185–187° C.

3.) 1-(4-Cyano-benzyl)-N-(4-pyridylmethyl)-1H-indole-2-carboxamide

This compound was obtained by reaction of the above acid with thionyl chloride and subsequently with 4-aminomethylpyridine and purified by chromatography over silica gel using methylene chloride/acetone 1:1. Crystallized from ethyl acetate/hexane, the colorless crystals had m.p. 128–131° C.

4.) N-[(4-Pyridyl)methyl]-1-[(4-thiocarbamoyl-phenyl)methyl]-1H-indole-2-carboxamide This compound resulted from reaction of the above nitrile with hydrogen sulfide and was obtained as yellowish crystals from acetone/ethyl acetate/ether with m.p. 176–180° C. (dec.).

5.) 4-({[1-(4-Amidino-benzyl)-1H-indole-2-carbonyl]-amino}-methyl)-1-methyl-pyridinium trifluoroacetate trifluoroacetic acid salt This compound was prepared following the procedure of Example 1/5 by reacting N-(4-pyridylmethyl)-1-[(4-thiocarbamoyl-phenyl)methyl]-1H-indole-2 -carboxamide with methyl iodide and subsequently with ammonium acetate. The product was purified by HPLC and had retention time of 15.4 minutes and the correct molecular weight.

Example 13

1-[4-Amidino-benzyl]-1H-indole-2-carboxylic acid ethyl ester hydrochloride

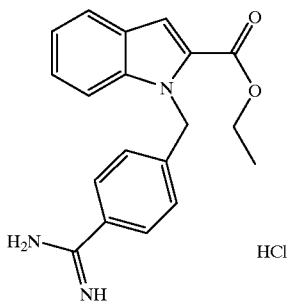

1.) 1-(4-Thiocarbamoyl-phenyl)methyl-1H-indole-2-carboxylic acid ethyl ester

A solution of 300 mg of 1-(4-cyano-benzyl)-1H-indole-2-carboxylic acid ethyl ester in 8 ml of pyridine and 4 ml of triethylamine was saturated with hydrogensulfide while cooled in ice water. After sitting at room temperature over night in a sealed vial, the reaction mixture was partitioned between toluene and 10% aqueous sodium carbonate. The organic phase was dried and evaporated. Crystallization of the residue from ether yielded 0.3 g of yellow crystals with m.p. 187–189° C.

2.) 1-[4-Amidino-benzyl]-1H-indole-2-carboxylic acid ethyl ester hydrochloride

A mixture of 250 mg of 1-(4-thiocarbamoyl-phenyl)methyl-1H-indole-2-carboxylic acid ethyl ester, 10 ml of acetone, and 1 ml of methyl iodide was stirred at room temperature for 20 hours. The precipitated crystals were filtered off, washed with ether, and dissolved in 10 ml of methanol. The solution was treated with 0.2 ml of acetic acid and 0.5 g of ammonium acetate and stirred at room temperature for 18 hours. The solvent was evaporated and the residue was partitioned between methylene chloride/2-propanol and 1 N sodium hydroxide solution. The organic phase was dried and evaporated. The residue was treated with hydrogen chloride in ether and crystallized from ethanol/ether to leave colorless crystals with m.p. 240–241° C.

Example 14

1-[3-Amidino-benzyl]-1H-indole-2-carboxylic acid ethyl ester hydrochloride

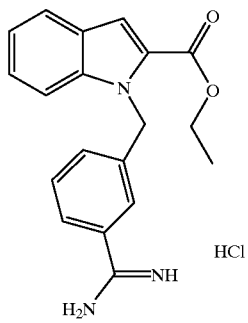

1.) 1-(3-Thiocarbamoyl-phenyl)methyl-1H-indole-2-carboxylic acid ethyl ester

This compound was obtained by the standard reaction (see example 13/1) of 1-(3-cyano-benzyl)-1H-indole-2-carboxylic acid ethyl ester (example 1/1) with hydrogen sulfide. It was crystallized from ether/hexane to give yellow crystals with m.p. 124–126° C.

2.) 1-[3-Amidino-benzyl]-1H-indole-2-carboxylic acid ethyl ester hydrochloride

This compound was prepared similarly to example 13/2 by reaction of 1-(3-thiocarbamoyl-phenyl)methyl-1H-indole-2-carboxylic acid ethyl ester with methyl iodide and subsequently with ammonium acetate. The hydrochloride was crystallized from 2-propanol/ethyl acetate/ether to give colorless solvated crystals with m.p. 136–140° C. (dec.). This compound had a HPLC retention time of 23.95 minutes and the correct molecular weight.

Example 15

1-[3-Amidino-benzyl]-5-fluoro-1H-indole-2-carboxylic acid methyl ester hydrochloride

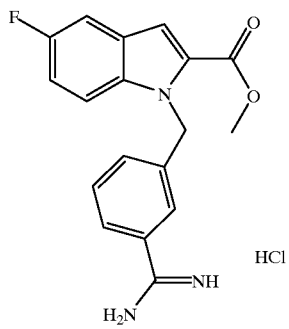

The starting material 5-fluoro-1-(3-thiocarbamoyl-phenyl)methyl-1H-indole-2-carboxylic acid methyl ester was similarly to example 13/1 obtained from the reaction of 1-(3-cyanobenzyl)-5-fluoro-1H-indole-2-carboxylic acid methyl ester (example 7/1) with hydrogen sulfide. It was crystallized from ether/hexane to give a yellow crystalline powder which was directly converted to the amidine analogously to example 1/5.

The title compound was prepared analogously to example 1. The hydrochloride was crystallized from methanol/ether and gave colorless crystals with m.p. 235–237° C. (dec.).

Example 16

1-[3-Amidino-benzyl]-1H-indole-2,3-dicarboxylic acid dimethyl ester trifluoroacetic acid salt

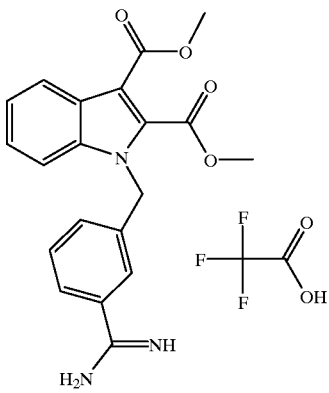

The starting material 1-(3-thiocarbamoylphenyl)methyl-1H-indole-2,3-dicarboxylic acid dimethyl ester was prepared analogously to example 13/1 by reacting 1-(3-cyano-benzyl)-1H-indole-2,3-dicarboxylic acid dimethyl ester (example 11/1) with hydrogen sulfide. It was crystallized from ether/hexane to give yellow crystals with m.p. 176–178° C.

The product was converted to the amidine analogously to example 115. The amidine was lyophilized from acetonitrile/water/trifluoroacetic acid and had a retention time on HPLC of 20.9 min and the correct molecular weight.

Example 17

[4-({[1-(3-Amidino-benzyl)-4-methoxy-1H-indole-2-carbonyl]-amino}-methyl)-phenyl]-trimethyl-ammonium trifluoroacetate trifluoroacetic acid salt

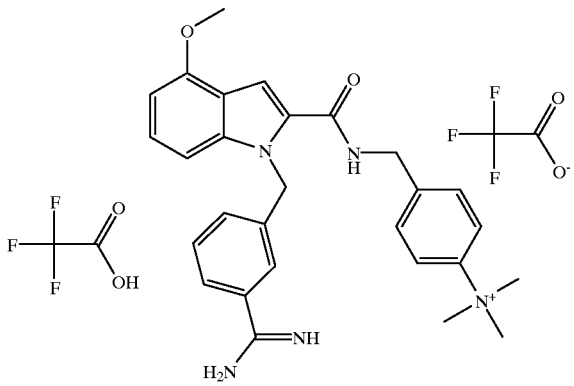

1.) 1-(3-Cyano-benzyl)-4-methoxy-1H-indole-2-carboxylic acid methyl ester

A solution of 1.025 g (5 mmol) of 4-methoxy-1H-indole-2-carboxylic acid methyl ester in 20 ml of dimethylformamide was treated with 0.6 g (5.25 mmol) of potassium tert-butoxide. The mixture was stirred at room temperature for 10 minutes to give a clear solution. 1 g (5 mmol) of 3-cyano-benzyl bromide was added and the mixture was slowly heated to 90° C., cooled, acidified with acetic acid, and poured on ice-water and stirred to crystallize. The crystals were filtered off, washed with water and dissolved in methylene chloride. The solution was washed with saturated sodium bicarbonate solution, dried and evaporated and the residue was crystallized from methanol to give 1.3 g of colorless crystals with m.p. 135–136° C.

2.) 1-(3-Cyano-benzyl)-4-methoxy-1H-indole-2-carboxylic acid

A mixture of 0.96 g (3 mmol) of the above 1-(3-cyano-benzyl)-4-methoxy-1H-indole-2-carboxylic acid methyl ester, 20 ml of methanol, 2 ml of water, and 0.5 g of sodium hydroxide was heated to reflux for 40 minutes. The mixture was diluted with water and extracted with ether/hexane. The aqueous phase was acidified with 2 N hydrochloric acid and extracted with methylene chloride. The extracts were dried and evaporated. Crystallization of the residue from methylene chloride/hexane gave 0.87 g of colorless crystals with m.p. 222–224° C. (dec.).

3.) 1-(3-Cyano-benzyl)-4-methoxy-N-[(4-dimethylaminophenyl)methyl]-1H-indole-2-carboxamide A mixture of 306 mg (1 mmol) of the above 1-(3-cyano-benzyl)-4-methoxy-1H-indole-2-carboxylic acid, 250 mg (1.12 mmol) of 4-(dimethylamino)benzylamine dihydrochloride, 350 mg of diphenylphosphoryl azide, 0.5 ml of diisopropylethylamine, and 5 ml of dimethylformamide was stirred at room temperature over night. The solvent was evaporated and the residue was partitioned between methylene chloride and 10% aqueous sodium carbonate solution. The organic layer was washed with dilute acetic acid and sodium bicarbonate, dried, and evaporated. The residue was passed over a plug of silica gel using 10% of ethyl acetate in dichloromethane. Crystallization from ethyl acetate/hexane yielded 330 mg (75%) of colorless crystals with m.p. 138–140° C.

4.) N-[(4-Dimethylaminophenyl)methyl]-4-methoxy-1-[(3-thiocarbamoyl-phenyl)methyl]-1H-indole-2-carboxamide Hydrogen sulfide was introduced for 15 minutes into an ice-water cooled solution of 200 mg of the above 1-(3-cyano-benzyl)-4-methoxy-N-[(4-dimethylaminophenyl)methyl]-1H-indole-2-carboxamide in 65 ml of pyridine and 3 ml of triethylamine. The mixture was stirred at room temperature for 18 hours in a sealed vial and then evaporated. The residue was passed over 10 g of silica gel using 20% of acetone in dichloromethane and crystallized from ethyl acetate/hexane to yield 150 mg (70%) of light yellow crystals with m.p. 192–193° C.

5.) [4-({[1-(3-Amidino-benzyl)-4-methoxy-1H-indole-2-carbonyl]-amino}-methyl)-phenyl]-trimethyl-ammonium trifluoroacetate trifluoroacetic acid salt A mixture of 125 mg of N-[4-(dimethylaminophenyl)methyl]-4-methoxy-1-[(3-thiocarbamoyl-phenyl)-methyl)-1H-indole-2-carboxamide, 10 ml of acetone, 1 ml of dimethylsulfoxide, and 0.6 ml of methyl iodide was stirred in a sealed vial for 24 hours at room temperature. The mixture was diluted with ethyl acetate and evaporated. The residue was stirred with acetoneether and the solvent was decanted. The residue was dissolved in a small amount of methanol and the product was precipitated with ether, collected, and dried. This material was dissolved in 15 ml of methanol and the solution was treated with 0.2 ml of acetic acid and 0.4 g of ammonium acetate. The mixture was heated at 55° C. for 3 hours in a sealed vial. The solvent was evaporated and the residue was lyophilized from acetonitrile and water containing 1% of trifluoroacetic acid. Purification by HPLC gave the title compound with retention time of 17.6 min and correct molecular weight.

Example 18

[4-({[1-(3-Amidino-benzyl)-6-methoxy-1H-indole-2-carbonyl]-amino}methyl)-phenyl]-trimethyl-ammonium trifluoroacetate trifluoroacetic acid salt

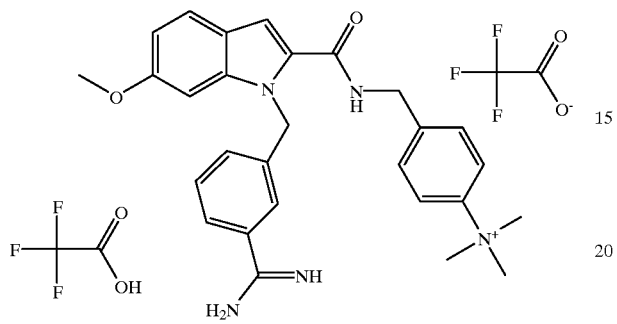

The starting material was prepared following the procedures described in Example 17.

1.) 1-(3-Cyano-benzyl)6-methoxy-1H-indole-2-carboxylic acid methyl ester

This compound was obtained in 86% yield by alkylation of 6-methoxy-1H-indole-2-carboxylic acid methyl ester with 3-cyano-benzyl bromide and had m.p. 152–153° C., crystallized from methanol.

2.) 1-(3-Cyano-benzyl)-6-methoxy-1H-indole-2-carboxylic acid

This compound was obtained in 91% yield by alkaline hydrolysis of the above methyl ester and had m.p. 225–227° C. (dec.), crystallized from dichloromethane/hexane.

3.) 1-(3-Cyano-benzyl)-N-[(4-dimethylaminophenyl) methyl]-6-methoxy-1H-indole-2-carboxamide This compound was prepared in 78% yield by coupling of the above acid with 4-dimethylaminobenzylamine using diphenylphosphoryl azide and had m.p. 156–158° C., crystallized from ethyl acetate/hexane.

4.) N-[(4-Dimethylaminophenyl)methyl]-6-methoxy-1-[(3-thiocarbamoyl-phenyl)methyl]-1H-indole-2-carboxamide This compound was obtained in 93% yield by reaction of the above nitrile with hydrogen sulfide. It was crystallized from ethyl acetate/hexane to give yellow crystals with m.p. 190–192° C.

5.) [4-({[1-(3-Amidino-benzyl)-6-methoxy-1H-indole-2-carbonyl]-amino}-methyl)-phenyl]-trimethyl-ammonium trifluoroacetate trifluoroacetic acid salt A mixture of 150 mg of N-[4-(dimethylaminophenyl) methyl]-6-methoxy-1-[(3-thiocarbamoyl-phenyl)-methyl]-1H-indole-2-carboxamide, 10 ml of acetone, 1 ml of dimethylsulfoxide, and 0.7 ml of methyl iodide was stirred in a sealed vial for 20 hours at room temperature. The mixture was diluted with ethyl acetate and evaporated. The residue was dissolved in acetone/ethyl acetate and precipitated with ether. The solvent was decanted and the residue was dissolved in a small amount of methanol and the product was precipitated with ether, collected, and dried. This material was dissolved in 20 ml of methanol and the solution was treated with 0.2 ml of acetic acid and 0.4 g of ammonium acetate. The mixture was heated at 55° C. for 2.5 hours in a sealed vial. The solvent was evaporated and the residue was lyophilized from acetonitrile and water containing 1% of trifluoroacetic acid. Purification by HPLC gave the title compound with retention time of 17.5 min and correct molecular weight.

Example 19

1-(3-Amidino-benzyl)-1H-indole-3-carboxylic acid 4-(dimethylamino)-benzyl amide trifluoroacetic acid salt

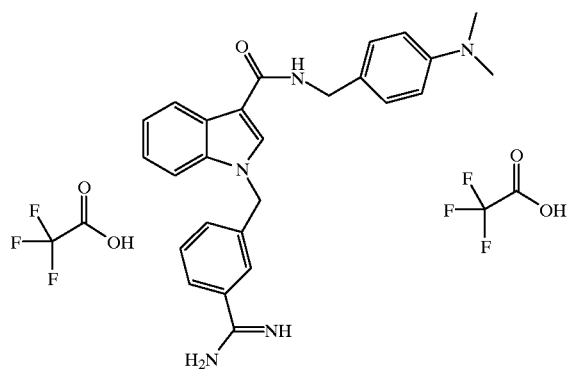

1.) 1-(3-Cyano-benzyl)-1H-indole-3-carboxylic acid

To a solution of 9 g (0.055 mol) 3-indolecarboxylic acid in 200 ml of tetrahydrofuran 3 g (0.122 mol) of sodium hydride was added at 0° C. in portions. After 75 minutes at 0° C. 10.7 g (0.055 mol) 3-cyano-benzyl bromide was added. After 16 h stirring at room temperature the precipitate was filtered off, dissolved in water, and precipitated by addition of hydrochloric acid to give 13 g (86%) of the desired product. M.p. 226–228° C. MS: 277.2 (M+H$^+$).

2.) 1-(3-Cyano-benzyl)-1H-indole-3-carboxylic acid 4-(dimethylamino)-benzyl amide The compound was prepared from 1-(3-cyano-benzyl)-1H-indole-3-carboxylic acid, 4-dimethylaminobenzyl amine, diphenylphoshoryl azide and diisopropylethylamin as described in example 3/1. The crude material was purified by silica gel chromatography with toluene/ethyl acetate 5:1 to give the desired product in 32% yield. M.p. 126–128° C. MS: 409.3 (M+H$^+$).

3.) 1-(3-Amidino-benzyl)-1H-indole-3-carboxylic acid 4-(dimethylamino)-benzyl amide trifluoroacetic acid salt Into a solution of 250 mg (0.612 mmol) 1-(3-cyano-benzyl)-1H-indole-3-carboxylic acid 4-dimethylamino-benzyl amide in 10 ml of ethanol hydrogen chloride gas was bubbled in at 0° C. for 4 hours. The mixture was warmed up to room temperature overnight and evaporated. The residue was dissolved in 10 ml ethanol and liquid ammonia was added. The mixture was allowed to warm up to room temperature with stirring and evaporated. The crude material was purified by reversed phase chromatography on RP$_{18}$ material with water/ethanol/trifluoroacetic acid 6.5:3.5:0.1 to give 180 mg (36%) of the desired product. M.p. 92–96° C. MS: 426.3 (M+H$^+$).

Example 20

[4-({[1-(3-Amidino-benzyl)-1H-indole-3-carbonyl]-amino}-methyl)-phenyl]-trimethyl-ammonium trifluoroacetate trifluoroacetic acid salt

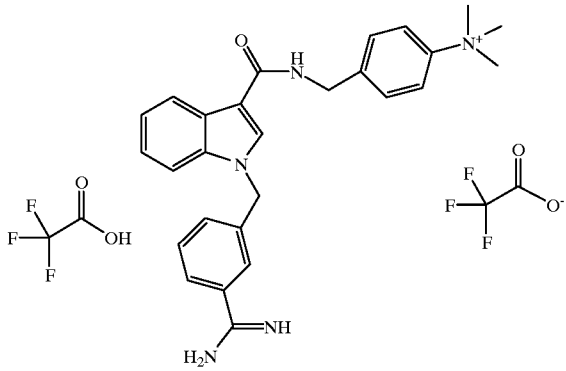

1.) [4-({[1-(3-Cyano-benzyl)-1H-indole-3-carbonyl]-amino}-methyl)-phenyl]-trimethyl-ammonium iodide To a solution of 250 mg (0.611 mmol) 1-(3-cyano-benzyl)-1H-indole-3-carboxylic acid (4-dimethylaminobenzyl)-amide (example 19/2) in 20 ml of acetone 384 μl (6.11 mmol) of methyl iodide was added and it was stirred for 4 days at room temperature. The mixture was evaporated to give 350 mg (quantitative yield) of the desired product. MS: 423.2 ($M^+$).

2.) [4-({[1-(3-Amidino-benzyl)-1H-indole-3-carbonyl]-amino}-methyl)-phenyl]-trimethyl-ammonium trifluoroacetate trifluoroacetic acid salt This compound was prepared from (4-({[1-(3-cyano-benzyl)-1H-indole-3-carbonyl]-amino}-methyl)-phenyl]-trimethyl-ammonium iodide by using hydrogen chloride and liquid ammonia as described in example 19/3. The crude material was purified by reversed phase chromatography on $RP_{18}$ material with water/ethanol/trifluoroacetic acid 7:3:0.1 to give the desired product in 39% yield. M.p. 177° C. (dec.). MS: 440.3 ($M^+$).

Example 21

(R)-1-(3-Amidino-benzyl)-5-benzyloxy-1H-indole-2-carboxylic acid (1-phenyl-ethyl)-amide acetic acid salt

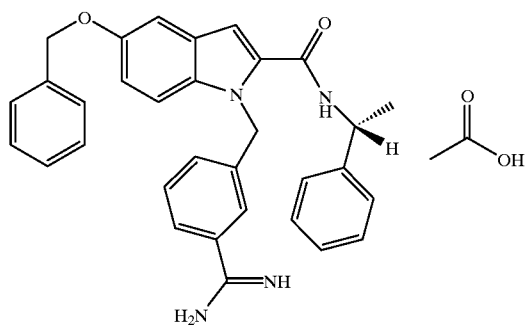

1.) 5-Benzyloxy-1-(3-cyano-benzyl)-1H-indole-2-carboxylic acid ethyl ester 10 g (0.034 mol) of 5-benzyloxy-1H-indole-2-carboxylic acid ethyl ester was dissolved in 100 ml dimethylformamide and 976 mg (0.04 mol) of sodium hydride was added portionwise. After 1 hour stirring at room temperature 797 mg (0.04 mol) of 3-cyano-benzyl bromide was added. The mixture was stirred at room temperature for 1.5 hours, neutralized with 2 N hydrochloric acid, and extracted with methyl tert-butyl ether. The organic phase was dried and evaporated. The crude material was purified by flash chromatography on silica gel with heptane/methyl tert-butyl ether 12:8 to give the desired product in 84% yield. M.p. 98–102° C. MS: 411.2 ($M+H^+$).

2.) 5-Benzyloxy-1-(3-cyano-benzyl)-1H-indole-2-carboxylic acid

This compound was prepared from 5-benzyloxy-1-(3-cyano-benzyl)-1H-indole-2-carboxylic acid ethyl ester and sodium hydroxide as described in example 1/2. The crude material was purified by flash chromatography on silica gel with dichloromethane/methanol 19:0.25 to give the desired product in 83% yield.

$^1$H-NMR (DMSO-$d_6$, 200 MHz): δ=5.11 (s, 2H, OCH$_2$); 5.88 (s, 2H, N—CH$_2$); 7.04 (dd, 1H, aromatic H); 7.20–7.60 (m, 11H, aromatic H); 7.70 (d, 1H, aromatic H). MS: 383.2 ($M+H^+$).

3.) (R)-5-Benzyloxy-1-(3-cyano-benzyl)-1H-indole-2-carboxylic acid (1-phenyl-ethyl)amide This compound was prepared from 5-benzyloxy-1-(3-cyano-benzyl)-1H-indole-2-carboxylic acid and (R)-1-phenyl-ethyl-amine by using diphenylphosphoryl azide and diisopropylethylamine as described in example 3/1. The crude material was purified by flash chromatography on silica gel with dichloromethane to give the desired product in 73% yield. M.p. 169–170° C. MS: 486.3 ($M+H^+$).

4.) (R)-5-Benzyloxy-1-(3-thiocarbamoyl-benzyl)-1H-indole-2-carboxylic acid (1-phenyl-ethyl)amide The compound was prepared from (R)-5-benzyloxy-1-(3-cyano-benzyl)-1H-indole-2-carboxylic acid (1-phenyl-ethyl)-amide and hydrogen sulfide as described in example 1/4 to give the desired product in 55% yield. M.p. 146–148° C. MS: 520.3 ($M+H^+$).

5.) (R)-1-(3-Amidino-benzyl)-5-benzyloxy-1H-indole-2-carboxylic acid (1-phenyl-ethyl)-amide acetic acid salt This compound was prepared from (R)-5-benzyloxy-1-(3-thiocarbamoyl-benzyl)-1H-indole-2-carboxylic acid (1-phenyl-ethyl)-amide, methyl iodide, and ammonium acetate as described in example 1/5, but for the methylation acetone was used as solvent and in the last step methanol and acetone were used as solvents. The crude material was purified by flash chromatography on silica gel with dichloromethane/methanol/acetic acid 9:0.25:0.5 to give the desired product in 28% yield. M.p. 72° C. (dec.). MS: 503.3 ($M+H^+$).

Example 22

1-(3-Amidino-benzyl)-1H-indole-2-carboxylic acid benzyl amide acetic acid salt

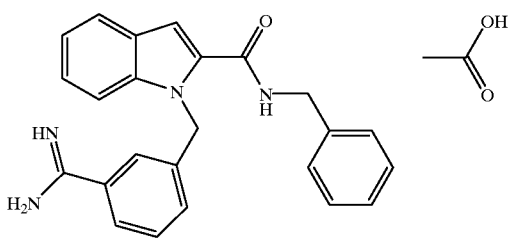

1.) 1-(3-Cyano-benzyl)-1H-indole-2-carboxylic acid benzyl amide

This compound was prepared from 1-(3-cyano-benzyl)-1H-indole-2-carboxylic acid (example 1/2) and benzylamine by using diphenylphosphoryl azide and diisopropylethylamine as described in example 3/1. The crude material was purified by flash chromatography on silica gel with toluene/ethanol 19:0.5 to give the desired product in 97% yield. M.p. 129–131° C. MS: 366.2 (M+H$^+$).

2.) 1-(3-Amidino-benzyl)-1H-indole-2-carboxylic acid benzyl amide acetic acid salt This compound was prepared from 1-(3-cyano-benzyl)-1H-indole-2-carboxylic acid benzyl amide by using hydrogen chloride and liquid ammonia as described in example 19/2. The crude material was purified by reversed phase chromatography on RP$_{18}$ material with water/acetonitrile/ammonium acetate 6:4:0.1 to give the desired product in 40% yield. M.p. 266–268° C. (dec.). MS: 383.2 (M+H$^+$).

Example 23

(RS)-1-(3-Amidino-benzyl)-1H-indole-2-carboxylic acid α-(4-pyridyl)-benzyl amide trifluoroacetic acid salt

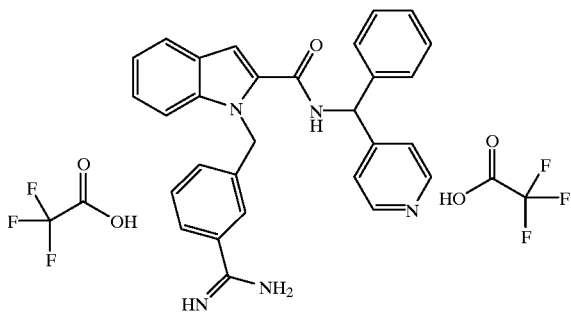

1.) (RS)-1-(3-Cyano-benzyl)-1H-indole-2-carboxylic acid α-(4-pyridyl)-benzyl amide This compound was prepared from 1-(3-cyano-benzyl)-1H-indole-2-carboxylic acid (example 1/2) and (RS)-α-(4-pyridyl)-benzyl amine by using diphenylphosphoryl azide and diisopropylethylamine as described in example 3/1. The crude material was purified by flash chromatography on silica gel with dichloromethanelethanol 19:0.25 to give the desired product in 43% yield. M.p. 90–110° C. MS: 443.2 (M+H$^+$).

2.) (RS)-1-(3-Amidino-benzyl)-1H-indole-2-carboxylic acid α-(4-pyridyl)benzyl amide trifluoroacetic acid salt This compound was prepared from (RS)-1-(3-cyano-benzyl)-1H-indole-2-carboxylic acid α-(4-pyridyl)-benzyl amide by using hydrogen chloride and liquid ammonia as described in example 19/3. The crude material was purified by reversed phase chromatography on RP$_{18}$ material with water/ethanol/trifluoroacetic acid 7:3:0.1 to give 13% of the desired product. M.p. 88–92° C. MS: 460.3 (M+H$^+$).

Example 24

(RS)-4-({[1-(3-Amidino-benzyl)-4-methoxy-1H-indole-2-carbonyl]-amino}-phenyl-methyl)-1-methyl-pyridinium trifluoroacetate trifluoroacetic acid salt

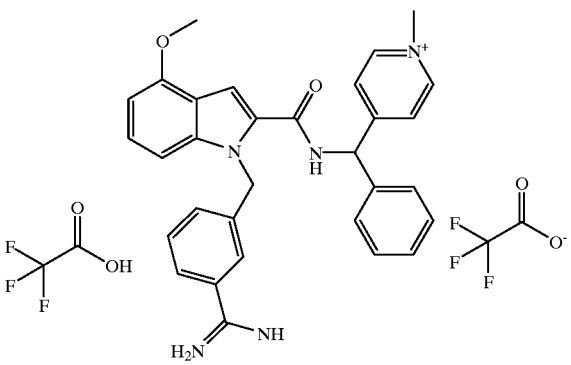

1.) (RS)-1-(3-Cyano-benzyl)-4-methoxy-1H-indole-2-carboxylic acid α-(4-pyridyl)-benzyl amide This compound was prepared from 1-(3-cyano-benzyl)-4-methoxy-1H-indole-2-carboxylic acid (example 17/2) and (RS)-α-(4-pyridyl)-benzyl amine by using diphenylphosphoryl azide and diisopropylethylamine as described in example 3/1. The crude material was purified by flash chromatography on silica gel with dichloromethane/methanol 19:0.3 to give the desired product in 18% yield. MS: 473.2 (M+H$^+$).

2.) (RS)-4-Methoxy-1-(3-thiocarbamoyl-benzyl)-1H-indole-2-carboxylic acid α-(4-pyridyl)benzyl amide The compound was prepared from (RS)-1-(3-cyano-benzyl)-4-methoxy-1H-indole-2-carboxylic acid α-(4-pyridyl)-benzyl amide and hydrogen sulfide as described in example 1/4 to give the desired product in 78% yield. MS: 507.1 (M+H$^+$).

5.) 4-({[1-(3-Amidino-benzyl)-4-methoxy-1H-indole-2-carbonyl]-amino}-phenyl-methyl)-1-methyl-pyridinium trifluoroacetate trifluoroacetic acid salt This compound was prepared from (RS)-4-methoxy-1-(3-thiocarbamoyl-benzyl)-1H-indole-2-carboxylic acid α-(4-pyridyl)-benzyl amide, methyl iodide, and ammonium acetate as described in example 1/5. The crude material was purified by flash chromatography on silica gel first using dichloromethane/methanol/trifluoroacetic acid 9:1:0.2 to give a product described in example 54 and second 5:1:0.2 to give the desired product (20% yield). M.p. 135° C. MS: 504.2 (M$^+$).

Example 25

1-(3-Amidino-benzyl)-4-methoxy-1H-indole-2-carboxylic acid (2-(4-hydroxy-phenyl)ethyl) amide trifluoroacetic acid salt

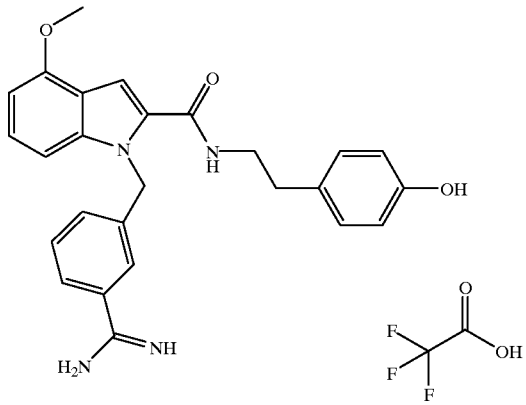

1.) 1-(3-Cyano-benzyl)-4-methoxy-1H-indole-2-carboxylic acid (2-(4-hydroxy-phenyl)ethyl)amide This compound was prepared from 1-(3-cyano-benzyl)-4-methoxy-1H-indole-2-carboxylic acid (example 17/2) and 4-(2-aminoethyl)-phenol by using diphenylphosphoryl azide and diisopropylethylamine as described in example 3/1. The crude material was purified by flash chromatography on silica gel with dichloromethane/methanol 19:0.1 to give the desired product as an oil in 74% yield. MS: 426 (M+H$^+$).

2.) 1-(3-Amidino-benzyl)-4-methoxy-1H-indole-2-carboxylic acid (2-(4-hydroxy-phenyl)ethyl)amide trifluoroacetic acid salt This compound was prepared from 1-(3-cyano-benzyl)-4-methoxy-1H-indole-2-carboxylic acid (2-(4-hydroxy-phenyl)-ethyl)-amide by using hydrogen chloride and liquid ammonia as described in example 19/3. The crude material was purified by reversed phase chromatography on RP$_{18}$ material with dichloromethane/methanol/trifluoroacetic acid 19:1.4:0.1 to give the desired product in 62% yield. M.p. 140–142° C. MS: 443.3 (M+H$^+$).

Example 26

1-(3-Amidino-benzyl)-1H-indole-2-carboxylic acid 3-amidino-benzyl ester trifluoroacetic acid salt

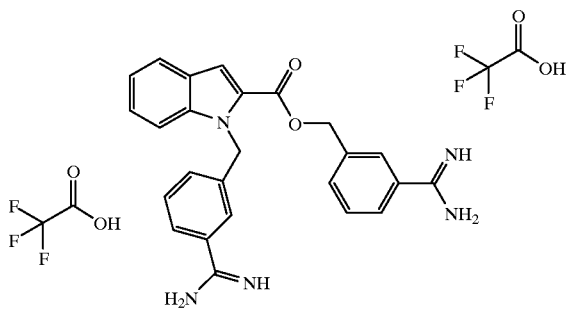

1.) 1-(3-Cyano-benzyl)-1H-indole-2-carboxylic acid 3-cyano-benzyl ester

This compound was prepared from 1H-indole-2-carboxylic ethyl ester and 3-cyano-benzyl bromide by using sodium hydride as described in example 21/1, but it was done at 100° C. instead of room temperature. The crude material was purified by flash chromatography on silica gel with heptane/ethylacetate 5:1 to give 67% of 1-(3-cyano-benzyl)-1H-indole-2-carboxylic acid ethyl ester (fraction 1) and 10% of the title compound (fraction 2). Yield: 10%. M.p. 119–120° C. MS: 392.1 (M+H$^+$).

2.) 1-(3-Amidino-benzyl)-1H-indole-2-carboxylic acid 3-amidino-benzyl ester trifluoroacetic acid salt This compound was prepared from 1-(3-cyano-benzyl)-1H-indole-2-carboxylic acid 3-cyano-benzyl ester by using hydrogen chloride and liquid ammonia as described in example 19/3. The crude material was purified by MPLC on RP$_{18}$ material with water/ethanol/trifluoroacetic acid 7:3:0.1 to give the desired product in 12% yield. M.p. 258° C. MS: 426.2 (M+H$^+$).

Example 27

(RS)-1-(3-Amidino-benzyl)-1H-indole-2-carboxylic acid ((6-chloro-2-naphthyl)-(1-methyl-piperidin-4-yl)-methyl)amide trifluoroacetic acid salt

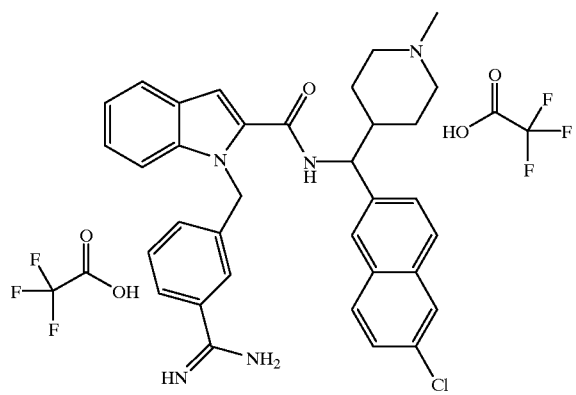

1.) (RS)-1-(3-Cyano-benzyl)-1H-indole-2-carboxylic acid ((6-chloro-2-naphthyl)-(1-methyl-piperidin-4-yl)-methyl) amide This compound was prepared from 1-(3-cyano-benzyl)-1H-indole-2-carboxylic acid (example 1/2) and (RS)-(6-chloro-2-naphthyl)-(1-methyl-piperidin4-yl)-methyl amine by using diphenylphosphoryl azide and diisopropylethylamine as described in example 3/1. The crude material was purified by flash chromatography on silica gel with dichloromethane/methanol 19:2 to give the desired product in 58% yield. M.p. 141–145° C. MS: 547.2 (M+H$^+$).

2.) (RS)-1-(3-Amidino-benzyl)-1H-indole-2-carboxylic acid ((6chloro-2-naphthyl)-(1-methyl-piperidin-4-yl)-methyl)amide trifluoroacetic acid salt This compound was prepared from (RS)-1-(3-cyano-benzyl)-1H-indole-2-carboxylic acid ((6-chloro-2-naphthyl)-(1-methyl-piperidin-4-yl)-methyl) amide by using hydrogen chloride and liquid ammonia as described in example 19/3. The crude material was purified by reversed phase chromatography on RP$_{18}$ material with water/ethanol/trifluoroacetic acid 5:5:0.1 to give the desired product in 31% yield. M.p. 110–120° C. MS: 564.2 (M+H$^+$).

Example 28

1-(3-Amidino-benzyl)-1H-indole-2-carboxylic acid 4-choro-benzyl amide trifluoroacetic acid salt

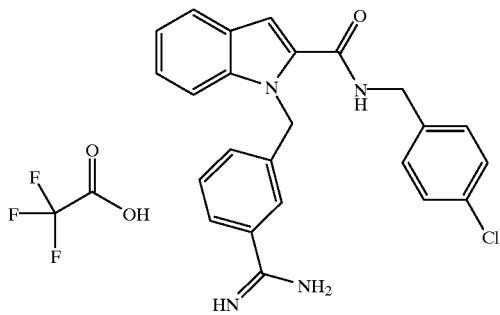

1.) 1-(3-Cyano-benzyl)-1H-indole-2-carboxylic acid 4-chloro-benzyl amide

This compound was prepared from 1-(3-cyano-benzyl)-1H-indole-2-carboxylic acid (example 1/2) and 4-chloro-benzyl amine by using diphenylphosphoryl azide and diisopropylethylamine as described in example 3/1. The crude material was purified by flash chromatography on silica gel with toluene/ethanol 19:0.065 to give the desired product in 80% yield. M.p. 147–149° C. MS: 400.1 (M+H$^+$).

2.) 1-(3-Amidino-benzyl)-1H-indole-2-carboxylic acid 4-chloro-benzyl amide trifluoroacetic acid salt This compound was prepared from 1-(3-cyano-benzyl)-1H-indole-2-carboxylic acid 4-chloro-benzyl amide by using hydrogen chloride and liquid ammonia as described in example 19/3. The crude material was purified by reversed phase chromatography on RP$_{18}$ material with water/ethanol/trifluoroacetic acid 7:3:0.1 to the desired product in 74% yield. M.p. 230° C. (dec.). MS: 439.3 (M+H$^+$).

Example 29

4-({[1-(3-Amidino-benzyl)-4-methyl-1H-indole-2-carbonyl]-amino}-methyl)-phenyl]-benzyl-dimethyl-ammonium trifluoroacetate trifluoroacetic acid salt

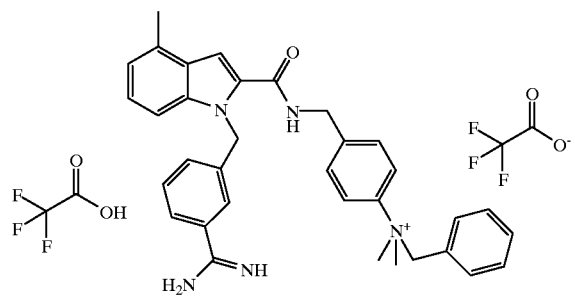

1.) 1-(3-Cyano-benzyl)-4-methyl-1H-indole-2-carboxylic acid ethyl ester

This compound was prepared from 4-methyl-1H-indole-2-carboxylic acid ethyl ester and 3-cyano-benzyl bromide by using sodium hydride as described in example 21/1 to give the desired product in 70% yield.

$^1$H-NMR (DMSO-d$_6$, 200 MHz): δ=1.29 (t, 3H, OCH$_2$CH$_3$); 2.52 (s, 3H, CH$_3$); 4.29 (q, 2H, OCH$_2$CH$_3$); 5.88 (s, 2H, N—CH$_2$); 6.97 (d, 1H, aromatic H); 7.12–7.32 (m, 2H, aromatic H); 7.34–7.55 (m, 4H, aromatic H); 7.69 (d, 1H, aromatic H).

2.) 1-(3-Cyano-benzyl)-4-methyl-1H-indole-2-carboxylic acid

This compound was prepared from 1-(3-cyano-benzyl)-4-methyl-1H-indole-2-carboxylic acid ethyl ester and sodium hydroxide as described in example 1/2 to give the desired product in 99% yield. M.p. 227–229° C. MS: 291.1 (M+H$^+$).

3.) 1-(3-Cyano-benzyl)-4-methyl-1H-indole-2-carboxylic acid (4-dimethylamino)-benzyl amide This compound was prepared from 1-(3-cyano-benzyl)-4-methyl-1H-indole-2-carboxylic acid and 4-(dimethylamino)-benzylamine by using diphenylphosphoryl azide and diisopropylethylamine as described in example 3/1. The crude material was purified by flash chromatography on silica gel with dichloromethane/methanol 19:0.05 to give the desired product in 78% yield.

$^1$H-NMR (DMSO-d$_6$, 200 MHz): δ=2.50 (s, 3H, CH$_3$); 2.85 (s, 6H, N(CH$_3$)$_2$); 4.32 (d, 2H, NH—CH$_2$); 5.92 (s, 2H, N—CH$_2$); 6.68 (m, 2H, AA'BB'-System); 6.91 (d, $_1$H, aromatic H); 7.09 (m, 2H, AA'BB'-System); 7.15 (m, 2H, aromatic H); 7.27–7.40 (m, 3H, aromatic H); 7.48 (t, 1H, aromatic H); 7.50 (s, 1H, aromatic H); 7.69 (d, 1H, aromatic H); 9.01 (t, 1H, NH).

4.) Benzyl-[4-({[1-(3-cyano-benzyl)-4-methyl-1H-indole-2-carbonyl]-amino}-methyl)-phenyl]-dimethyl-ammonium bromide This compound was prepared from 1-(3-cyano-benzyl)-4-methyl-1H-indole-2-carboxylic acid (4-dimethylamino)-benzyl amide and benzyl bromide as described in example 20/1 to give the desired product in 90% yield. MS: 513.3 (M$^+$).

5.) 4-({[1-(3-Amidino-benzyl)-4-methyl-1H-indole-2-carbonyl]-amino}-methyl)-phenyl]-benzyl-dimethyl-ammonium trifluoroacetate trifluoroacetic acid salt This compound was prepared from benzyl-[4-({[1-(3-cyano-benzyl)-4-methyl-1H-indole-2-carbonyl]-amino}-methyl)-phenyl]-dimethyl-ammonium bromide by using hydrogen chloride and liquid ammonia as described in example 19/3. The crude material was purified by reversed phase chromatography on RP$_{18}$ material with water/ethanol/trifluoroacetic acid 7:3:0.1 to give the desired product in 60% yield. M.p. 113° C. (dec.). MS: 530.2 (M$^+$).

Example 30

[4-({[1-(3-Amidino-benzyl)-5-fluoro-1H-indole-2-carbonyl]-amino}-methyl)-phenyl]-ethyl-dimethyl-ammonium trifluoroacetate trifluoroacetic acid salt

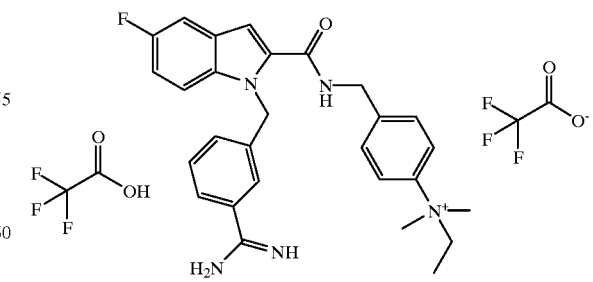

1.) 1-(3-Cyano-benzyl)-5-fluoro-1H-indole-2-carboxylic acid ethyl ester

This compound was prepared from 5-fluoro-1H-indole-2-carboxylic acid ethyl ester (5 g, 24 mmol), sodium hydride (695 mg, 29 mmol), 3-cyano-benzyl bromide (5.678 g, 29 mmol), and N,N-dimethylformamide (50 ml). The indole was dissolved in N,N-dimethylformamide and sodium hydride was added in portions and the reaction mixture was stirred for 90 min. Then the nitrile was added. After stirring for 3 h and standing overnight the mixture was partitioned between sodium bicarbonate solution (5% in water) and methyl tert-butyl ether. The organic layer was dried, evaporated, and purified by flash chromatography on silica gel with dichloromethane/heptane 1:1 to give 5.524 9 (71%) of the desired product. M.p. 94–96° C. MS: 323.1 (M+H$^+$).

2.) 1-(3-Cyano-benzyl)-5-fluoro-1H-indole-2-carboxylic acid

This compound was prepared from 1-(3-cyano-benzyl)-5-fluoro-1H-indole-2-carboxylic acid ethyl ester (5.48 g, 17 mmol), sodium hydroxide (7.9 g, 198 mmol), methanol (600 ml), and water (33.4 ml) analogously to example 1/2. The crude material obtained after drying and evaporating the organic layer was purified by flash chromatography on silica gel with dichloromethane/methanol 19:1 to give 4.679 9 (94%) of the desired product. M.p. 253° C. (dec.). MS: 295.0 (M+H$^+$).

3.) 1-(3-Cyano-benzyl)-5-fluoro-1H-indole-2-carboxylic acid (4-dimethylamino)-benzyl amide This compound was prepared from 1-(3-cyano-benzyl)-5-fluoro-1H-indole-2-carboxylic acid (1.0 g, 3.4 mmol), diphenylphosphoryl azide (955 μl, 1.3 equivalents), N,N-diisopropylethylamine (2.02 ml, 3.5 equivalents), 4-(dimethylamino)-benzylamine dihydrochloride (849 mg, 1.1 equivalents), and N,N-dimethylformamide (40 ml) as described in example 3/1. Purification was done by flash chromatography on silica gel with dichloromethane/methanol 19:0.1. Yield: 1.22 g (84%).

$^1$H-NMR (DMSO-d$_6$, 200 MHz): δ=2.85 (s, 6H, N(CH$_3$)$_2$); 4.32 (d, 2H, NH—CH$_2$); 5.91 (s, 2H, N—CH$_2$); 6.65 (m, 2H, AA'BB'-System); 7.13–7.00 (m, 2H, AA'BB'-System); 7.15 (d, 1H, aromatic H); 7.20 (s, 1H, aromatic H); 7.32 (d, 1H, aromatic H); 7.53–7.40 (m, 3H, aromatic H); 7.58 (m, 1H, aromatic H); 7.71 (m, 1H. aromatic H); 9.10 (t, 1H, NH).

4.) [4-({[1-(3-Cyano-benzyl)-5-fluoro-1H-indole-2-carbonyl]-amino}methyl)-phenyl]-ethyl-dimethyl-ammonium iodide This compound was prepared from 1-(3-cyano-benzyl)-5-fluoro-1H-indole-2-carboxylic acid (4-dimethylamino)-benzyl amide and ethyl iodide as described in example 20/1 to give the desired product in 74% yield. MS: 455.3 (M$^+$).

5.) [4-({[1-(3-Amidino-benzyl)-5-fluoro-1H-indole-2-carbonyl]-amino}-methyl)-phenyl]-ethyl-dimethyl-ammonium trifluoroacetate trifluoroacetic acid salt This compound was prepared from [4-({[1-(3-cyano-benzyl)-5-fluoro-1H-indole-2-carbonyl]-amino}-methyl)-phenyl]-ethyl-dimethyl-ammonium iodide by using hydrogen chloride and liquid ammonia as described in example 19/3. The crude material was purified by reversed phase chromatography on RP$_{18}$ material with water/ethanol/trifluoroacetic acid 7:3:0.1 to give the desired product in 28% yield. M.p. 73–75° C. (dec.). MS: 472.3 (M$^+$).

Example 31

1-(3-Amidino-benzyl)-5-fluoro-1H-indole-2-carboxylic acid (4-dimethylamino)-benzyl amide trifluoroacetic acid salt

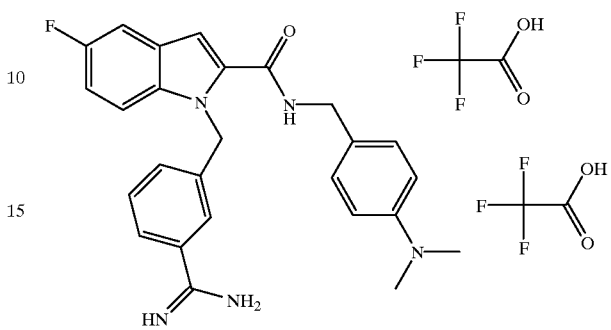

This compound was prepared from 1-(3-cyano-benzyl)-5-fluoro-1H-indole-2-carboxylic acid 4-(dimethylamino)-benzyl amide (example 30/3), hydrogen chloride, and liquid ammonia analogously to example 19/3. Yield: 59%. M.p. 90° C. (dec.). MS: 444.2 (M+H$^+$).

Example 32

[4-({[1-(3-Amidino-benzyl)-5fluoro-1H -indole-2-carbonyl]-amino}-methyl)-phenyl]-trimethyl-ammonium acetate acetic acid salt

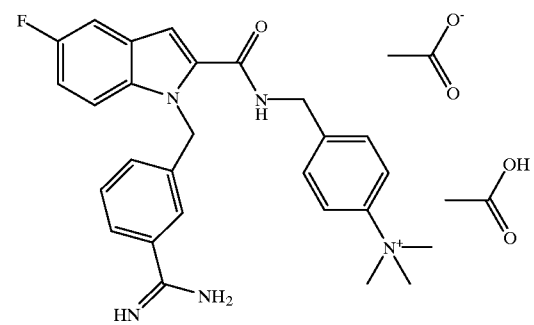

1.) [4-({[1-(3-Cyano-benzyl)-5-fluoro-1H-indole-2-carbonyl]-amino}-methyl)-phenyl]-trimethyl-ammonium iodide Starting from 5-fluoro-1-(3-cyano-benzyl)-1H-indole-2-carboxylic acid (4-dimethylamino)-benzyl amide (example 30/3) the compound was prepared by alkylation with methyl iodide analogously to example 20/1. Yield: 90%. M.p. 203–205° C. MS: 441.2 (M$^+$).

2.) [4-({[1-(3-Amidino-benzyl)-5-fluoro-1H-indole-2-carbonyl]-amino}-methyl)-phenyl]-trimethyl-ammonium acetate acetic acid salt This compound was prepared from [4-({[1-(3-cyano-benzyl)-5-fluoro-1H-indole-2-carbonyl]-amino}-methyl)-phenyl]-trimethyl-ammonium iodide, hydrogen chloride, and liquid ammonia analogously to example 19/3. Instead of trifluoroacetic acid acetic acid was used for chromatography. Yield: 74%. M.p. 172° C. (dec.). MS: 458.2 (M⁺).

Example 33

[4-({[1-(3-Amidino-benzyl)-5-fluoro-1H-indole-2-carbonyl]-amino}-methyl)-phenyl]-trimethyl-ammonium trifluoroacetate trifluoroacetic acid salt

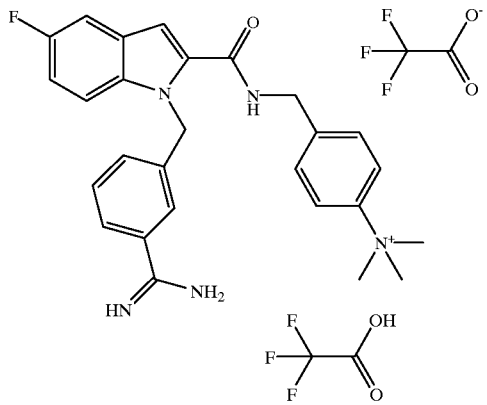

[4-({[1-(3-Amidino-benzyl)-5-fluoro-1H-indole-2-carbonyl]-amino}-methyl)-phenyl]-trimethyl-ammonium acetate acetic acid salt (32/2) was dissolved in water/ethanol/trifluoroacetic acid 1:1:0.1. The product was separated by flash chromatography on RP$_{18}$ material with water/ethanol/trifluoroacetic acid 1:1:0.1 to give the trifluoroacetic acid salt in 100% yield. M.p.120–124° C. MS: 458.2 (M⁺).

Example 34

1-(3-(Amidino-benzyl)-4-methyl-1H-indole-2-carboxylic acid (4-dimethylamino)-benzyl amide trifluoroacetic acid salt

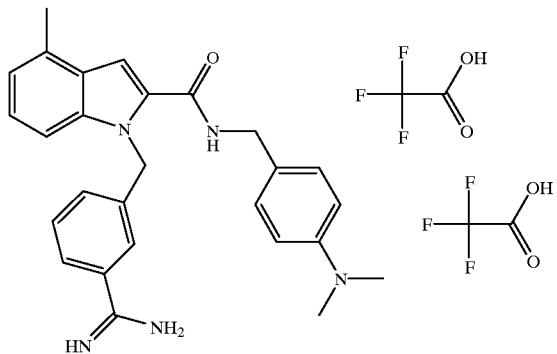

The starting material 1-(3-cyano-benzyl)-4-methyl-1H-indole-2-carboxylic acid (4-dimethylamino)-benzylamide (example 29/3) was treated analogously to example 19/3. Yield: 46%. M.p. 106° C. (dec.). MS: 440.3 (M+H⁺).

Example 35

[4-({[1-(3-Amidino-benzyl)-4-methyl-1H-indole-2-carbonyl]-amino}-methyl)-phenyl]-trimethyl-ammonium trifluoroacetate trifluoroacetic acid salt

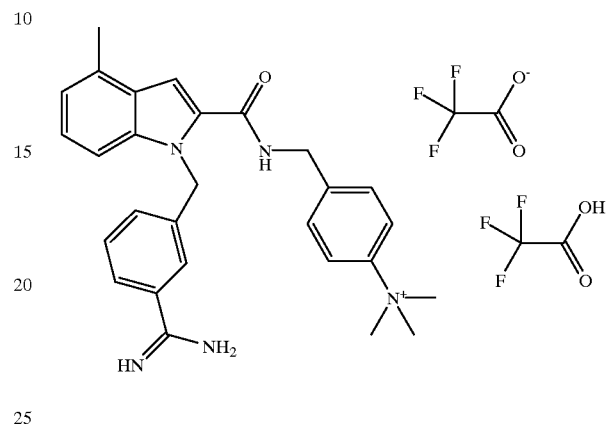

The starting material was 1-(3-cyano-benzyl)-4-methyl-1H-indole-2-carboxylic acid (4-dimethylamino)-benzyl amide (example 29/3). All steps were prepared . analogously to example 20/1 and 19/3. Yield (last step): 45%. M.p. 81° C. (dec.). MS: 454.3 (M⁺).

Example 36

[4-({[1-(3-Amidino-benzyl)-5-nitro-1H-indole-2-carbonyl]-amino}-methyl)-phenyl]-trimethyl-ammonium trifluoroacetate trifluoroacetic acid salt

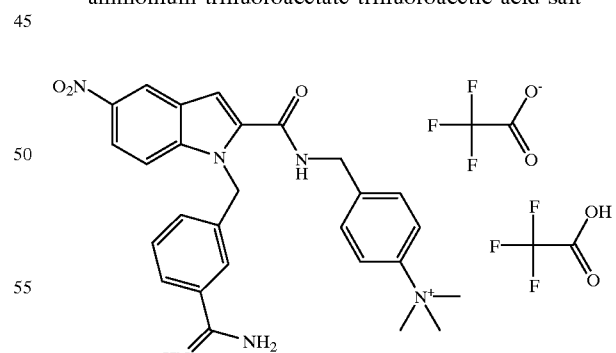

The starting material was 5-nitro-1H-indole-2-carboxylic acid ethyl ester. All steps were prepared analogously to examples 21/1, 112, 3/1, 20/1 and 19/3. Yield (last step): 52%. M.p. 120° C. (dec.). MS: 485.3 (M⁺).

Example 37

[4-({[1-(3-Amidino-benzyl)-5-amino-1H-indole-2-carbonyl]-amino}-methyl)-phenyl]-trimethyl-ammonium trifluoroacetate trifluoroacetic acid salt

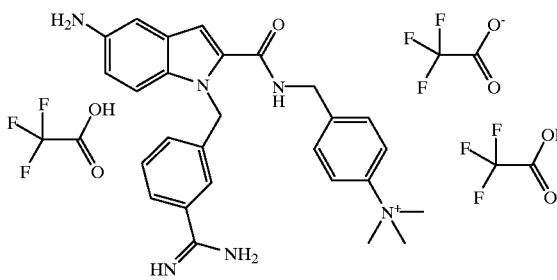

This compound was prepared from [4-({[1-(3-amidino-benzyl)-5-nitro-1H-indole-2-carbonyl]-amino}-methyl)-phenyl]-trimethyl-ammonium trifluoroacetate trifluoroacetic acid salt (example 36) by hydrogenation in ethanol with 3 equivalents of acetic acid, catalyzed by Pd/C (10%). Yield: 70%. M.p. 114° C. (dec.). MS: 455.3 (M$^+$).

Example 38

[4-({[1-(3-Amidino-benzyl)-5-methylsulfonyl-1H-indole-2-carbonyl]-amino}-methyl)-phenyl]-trimethyl-ammonium trifluoroacetate acetic acid salt

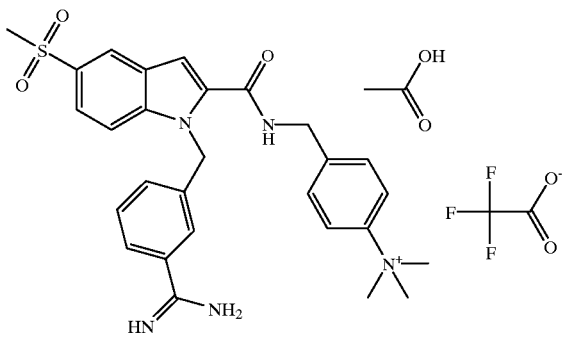

The starting material was 5-methylsulfonyl-1H-indole-2-carboxylic acid methyl ester. All steps were prepared analogously to examples 21/1, 1/2, 3/1, 20/1 and 19/3. Yield (last step): 83%. M.p. 70° C. (dec.). MS: 518.2 (M$^+$).

Example 39

[4-({[1-(3-Amidino-benzyl)-4-hydroxy-1H-indole-2-carbonyl]-amino}-methyl)-phenyl]-trimethyl-ammonium acetate acetic acid salt

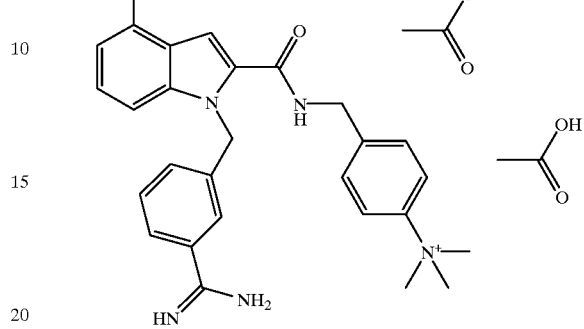

The starting material was 4-benzyloxy-1H-indole-2-carboxylic acid ethyl ester. All intermediates were prepared analogously to examples 21/1, 1/2, 3/1 and 20/1. In the last step hydrogen chloride gas was bubbled into a solution of 4-benzyloxy-1-(3-cyano-benzyl)-1-H-indole-2-carboxylic acid ethyl ester and ethanol for 4 hours at 0° C. The mixture was warmed up to room temperature overnight and evaporated. The residue was dissolved in 10 ml ethanol and liquid ammonia was added. The mixture was allowed to warm up to room temperature during stirring and concentrated. The crude material was purified by flash chromatography on RP$_{18}$ material with water/ethanol/acetic acid 7:3:0.1. Yield (last step): 57%. M.p. 113° C. (dec.). MS: 456.3 (M$^+$).

Example 40

[4-({[1-(3-Amidino-benzyl)-5-methoxy-1H-indole-2-carbonyl]-amino}-methyl)-phenyl]-trimethyl-ammonium acetate acetic acid salt

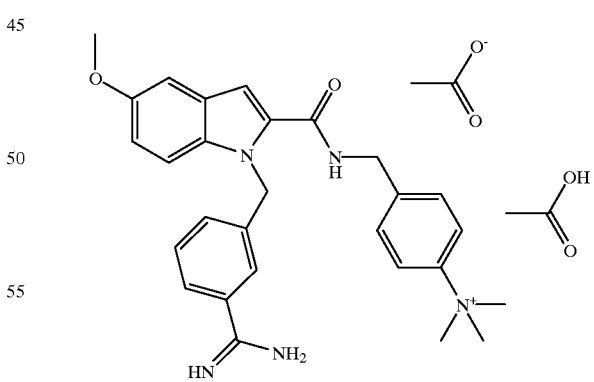

The starting material was 5-methoxy-1H-indole-2-carboxylic acid ethyl ester. All steps were prepared analogously to examples 21/1, 1/2, 3/1, 20/1 and 19/3. Yield (last step): 74%. M.p. 94° C. (dec.). MS: 470 (M$^+$).

Example 41

4-(2-{[1-(3-Amidino-benzyl)-4-methoxy-1H-indole-2-carbonyl]-amino}-ethyl)-1-methyl-pyridinium trifluoroacetate trifluoroacetic acid salt

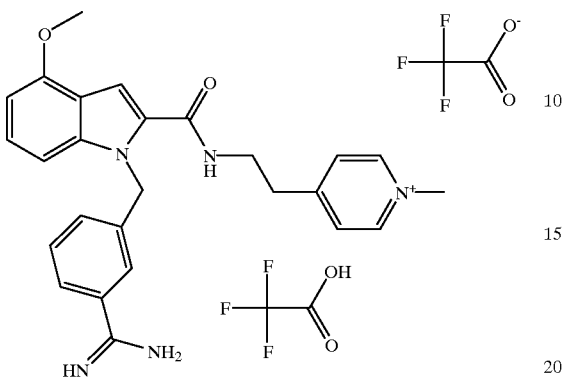

The starting material was 1-(3-cyano-benzyl)-4-methoxy-1H-indole-2-carboxylic acid (example 17/2). All steps were prepared analogously to examples 3/1, 20/1 and 19/3, but the amine in step 3/1 was 4-(2-aminoethyl)-pyridine instead of 4-(dimethylamino)-benzylamine dihydrochloride and to the solvent in step 20/1 dimethylsulfoxide was added. Yield (last step): 83%. M.p. 164° C. (dec.). MS: 442.3 (M+).

Example 42

1-(3-Amidino-benzyl)-4-methyl-1H-indole-2-carboxylic acid ethylester acetic acid salt

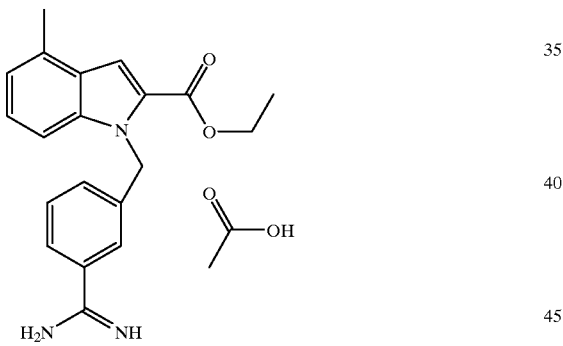

1.) 4-Methyl-1H-indole-2-carboxylic acid 3-cyano-benzyl ester

The starting material was 4-methyl-1H-indole-2-carboxylic acid. Alkylation with 3-cyano-benzylbromide (analogously to example 19/1, but the solvent was dimethylformamide instead of tetrahydrofuran) gave 4-methyl-1H-indole-2-carboxylic acid 3-cyano-benzyl ester. Yield: 75%. MS: 291.1 (M+H+).

2.) 1-(3-Cyano-benzyl)-4-methyl-1H-indole-2-carboxylic acid 3-cyano-benzyl ester The alkylation of 4-methyl-1H-indole-2-carboxylic acid 3-cyano-benzyl ester with 3-cyano-benzyl bromide was done analogously to example 21/1. Yield: 90%. MS: 406.1 (M+H+).

3.) 1-(3-Amidino-benzyl)-4-methyl-1H-indole-2-carboxylic acid ethyl ester acetic acid salt This compound was prepared from 1-(3-cyano-benzyl)-4-methyl-1H-indole-2-carboxylic acid 3-cyano-benzyl ester by using hydrogen chloride and liquid ammonia as described in example 19/3. The crude material was purified by flash chromatography on RP$_{18}$ material with water/ethanol/acetic acid 4:1:0.2 to give a fraction containing in a yield of 7% the compound described in example 63 and a fraction containing in a yield of 16% the title compound of this example. M.p. 187° C. (dec.). MS: 336.2 (M+H+).

Example 43

1-(4-Amidino-benzyl)-1H-indole-2-carboxylic acid benzyl amide hydrochloride

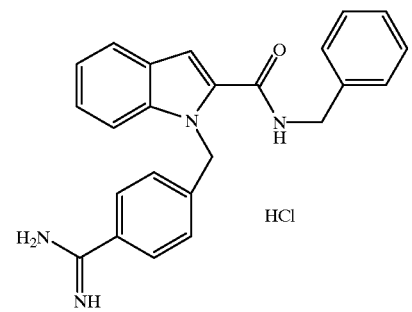

A solution of 10 g (53 mmol) 1H-indole-2-carboxylic acid ethyl ester in 80 ml of dimethylformamide was treated with 10.95 g (79 mmol) of potassium carbonate. The mixture was stirred at room temperature for 10 minutes. 3-Cyano-benzyl bromide, 15.47 g (79 mmol), was added and the mixture was heated to 100° C. After 4 hours at that temperature, it was cooled to room temperature, acidified with acetic acid (pH 5–6) and poured on ice-water. The product was extracted with methylene chloride. The organic layer was dried and evaporated. The residue was crystallized from 2-propanol to give 9.8 g of the desired product. Yield 61%. M.p. 214° C. MS: 305.1 (M+H+)

The following steps were prepared analogously to examples 1/2, 3/1 and 19/3, but the amine in step 3/1 was benzylamine instead of 4-(dimethylamino)-benzylamine dihydrochloride. Yield (last step): 35%. M.p. 266–268° C. (dec.). MS: 383.2 (M+H+).

Example 44

(RS)-1-(4-Amidino-benzyl)-1H-indole-2-carboxylic acid α-(4-pyridyl)-benzyl amide trifluoroacetic acid salt

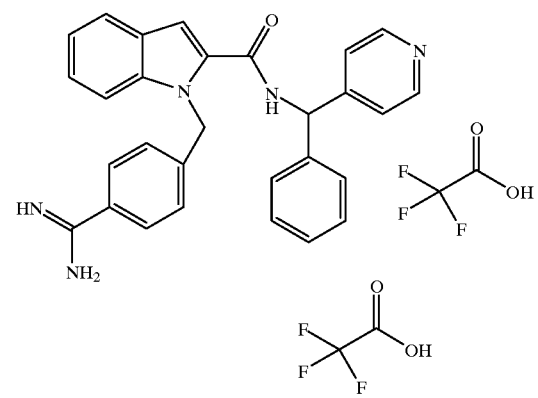

This compound was prepared from 1H-indole-2-carboxylic acid ethyl ester analogously to example 43. All steps were prepared analogously to examples 1/2, 3/1 and 19/3, but the amine in step 3/1 was (RS)-α-(4-pyridyl)-benzylamine dihydrochloride instead of 4-(dimethylamino)- benzylamine dihydrochloride. Yield (last step): 70%. M.p. 150° C. MS: 460.3 (M+H⁺).

Example 45

1-(3-Amidino-benzyl)-1H-indole-2-carboxylic acid amide trifluoroacetic acid salt

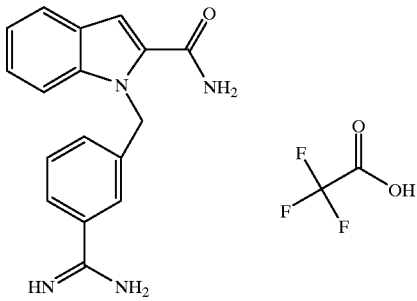

This compound was isolated in example 26/2 as a by product in 3% yield. M.p. 278° C. (dec.). MS: 293.1 (M+H⁺).

Example 46

1-(4-Amidino-benzyl)-1H-indole-2-carboxylic acid 4-chloro-benzyl amide trifluoroacetic acid salt

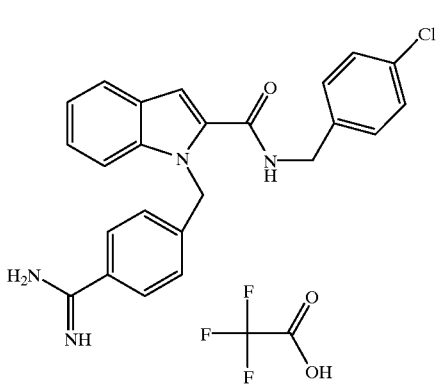

The starting material 1H-indole-2-carboxylic acid ethyl ester was alkylated with 4-cyano-benzyl bromide analogously to example 43. The following steps were prepared analogously to examples 1/2, 3/1 and 19/3, but the amine in step 3/1 was 4-chloro-benzylamine instead of 4-(dimethylamino)-benzylamine dihydrochloride. Yield (last step): 20%. M.p. 268° C. (dec.). MS: 417.2 (M+H⁺).

Example 47

1-(3-Amidino-benzyl)-4-methyl-1H-indole-2-carboxylic acid 3-amidino-benzyl amide trifluoroacetic acid salt

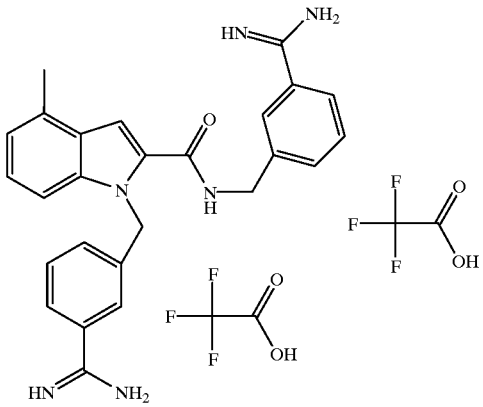

This compound was prepared from 1-(3-cyano benzyl)-4-methyl-1H-indole-2-carboxylic acid (example 29/2) analogously to examples 3/1 and 19/3, but the amine in step 3/1 was 3-cyano-benzylamine hydrobromide instead of 4-(dimethylamino)-benzylamine dihydrochloride. Yield (last step): 25%. M.p. 242–243° C. MS: 439.3 (M+H⁺).

Example 48

{4-[({1-[3-(4,5-Dihydro-1H-imidazol-2-yl)-benzyl]-5-fluoro-1H-indole-2-carbonyl}-amino)-methyl]-phenyl}-trimethyl-ammonium acetate acetic acid salt

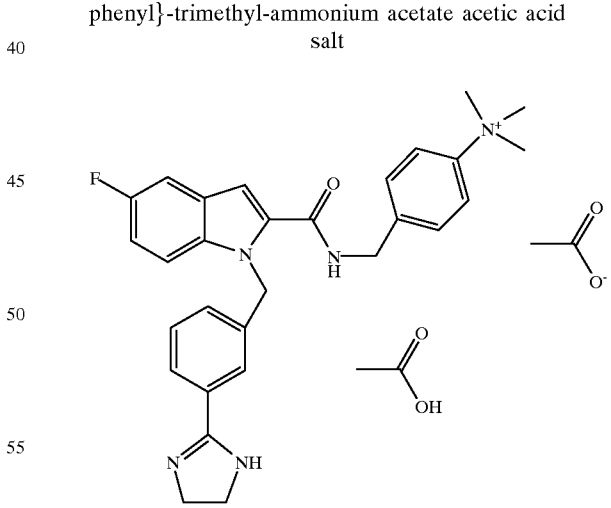

The starting material [4-({[-1-(3-cyano-benzyl)-5-fluoro-1H-indole-2-carbonyl]-amino}-methyl)-phenyl]-trimethyl-ammonium iodide (example 32/1) was reacted with hydrogen chloride and ethylendiamine (instead of liquid ammonia) analogously to example 19/3 to give the imidazoline derivative. Yield: 30%. M.p. 51° C. (dec.). MS: 484.3 (M⁺).

Example 49

1-(3-Hydroxyamidino-benzyl)-4-methoxy-1H-indole-2-carboxylic acid 2-(4-pyridyl)-ethyl amide

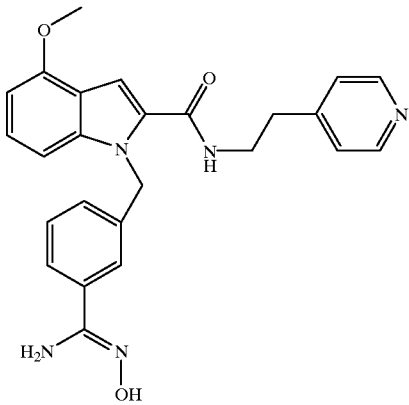

The starting material 1-(3-cyano-benzyl)-4-methoxy-1H-indole-2-carboxylic acid 2-(4-pyridyl)-ethyl amide (example 41) was dissolved in ethanol, 2.4 equivalents of hydroxylamine hydrochloride and 2.4 equivalents of triethylamine were added and the mixture was refluxed for 6.5 h. The precipitate was filtered off to give 54% of the desired product. M.p. 220–222° C. MS: 444.3 (M+H$^+$).

Example 50

1-(3-Hydroxyamidino-benzyl)-4-methoxy-1H-indole-2-carboxylic acid-2-(4-pyridyl)-ethyl amide bishydrochloride

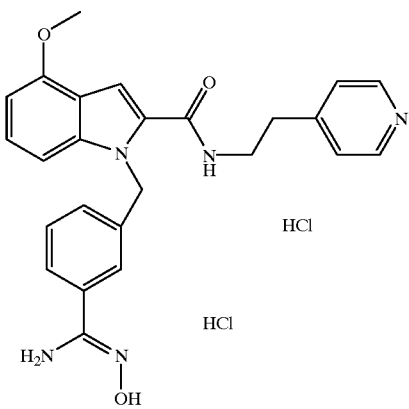

The starting material, 1-(3-hydroxyamidino-benzyl)-4-methoxy-1H-indole-2-carboxylic acid 2-(4-pyridyl)-ethyl amide (example 49), was dissolved in 0.1 N hydrochloric acid, concentrated in vacuo, dissolved in water again and lyophilized. Yield: 66%. M.p. 215–217° C. MS: 444.3 (M+H$^+$).

Example 51

1-(3-Hydroxyamidino-benzyl)-4-methoxy-1H-indole-2-carboxylic acid 2-(4-hydroxy-phenyl)-ethyl amide

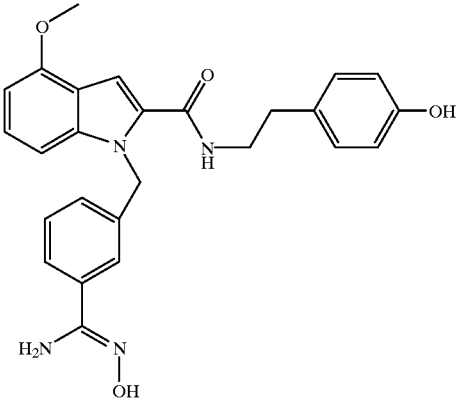

The starting material 1-(3-cyano-benzyl)-4-methoxy-1H-indole-2-carboxylic acid 2-(4-hydroxyphenyl)ethyl amide (example 25/1) was dissolved in ethanol and hydroxylamine hydrochloride and triethylamine were added. After reflux for 5 h the reaction mixture was concentrated in vacuo and partitioned between dichloromethane and water. The organic layer was separated, dried over magnesium sulfate, and concentrated in vacuo. The residue was purified by flash chromatography on silica gel with dichloromethane/methanol 19:1 to give 63% of the desired product, which solidified under water. M.p. 173–175° C. (dec.). MS: 459.3 (M+H$^+$).

Example 52

1-(3-Hydroxyamidino-benzyl)-5-chloro-1H-indole-2-carboxylic acid (4-dimethylamino)-benzyl amide

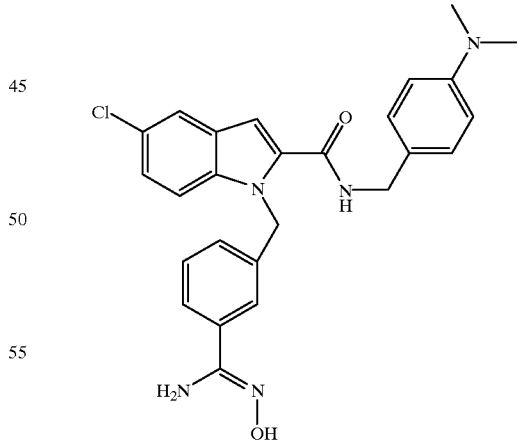

The starting material, 5-chloro-1H-indole-2-carboxylic acid ethyl ester, was treated analogously to example 21/1. All intermediates were prepared analogously to example 1/2 and 3/1. The title compound was prepared analogously to example 49. Purification by flash chromatography on silica gel with dichloromethane/methanol 19:0.6 gave a mixture of two compounds, the title compound and an unknown compound which were separated by HPLC. Yield (last step): 6%. M.p. 200° C. (dec.). MS:476.1 (M+H⁺).

Example 53

1-(3-Hydroxyamidino-benzyl)-1H-indole-2-carboxylic acid (3-hydroxyamidino-benzyl)ester

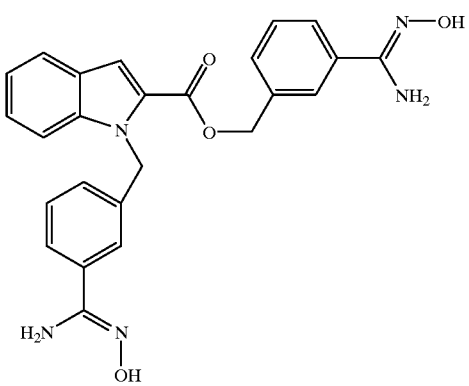

1-(3-Cyano-benzyl)-1H-indole-2-carboxylic acid 3-cyano-benzyl ester (example 26/1) was dissolved in ethanol, 3 equivalents of hydroxylamine were added, and the mixture was refluxed for 3 h. The solvent was removed in vacuo and the residue was partitioned between ethyl acetate and water. The organic layer was dried over sodium sulfate and concentrated in vacuo. The compound was purified by flash chromatography on silica gel with dichloromethane/methanol 20:1 to give 76% of the desired product. M.p. 114–116° C. MS: 458.2 (M+H⁺).

Example 54

(RS)-1-(3-Amidino-benzyl)-4-methoxy-1H-indole-2-carboxylic acid α-(4-pyridyl-benzyl)amide trifluoroacetic acid salt

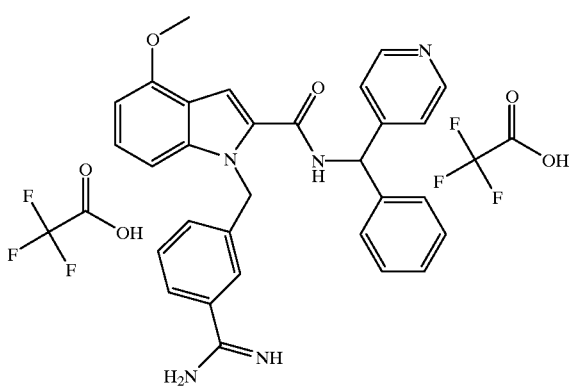

This compound was a by-product of the reactions described in example 24. Purification by flash chromatography on silica gel with dichloromethane/methanol/trifluoroacetic acid 9:1:0.2 gave 3% of the title compound. M.p. 105° C. MS: 490.2 (M+H⁺).

Example 55

[4-({[1-(3-Amidino-benzyl)-5-chloro-1H-indole-2-carbonyl]-amino}-methyl)-phenyl]-trimethyl-ammonium trifluoroacetate trifluoroacetic acid salt

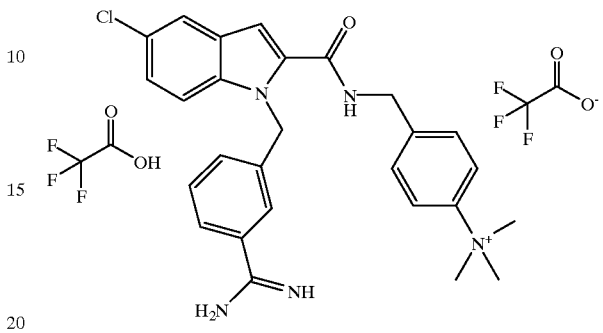

The starting material, 5-chloro-1-(3-cyano-benzyl)-1H-indole-2-carboxylic acid (4-dimethylamino)-benzyl amide (example 52) was reacted analogously to example 1/4 and 1/5. Yield (last 2 steps): 8%. M.p. 112° C. (dec.). MS: 474.2 (M⁺).

Example 56

[4-({[5-Benzyloxy-1-(3-amidino-benzyl)-1H-indole-2-carbonyl]-amino}-methyl)-phenyl]-trimethyl-ammonium trifluoroacetate trifluoroacetic acid salt

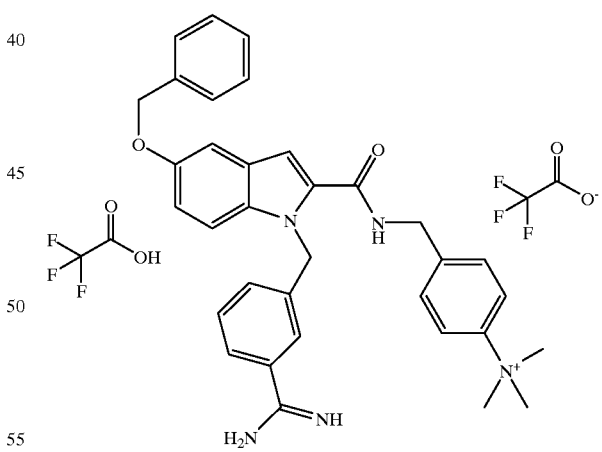

This compound was prepared from 5-benzyloxy-1-(3-cyano-benzyl)-1H-indole-2-carboxylic acid (example 21/2), 4-(dimethylamino)-benzylamine dihydrochloride, diphenylphosphoryl azide, and diisopropylethylamine analogously to example 3/1, hydrogen sulfide analogously to example 1/4, and methyl iodide in acetone analogously to example 115. Yield (last step): 52%. M.p. 60° C. (dec.). MS: 546.3 (M⁺).

Example 57

[4-({[1-(3-Amidino-benzyl)-5-hydroxy-1H-indole-2-carbonyl]-amino}-methyl)-phenyl]-trimethyl-ammonium trifluoroacetate trifluoroacetic acid salt

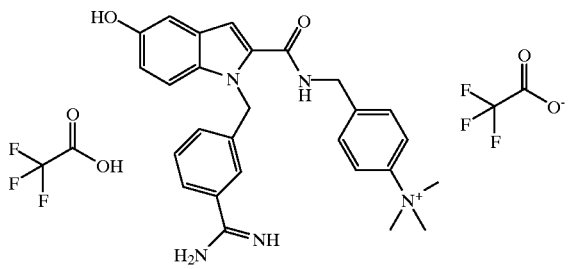

The starting material, [4-({[5-benzyloxy-1-(3-amidino-benzyl)-1H-indole-2-carbonyl]-amino}-methyl)-phenyl]-trimethyl-ammonium trifluoroacetate trifluoroacetic acid salt (example 56), was dissolved in ethanol, 2 equivalents of trifluoroacetic acid and Pd/C (10%) were added and the mixture was hydrogenated. The reaction mixture was concentrated and purified by flash-chromatography on silica gel with dichloromethane/methanol/trifluoroacetic acid 9:1:0.1. The product was concentrated and lyophilized to give 53% of the desired product. M.p. 78° C. (dec.). MS: 456.4 (M+).

Example 58

[4-({[1-(3-Amidino-benzyl)-5-tert-butoxycarbonylamino-1H-indole-2-carbonyl]-amino}-methyl)-phenyl]-trimethyl-ammonium acetate acetic acid salt

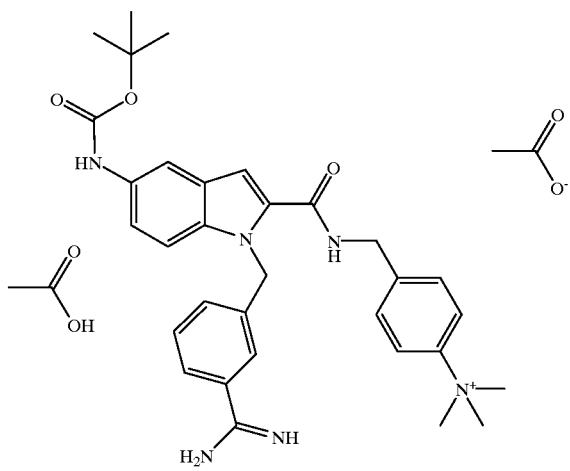

1.) 5-(tert-Butoxycarbonylamino)-1-(3-thiocarbamoyl)-benzyl)-1H-indole-2-carboxylic acid 4-(dimethylamino)-benzyl amide The starting material, 1-(3-cyano-benzyl)-5-nitro-1H-indole-2-carboxylic acid (4-dimethylamino)-benzyl amide (example 36), was treated with hydrogen sulfide gas analogously to example 1/4. The resulting compound was dissolved in ethanol, 2 equivalents of di-tert-butyl-dicarbonate, and 3 equivalents of sodium bicarbonate were added and the mixture was stirred at room temperature for 10 h. The reaction mixture was concentrated and then partitioned between dichloromethane and citric acid (0.1% in water). The organic layer was dried over magnesium sulfate concentrated, and purified by flash chromatography on silica gel with dichloromethane/methanol 20:0.2 to give 43% of the desired product. MS: 558.4 (M+H+).

2.) [4-({[1-(3-Amidino-benzyl)-5-tert-butoxycarbonylamino-1H-indole-2-carbonyl]-amino}-methyl)-phenyl]-trinethyl-ammonium acetate acetic acid salt This compound was prepared analogously to example 1/5 but the solvent for the methylation was pure acetone. The crude product was purified by flash chromatography on RP$_{18}$-material with ethanol/water/trifluoroacetic acid 1:1:0.1 to give 55% of the desired product. M.p. 146° C. (dec.). MS: 555 (M+).

Example 59

1-(3-Amidino-benzyl)-5-benzyloxy-1H-indole-2-carboxylic acid 3-amidino-benzylamide dihydroiodide

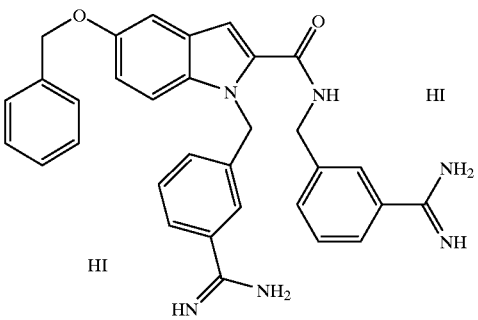

1.) 5-Benzyloxy-1-(3-cyano-benzyl)-1H-indole-2-carboxylic acid 3-cyano-benzylamide This compound was prepared from 5-benzyloxy-1-(3-cyano-benzyl)-1H-indole-2-carboxylic acid (500 mg, 1.3 mmol, example 21/2), diphenylphosphoryl azide (370 µl, 1.7 mmol), N,N-diisopropylethylamine (440 µl, 2.6 mmol), and 3-cyano-benzylamine hydrobromide (312 mg, 1.5 mmol) in N,N-dimethylformamide (10 ml) as described in example 3/1. The purification by flash chromatography on silica gel was done with dichloromethane to give 451 mg (69%) of the desired product.

2.) 5-Benzyloxy-1-(3-thiocarbamoyl-benzyl)-1H-indole-2-carboxylic acid 3-thiocarbamoyl-benzylamide This compound was prepared from 5-benzyloxy-1-(3-cyano-benzyl)-1H-indole-2-carboxylic acid 3-cyano-benzylamide (451 mg, 0.9 mmol), pyridine (6.67 ml, 83 mmol), triethylamine (5.41 ml, 39 mmol), and hydrogen sulfide as described in example 1/4. The purification by flash chromatography on silica gel was done with dichloromethane/methanol 19:0.15 to give 138 mg (27%) of the desired product.

3.) 1-(3-Amidino-benzyl)-5-benzyloxy-1H-indole-2-carboxylic acid 3-amidino-benzylamide dihydroiodide 5-Benzyloxy-1-(3-thiocarbamoyl-benzyl)-1H-indole-2-carboxylic acid 3-thiocarbamoyl-benzylamide (138 mg, 0.24 mmol) was dissolved in 5 ml of acetone in a vial, the vial was sealed and methyl iodide (0.4 ml, 26 equivalents) was added via a syringe. The reaction mixture was stirred at room temperature. 4 days later the yellow precipitate was collected by filtration and washed with diethylether. The precipitate (188 mg, 0.22 mmol), acetic acid (0.15 ml, 12 equivalents), ammonium acetate (307 mg, 18 equivalents), and methanol (6 ml) were treated as described in example 1/5. The crude material was purified by flash chromatography on RP$_{18}$ material with ethanol/water/trifluoroacetic acid 1:1:0.1 to give 157 mg of the desired compound (90%) after lyophilization. M.p. 138° C. (dec.). MS: 531.3 (M+H+).

Example 60

[4-({[1-(3-Amidino-benzyl)-5-fluoro-1H-indole-2-carbonyl]-amino}-methyl)-phenyl]-benzylimethyl-ammonium chloride hydrochloride

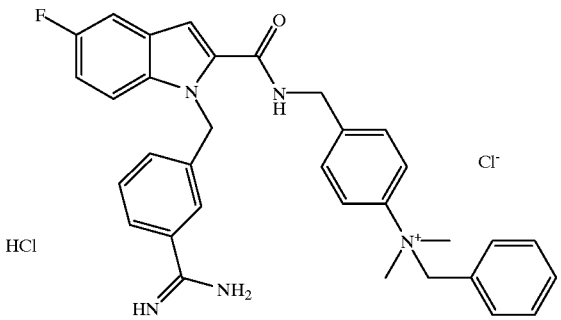

1.) Benzyl-[4-({[1-(3-cyano-benzyl)-5-fluoro-1H-indole-2-carbonyl]-amino}-methyl)-phenyl]-dimethyl-ammonium bromide This compound was prepared from 1-(3-cyano-benzyl)-5-fluoro-1H-indole-2-carboxylic acid (4-dimethylamino)-benzyl amide (840 mg, 1.97 mmol, example 30/3), benzyl bromide (237 µl, 1 equivalent), and acetone (8 ml) analogously to example 20/1, but the reaction temperature was kept at 50° C. The precipitate was filtered off to give 1.02 g of the desired product (87%).

2.) [4-({[1-(3-Amidino-benzyl)-5-fluoro-1H-indole-2-carbonyl]-amino}-methyl)-phenyl]-benzyl-dimethyl-ammonium chloride hydrochloride This compound was prepared from benzyl-[4-({[1-(3-cyano-benzyl)-5-fluoro-1H-indole-2-carbonyl]-amino}-methyl)-phenyl]-dimethyl-ammonium bromide (200 mg, 0.335 mmol), ethanol, hydrogen chloride, and liquid ammonia analogously to example 1913. Purification by reversed phase chromatography on $RP_{18}$ material (water/ethanol/acetic acid 7:3:0.1) followed by lyophilization gave 156 mg of the desired product (77%). M.p. 136° C. MS: 534.4 (4%, $M^+$).

Example 61

Allyl-[4-({[1-(3-amidino-benzyl)-5-fluoro-1H-indole-2-carbonyl]-amino}-methyl)-phenyl]-dimethyl-ammonium chloride acetic acid salt

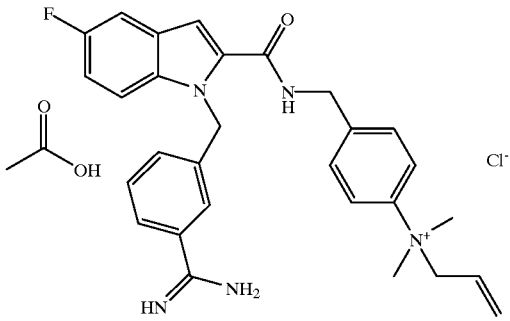

1.) Allyl-[4-({[1-(3-cyano-benzyl)-5-fluoro-1H-indole-2-carbonyl]-amino}-methyl)-phenyl]-dimethyl-ammonium bromide This compound was prepared from 1-(3-cyano-benzyl)-5-fluoro-1H-indole-2-carboxylic acid (4-dimethylamino)-benzyl amide (200 mg, 0.47 mmol, example 30/3), allyl bromide (81 µl, 2 equivalents), and acetone (3.5 ml). The reaction partners were mixed, the flask was closed and heated to 55° C. After 6 h the heating was stopped. Four weeks later another 1.06 ml allyl bromide were added, the flask was closed, and it was heated to 55° C. again. After 3 weeks a white precipitate was filtered off, washed with diethylether, and dried in vacuo to give 222 mg of the desired product (86%). M.p. 163–165° C.

2.) Allyl-[4-({[1-(3-amidino-benzyl)-5-fluoro-1H-indole-2-carbonyl]-amino}-methyl)-phenyl]-dimethyl-ammonium chloride acetic acid salt This compound was prepared from allyl-[4-({[1-(3-cyano-benzyl)-5-fluoro-1H-indole-2-carbonyl]-amino}-methyl)-phenyl]-dimethyl-ammonium bromide (222 mg, 0.406 mmol), ethanol (12 ml), hydrogen chloride, and liquid ammonia analogously to example 19/3. The crude product was purified by chromatography on silica gel with dichloromethane/methanol/acetic acid 3:2:0.05 to 1:4:0.05. Lyophilization gave 131 mg of the desired product (56%). M.p. 133° C. (dec.). MS: 484.3 ($M^+$).

Example 62

[4-({[1-(3-Amidino-benzyl)-5-fluoro-1H-indole-2-carbonyl]-amino}-methyl)-phenyl]-dimethyl-2-propynyl-ammonium acetate acetic acid salt

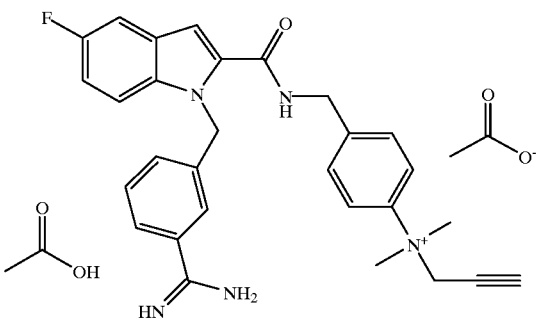

1.) [4-({[1-(3-Cyano-benzyl)-5-fluoro-1H-indole-2-carbonyl]-amino}-methyl)-phenyl]-dimethyl-2-propynyl-ammonium bromide compound was prepared from 1-(3-cyano-benzyl)-5-fluoro-1H-indole-2-carboxylic acid (4-dimethylamino)-benzyl amide (200 mg, 0.47 mmol, example 30/3), propargylbromide (140 mg, 2 equivalents, 80% in toluene), and acetone (5 ml). The reaction partners were mixed, the flask was closed and heated to 50° C. After 5 h the heating was stopped. After two days the mixture was concentrated in vacuo and the desired product was precipitated with diethylether to yield 220 mg of a white solid (86%).

2.) [4-({[1-(3-Amidino-benzyl)-5-fluoro-1H-indole-2-carbonyl]-amino}-methyl)-phenyl]-dimethyl-2-propynyl-ammonium acetate acetic acid salt This compound was prepared from [4-({[1-(3-cyano-benzyl)-5-fluoro-1H-indole-2-carbonyl]-amino}-methyl)-phenyl]-dimethyl-2-propynyl-ammonium bromide (220 mg, 0.406 mmol), ethanol (12 ml), hydrogen chloride, and liquid ammonia analogously to example 19/3. The crude product was purified by chromatography on silica gel with dichloromethane/methanol/acetic acid 3:2:0.05 to 1:4:0.05. Lyophilization gave 131 mg of the desired product (56%). M.p. 109° C. (dec.). MS: 482.3 ($M^+$).

Example 63

1-(3-Amidino-benzyl)-4-methyl-1H-indole-2-carboxylic acid 3-amidino-benzylester acetic acid salt

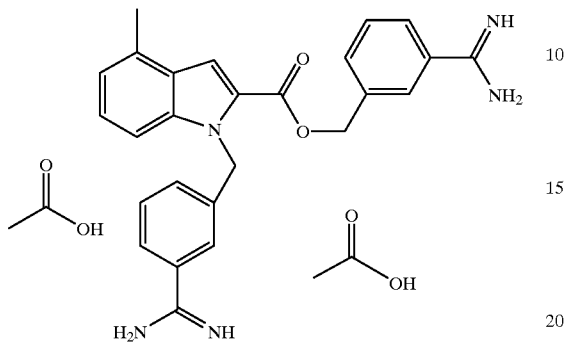

The fraction obtained in the chromatography of example 42/3 consisted of three compounds which were separated by preparative HPLC to give 2.5 mg of the title compound after lyophilization. Yield: 7%. M.p. 53° C. (dec.). MS: 440.3 (M+H$^+$).

Example 64

[4-({[1-(3-Amidino-benzyl)-4-methyl-1H-indole-2-carbonyl]-amino}-methyl)-phenyl]-trimethyl-ammonium acetate acetic acid salt

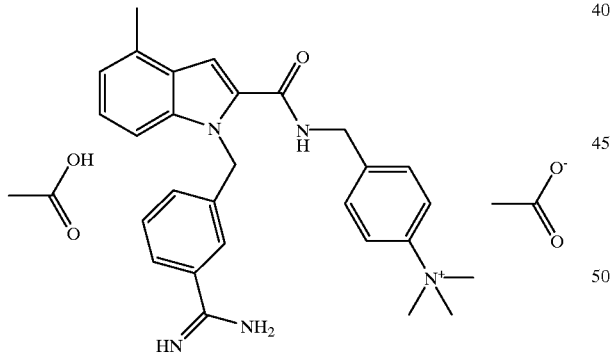

10 g of ion exchange resin AG 1-X8 (Bio-Rad) were filled into a column, rinsed first with water, then with 1 N sodium acetate solution, and again with water. [4-({[1-(3-Amidino-benzyl)-4-methyl-1H-indole-2-carbonyl]-amino}-methyl)-phenyl]-trimethyl-ammonium trifluoroacetate trifluoroacetic acid salt (example 35) was dissolved in water and passed through the ion exchange column. After rinsing with 150 ml water, the solution was concentrated in vacuo to 25 ml, which were lyophilized to give 79 mg of the desired product (100%). M.p. 89° C. (dec.). MS: 454.3 (M$^+$).

Example 65

1-(3-Amidino-benzyl)-4-methoxy-1H-indole-2-carboxylic acid 4-hydroxy-benzyl amide hydrochloride

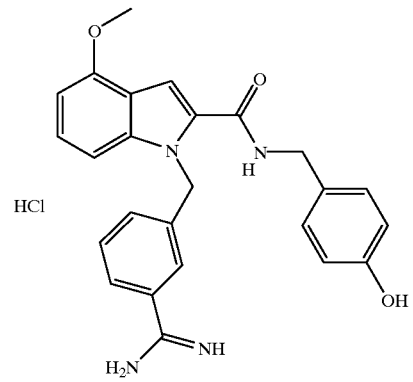

1.) 1-(3-Cyano-benzyl)-4-methoxy-1H-indole-2-carboxylic acid 4-hydroxy-benzyl amide The title compound was prepared using 1-(3-cyano-benzyl)-4-methoxy-1H-indole-2-carboxylic acid (400 mg, 1.31 mmol; example 24/12), diphenylphosphoryl azide (365 µl, 1.3 equivalents), N,N-diisopropylethylamine (850 µl, 3.75 equivalents), and 4-aminomethyl-phenol (560 mg, 2.1 equivalents) in N,N-dimethylformamide (10 ml) as described in example 3/1.

2.) 1-(3-Amidino-benzyl)-4-methoxy-1H-indole-2-carboxylic acid 4-hydroxy-benzyl amide hydrochloride This compound was prepared from 1-(3-cyano-benzyl)-4-methoxy-1H-indole-2-carboxylic acid 4-hydroxy-benzyl amide (200 mg, 0.49 mmol), hydrogen chloride, and liquid ammonia analogously to example 19/3. Purification by reversed phase chromatography on RP$_{18}$ material with water/ethanol/acetic acid 7:3:0.1 and lyophilization gave 179 mg of the desired product (79%). M.p. 202° C. (dec.). MS: 429.2 (100%; M+H$^+$).

Example 66

1-(3-Amidino-benzyl)-4-methoxy-1H-indole-2-carboxylic acid 4-amidino-benzyl amide acetic acid salt

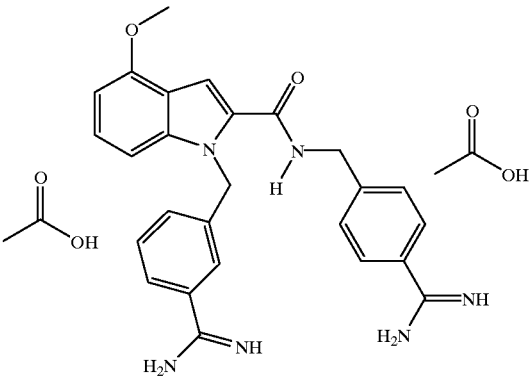

1.) 1-(3-Cyano-benzyl)-4-methoxy-1H-indole-2-carboxylic acid 4-cyano-benzyl amide The title compound was prepared using 1-(3-cyano-benzyl)-4-methoxy-1H-indole-2-carboxylic acid (400 mg, 1.31 mmol; example 24/2), diphenylphosphoryl azide (365 µl, 1.3 equivalents), N,N-diisopropylethylamine (850 µl, 3.75 equivalents), and 4-aminomethyl-benzonitrile (585 mg, 2.1 equivalents) in N,N-dimethylformamide (10 ml) as described in example 3/1.

2.) 1-(3-Amidino-benzyl)-4-methoxy-1H-indole-2-carboxylic acid 4-amidino-benzyl amide acetic acid salt This compound was prepared from 1-(3-cyano-benzyl)-4-methoxy-1H-indole-2-carboxylic acid 4-cyano-benzyl amide (200 mg, 0.48 mmol), hydrogen chloride, and liquid ammonia analogously to example 19/3. Purification by reversed phase chromatography on RP$_{18}$ material with water/ethanol/acetic acid 1:1:0.1 followed by lyophilization gave 68 mg of the desired product (25%). M.p. 1 86° C. (dec.). MS: 228.1 ((M+2H$^+$)/2).

Example 67

1-(3-Amidino-benzyl)-5-benzyloxy-1H-indole-2-carboxylic acid 3-amidino-benzyl ester acetic acid salt

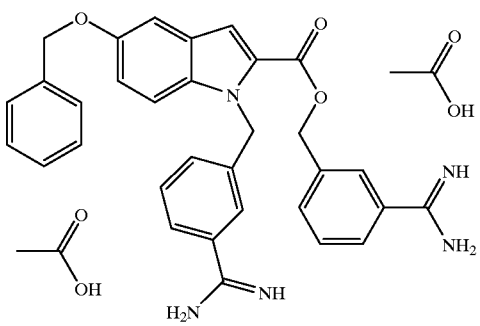

1.) 5-Benzyloxy-1-(3-cyano-benzyl)-1H-indole-2-carboxylic acid 3-cyano-benzyl ester 5-Benzyloxy-1-(3-cyano-benzyl)-1H-indole-2-carboxylic acid (500 mg, 1.31 mmol; example 21/2) was dissolved in N,N-dimethylformamide (20 ml) and heated to 60° C. Potassium carbonate (200 mg, 1.44 mmol) was added and the solution was stirred at 60° C. 1 hour later 3-cyano-benzyl bromide (282 mg, 1.44 mmol) was added and the reaction mixture was stirred for another 5 hours at 60° C. The next day it was partitioned between water and methyl tert-butyl ether, dried over magnesium sulfate, and concentrated in vacuo. The crude material was purified by flash chromatography on silica gel with dichloromethane/heptane 4:1 to give 524 mg of the desired product (80%). M.p. 125–128° C.

2.) 5-Benzyloxy-1-(3-thiocarbamoyl-benzyl)-1H-indole-2-carboxylic acid 3-thiocarbamoyl-benzyl ester Hydrogen sulfide was introduced for 15 minutes into an ice-water cooled solution of 520 mg of the above 5-benzyloxy-1-(3-cyano-benzyl)-1H-indole-2-carboxylic acid 3-cyano-benzyl ester in 7.7 ml of pyridine and 6.2 ml of triethylamine. The mixture was stirred at room temperature for 18 hours in a sealed vial and then partitioned between toluene and 10% aqueous sodium carbonate solution. The organic layer was dried and evaporated and the residue was purified by flash chromatography on silica gel with dichloromethane/methanol 19:0.2 to give 487 mg of the desired product (82%). M.p. 177–180° C.

3.) 1-(3-Amidino-benzyl)-5-benzyloxy-1H-indole-2-carboxylic acid 3-amidino-benzyl ester acetic acid salt 5-Benzyloxy-1-(3-thiocarbamoyl-benzyl)-1H-indole-2-carboxylic acid 3-thiocarbamoyl-benzyl ester (487 mg, 0.86 mmol) was dissolved in 15 ml of acetone in a vial, the vial was sealed and methyl iodide (1.39 ml, 22 mmol) was added via a syringe. The reaction mixture was stirred at room temperature. 4 days later the yellow precipitate was collected by filtration and washed with diethylether. The precipitate (597 mg, 0.7 mmol), acetic acid (0.48 ml, 12 equivalents), ammonium acetate (957 mg, 18 equivalents), and methanol (10 ml) were treated as described in example 1/5. The crude material was purified by flash chromatography on RP$_{18}$ material with ethanol/water/trifluoroacetic acid to give 460 mg of the trifluoroacetic acid salt of the desired compound. To get the acetic acid salt of the product, it was passed over a column with 46 g ion exchange resin analogously to example 64. The resulting solution was concentrated to 100 ml and lyophilized to give 311 mg of the desired product (68%). M.p. 147° C. (dec.). MS: 532.3 (M+H$^+$).

Example 68

[4-({[1-(3-Amidino-benzyl)-4-benzyloxy-1H-indole-2-carbonyl]-amino}-methyl)-phenyl]-trimethyl-ammonium iodide hydroiodide

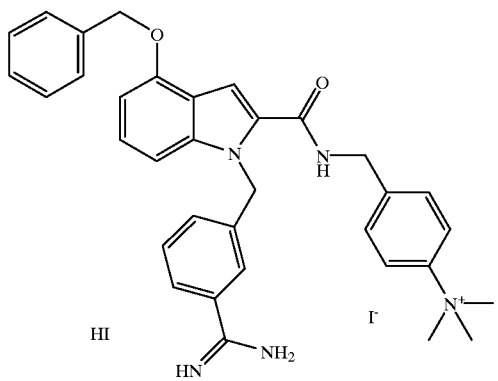

1.) 4-Benzyloxy-1-(3-cyano-benzyl)-1H-indole-2-carboxylic acid ethyl ester

This compound was prepared from 4-benzyloxy-1H-indole-2-carboxylic acid ethyl ester (3 g, 10 mmol), sodium hydride (294 mg, 12 mmol), 3-cyano-benzyl bromide (2.4 g, 12 mmol), and N,N-dimethylformamide (20 ml) analogously to example 21/1. The reaction mixture was neutralized with 2 N hydrochloric acid and partitioned between water and methyl tert-butyl ether. The organic layer was dried, concentrated in vacuo, and purified by flash chromatography with dichloromethane/heptane 7:3 to give 2.914 g (71%) of the desired product.

2.) 4-Benzyloxy-1-(3-cyano-benzyl)-1H-indole-2-carboxylic acid

This compound was prepared from 4-benzyloxy-1-(3-cyano-benzyl)-1H-indole-2-carboxylic acid ethyl ester (2.914 g, 7.1 mmol), sodium hydroxide (2.13 g, 53 mmol), methanol (175 ml), and water (8.95 ml) analogously to example 1/2. The reaction mixture was neutralized with 4 N hydrochloric acid. The white precipitate was collected by filtration, washed with water, and purified by flash chromatography on silica gel with dichloromethane/methanol 19:1 to give 2.147 g (79%) of the desired product.

3.) 4-Benzyloxy-1-(3-cyano-benzyl)-1H-indole-2-carboxylic acid 4-(dimethylamino)-benzylamide This compound was prepared from 4-benzyloxy-1-(3-cyano-benzyl)-1H-indole-2-carboxylic acid (400 mg, 1.05 mmol), diphenylphosphoryl azide (290 µl, 1.36 mmol), N,N-diisopropylethylamine (360 µl, 2.1 mmol), and 4-(dimethylamino)-benzylamine dihydrochloride (261 mg, 1.2 mmol) in N,N-dimethylformamide (10 ml) as described in example 3/1. The purification by flash chromatography on silica gel was done with dichloromethane/methanol 20:0.05 to give 347 mg (64 %) of the desired product.

4.) 4-Benzyloxy-1-(3-thiocarbamoyl-benzyl)-1H-indole-2-carboxylic acid 4-(dimethylamino)-benzylamide This compound was prepared from 4-benzyloxy-1-(3-cyano-benzyl)-1H-indole-2-carboxylic acid 4-(dimethylamino)-benzylamide (347 mg, 0.67 mmol) and hydrogen sulfide as described in example 1/4. The purification by flash chromatography on silica gel was done with dichloromethane/methanol 19:1 to give 342 mg (92%) of the desired product.

5.) [4-({[1-(3-Amidino-benzyl)-4-benzyloxy-1H-indole-2-carbonyl]-amino}-methyl)-phenyl]-trimethyl-ammonium iodide hydroiodide This compound was prepared from 4-benzyloxy-1-(3-thiocarbamoyl-benzyl)-1H-indole-2-carboxylic acid 4-(dimethylamino)-benzylamide (342 mg, 0.62 mmol), acetone (15 ml), methyl iodide (0.98 ml, 15 mmol), acetic acid (0.4 m, 0.7 mmol), ammonium acetate (809 mg, 10 mmol), and methanol (7 ml) as described in example 1/5 but the solvent for the methylation was pure acetone. The crude material was purified by flash chromatography on RP$_{18}$ material with ethanol/water/acetic acid 1:1:0.1 to give 374 mg of the desired compound (80 %). M.p. 158° C. (dec.). MS: 546.2 (M$^+$).

Example 69

1-(3-Amidino-benzyl)-5-hydroxy-1H-indole-2-carboxylic acid 3-amidino-benzylamide; trifluoroacetic acid salt

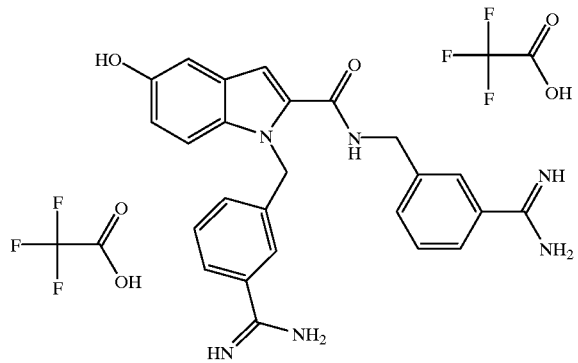

1-(3-Amidino-benzyl)-5-benzyloxy-1H-indole-2-carboxylic acid 3-amidino-benzylamide dihydroiodide (74 mg, 0.09 mmol; example 59) was dissolved in ethanol (9 ml). Hydrogen chloride gas was bubbled through the solution for 5 h. After standing for about 3 days the mixture was evaporated and purified by flash chromatography on RP$_{18}$ material with ethanol/water/trifluoroacetic acid 1:1:0.1 to give 51 mg of the desired product containing an unknown impurity. Preparative HPLC of 44 mg of this mixture gave 6.7 mg of the pure desired compound (10%). M.p. 125° C. (dec.). MS: 441.3 (M+H$^+$).

Example 70

[4-({[1-(3-Amidino-benzyl)-4-bromo-1H-indole-2-carbonyl]-amino}-methyl)-phenyl]-trimethyl-ammonium acetate acetic acid salt

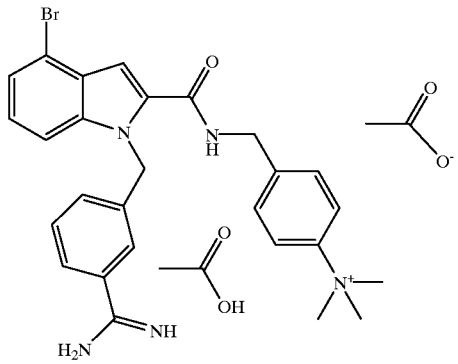

1.) 4-Bromo-1-(3-cyano-benzyl)-1H-indole-2-carboxylic acid ethyl ester

The compound was prepared from 4-bromo-1H-indole-2-carboxylic acid ethyl ester (5 g, 19 mmol), sodium hydride (537 mg, 22 mmol), 3-cyano-benzyl bromide (4.39 g, 22 mmol), and N,N-dimethylformamide (50 ml) analogously to example 21/1. The crude material was purified by crystallization from methanol to give 6.093 g (84%) of the desired product. M.p. 163–165° C. (dec.).

2.) 4-Bromo-1-(3-cyano-benzyl)-1H-indole-2-carboxylic acid

This compound was prepared from 4-bromo-1-(3-cyano-benzyl)-1H-indole-2-carboxylic acid ethyl ester (6.093 g, 16 mmol), sodium hydroxide (4.77 g, 120 mmol), methanol (800 ml), and water (20.2 ml) analogously to example 1/2. The precipitated product was washed and dried. Yield: 5.562 g (98%). M.p. 236–238° C.

3.) 4-Bromo-1-(3-cyano-benzyl)-1H-indole-2-carboxylic acid 4-dimethylamino-benzylamide This compound was prepared from 4-bromo-1-(3-cyano-benzyl)-1H-indole-2-carboxylic acid (1 g, 2.8 mmol), diphenylphosphoryl azide (790 μl, 3.66 mmol), N,N-diisopropylethylamine (960 μl, 5.6 mmol), and 4-(dimethylamino)-benzylamine dihydrochloride (703 mg, 3.1 mmol) in N,N-dimethylformamide (40 ml) as described in example 3/1. The purification by flash chromatography on silica gel was done with dichloromethane/methanol 20:0.05 to give 818 mg (60 %) of the desired product. M.p. 110–112° C.

4.) [4-({[4-Bromo-1-(3-cyano-benzyl)-1H-indole-2-carbonyl]-amino}-methyl)-phenyl]-trimethyl-ammonium iodide This compound was prepared from 4-bromo-1-(3-cyano-benzyl)-1H-indole-2-carboxylic acid 4-dimethylamino-benzylamide (818 mg, 1.68 mmol), methyl iodide (2.27 ml, 44 mmol), and acetone (8 ml) analogously to example 20/1. Yield: 927 mg (88%). M.p. 219–224° C.

5.) [4-({[1-(3-Amidino-benzyl)-4-bromo-1H-indole-2-carbonyl]-amino}-methyl)-phenyl]-trimethyl-ammonium acetate acetic acid salt This compound was prepared from [4-({[4-bromo-1-(3-cyano-benzyl)-1H-indole-2-carbonyl]-amino}-methyl)-phenyl]-trimethyl-ammonium iodide (200 mg, 0.32 mmol), ethanol (13 ml), hydrogen chloride, and liquid ammonia analogously to example 19/3. Purification by reversed phase chromatography on RP$_{18}$ material with water/ethanol/trifluoroacetic acid 1:1:0.1 gave 249 mg of the desired product as trifluoroacetic acid salt. This compound was converted into the acetic acid salt by ion exchanger chromatography analogously to example 64. Yield: 150 mg (74%). M.p. 145° C. (dec.). MS: 518.2 (M$^+$; $^{79}$Br).

Example 71

[4-({[1-(3-Amidino-benzyl)-5-bromo-1H-indole-2-carbonyl]-amino}-methyl)-phenyl]-trimethyl-ammonium acetate acetic acid salt

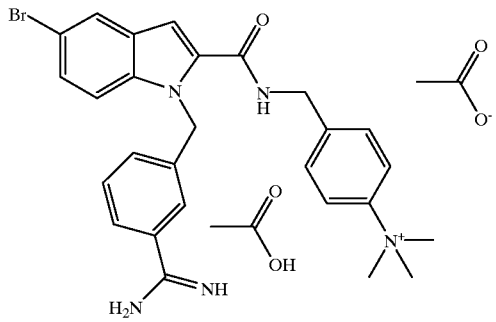

1.) 5-Bromo-1-(3-cyano-benzyl)-1H-indole-2-carboxylic acid ethyl ester

The compound was prepared from 5-bromo-1H-indole-2-carboxylic acid ethyl ester (6 g, 22 mmol), sodium hydride (645 mg, 27 mmol), 3-cyano-benzyl bromide (5.26 g, 27 mmol), and N,N-dimethylformamide (50 ml) analogously to example 21/1. The crude material was purified by crystallization from methanol to give 8.07 g (96%) of the desired product. M.p. 124–128° C. (dec.).

2.) 5-Bromo-1-(3-cyano-benzyl)-1H-indole-2-carboxylic acid

This compound was prepared from 5-bromo-1-(3-cyano-benzyl)-1H-indole-2-carboxylic acid ethyl ester (8.07 g, 21 mmol), sodium hydroxide (6.32 g, 160 mmol), methanol (360 ml), and water (26.8 ml) analogously to example 1/2. The precipitate was washed and dried. It was used in the next step without further purification. Yield: 6.63 g (89%). M.p. 230–233° C.

3.) 5-Bromo-1-(3-cyano-benzyl)-1H-indole-2-carboxylic acid 4-dimethylamino-benzylamide This compound was prepared from 5-bromo-1-(3-cyano-benzyl)-1H-indole-2-carboxylic acid (1 g, 2.8 mmol), diphenylphosphoryl azide (790 μl, 3.66 mmol), N,N-diisopropylethylamine (960 μl, 5.6 mmol), and 4-(dimethylamino)-benzylamine dihydrochloride (703 mg, 3.1 mmol) in N,N-dimethylformamide (40 ml) as described in example 3/1. The purification by flash chromatography on silica gel was done with dichloromethane/methanol 20:0.05 to give 949 mg (69 %) of the desired product. M.p. 145–146° C.

4.) [4-({[5-Bromo-1-(3-cyano-benzyl)-1H-indole-2-carbonyl]-amino}-methyl)-phenyl]-trimethyl-ammonium iodide This compound was prepared from 5-bromo-1-(3-cyano-benzyl)-1H-indole-2-carboxylic acid 4-dimethylamino-benzylamide (890 mg, 1.83 mmol), methyl iodide (2.95 ml, 47 mmol), and acetone (8 ml) analogously to example 20/1. Yield: 1.289 g. M.p. 145–148° C. The compound was used for the next steps without further purification.

5.) [4-({[1-(3-Amidino-benzyl)-5-bromo-1H-indole-2-carbonyl]-amino}-methyl)-phenyl]-trimethyl-ammonium acetate acetic acid salt This compound was prepared from [4-({[5-bromo-1-(3-cyano-benzyl)-1H-indole-2-carbonyl]-amino}-methyl)-phenyl]-trimethyl-ammonium iodide (200 mg, 0.32 mmol), ethanol, hydrogen chloride, and liquid ammonia analogously to example 19/3. Purification by reversed phase chromatography on RP$_{18}$ material with water/ethanol/trifluoroacetic acid 1:1:0.1 gave 199 mg of the desired product as trifluoroacetic acid salt. This compound was converted into the acetic acid salt by ion exchange chromatography analogously to example 64. Yield: 130 mg (64 %). M.p. 86° C. (dec.). MS: 520.2 (M$^+$; $^{81}$Br).

Example 72

1-(3-Amidino-benzyl)-1H-indole-3-carboxylic acid 3-amidino-benzyl amide trifluoroacetic acid salt

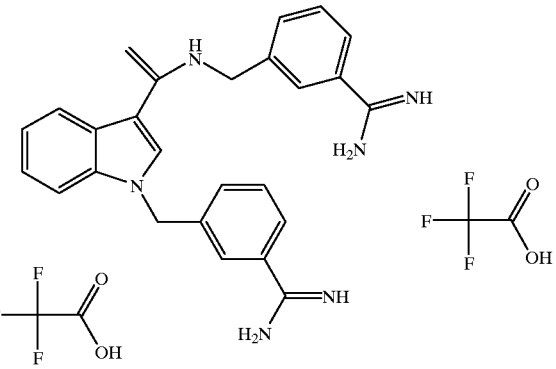

1.) 1-(3-Cyano-benzyl)-1H-indole-3-carboxylic acid 3-cyano-benzylamide

This compound was prepared from 1-(3-cyano-benzyl)-1H-indole-3 carboxylic acid (1 g, 3.62 mmol, example 1911), diphenylphosphoryl azide (1.29 g, 4.70 mmol), N,N-diisopropylethylamine (1.82 ml), and 3-cyano-benzyl amine hydrobromide (1.16 g, 3.3 mmol) in N,N-dimethylformamide (50 ml) as described in example 3/1. The purification by flash chromatography on silica gel was done with toluene/ethyl acetate first 19:0.25, then 19:0.5, to give 289 mg (20%) of the desired product. MS: 391.2 (M+H$^+$).

2.) 1-(3-Amidino-benzyl)-1H-indole-3-carboxylic acid 3-amidino-benzylamide trifluoroacetic acid salt This compound was prepared from 1-(3-cyano-benzyl)-1H-indole-3-carboxylic acid 3-cyano-benzylamide (280 mg, 0.72 mmol), ethanol, hydrogen chloride, and liquid ammonia analogously to example 19/3. Purification by MPLC on RP$_{18}$ material with water/ethanol/trifluoroacetic acid 7:3:0.1 gave 110 mg of the desired product. M.p. 146–148° C. MS: 425.2 (M+H$^+$).

Example 73

1-(3-Pyridyl)-methyl-1H-indole-2-carboxylic acid 4-dimethylamino-benzylamide

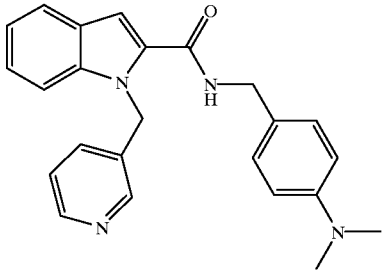

1.) 1-(3-Pyridyl-methyl)-1H-indole-2 carboxylic acid ethyl ester

This compound was prepared from 1H-indole-2-carboxylic acid ethyl ester (1 g, 5.28 mmol), sodium hydride (139.5 mg, 5.8 mmol), 3-chloromethyl-pyridine (2.05 g, 15.8 mmol), dimethylsulfoxide (10 ml), and N,N-dimethylformamide (60 ml) analogously to example 21/1. The precipitate was partitioned between ethyl acetate and hydrochloric acid, 162 mg and the organic layer was dried and evaporated to give 437.1 mg (45%) of the desired product. M.p. 92–93° C. MS: 281.4 (M+H$^+$).

2.) 1-(3-Pyridyl-methyl)-1H-indole-2-carboxylic acid

This compound was prepared from 1-(3-pyridyl-methyl)-1H-indole-2-carboxylic acid ethyl ester (313 mg, 1.1 mmol), 1 N sodium hydroxide solution in water (5.58 ml), and ethanol (25 ml). The ester was dissolved in ethanol, the sodium hydroxide solution was added and the mixture was heated to 400C. After 2.5 h the heating was removed and the reaction mixture was neutralized with 1 N hydrochloric acid (5.58 ml). The solution was partitioned between water and ethyl acetate and the organic layer was dried and evaporated to give 251 mg of the desired product (89%). MS: 253.1 (M+H$^+$).

3.) 1-(3-Pyridyl-methyl)-1H-indole-2-carboxylic acid 4-dimethylamino-benzylamide This compound was prepared from 1-(3-pyridyl-methyl)-1H-indole-2-carboxylic acid (200 mg, 0.79 mmol), diphenylphosphoryl azide (222.7 µl, 1.03 mmol), N,N-diisopropylethylamine (364 µl), and 4-dimethylamino-benzylamine dihydrochloride (632.3 mg, 2.84 mmol) in N,N-dimethylformamide (10 ml) as described in example 3/1. The purification by flash chromatography on silica gel was done with toluene/ethyl acetate first 6:1, then going to pure ethyl acetate in two steps: 228.7 mg (76%) of the desired product were obtained. M.p. 108–110° C. MS: 385.3 (M+H$^+$).

Examples 74–78 were synthesized on solid phase using a polystyrene (PS) resin with a 2-chlorotritylchloride linker (L). (substitution 1.05 mmol/g and 0.67 mmol/g, respectively; Novabiochem).

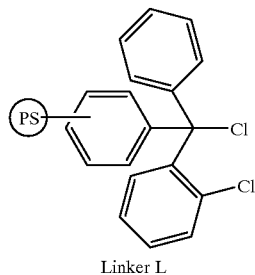

Linker L

The general procedures applied in examples 74 to 78 are as follows.

Linking

The indole derivatives were dissolved in dichloromethane or dichloromethane tetrahydrofurane mixtures. N,N-diisopropylethylamine was added and the mixture was sucked into a syringe fitted with a polyethylene sheet and containing the resin. After shaking for 2 hours at room temperature the mixture was removed and the resin was washed with dichloromethane. A mixture of methanol, N,N-diisopropylethylamine, and dichloromethane was added and the syringe was shaken at room temperature. After 1.5 hours the mixture was removed and the resin was washed with N,N-dimethylformamide (1×), dichloromethane (3×), and methanol (3×).

Cleaving

The compounds were cleaved from the resin by treating the resin with a mixture of dichloromethane, trifluoroacetic acid, and water (60:40:0.1). After 15 minutes the cleavage mixture was transferred into a flask and the resin was washed with methanol (3×). The methanol washes were added to the cleavage mixture and the resulting solution was evaporated in vacuo. The residue was dissolved in an appropriate acetonitirile-water mixture and characterized by HPLC and MS (Beckman HPLC used with the following columns: A: YMC ODS-AM 4.6 mm×250 mm; B: VYDAC RP-18, 90 Å, 4.6 mm×250 mm; C: YMC basic, 4.6 mm×250 mm: Thermo Separation Products HPLC used with column D: Macherey-Nagel ET 250/8/4 Nucleosil 7 C$_{18}$).

Purification

The final products were purified by preparative HPLC using the following conditions:

System 1 used for examples 74–78: Beckman HPLC, column: VYDAC Protein & Peptide, C$_{18}$, 10 µm, 22×250 mm; flow 8 ml/min, acetonitrile/water-gradient, wavelength 324 nm, or System 2 used for all other compounds synthesized on solid phase: Thermo Separation Products HPLC, column: Macherey-Nagel 100 7 C$_{18}$, 20 mm×250 mm; flow 5–6 ml/min, appropriate mixtures of water (70–60%) and acetonitrile (30–40%), wavelength 236–242 nm.

Example 74

4-(((1-(3-Amidino-benzyl)-5-amino-1H-indole-2-carbonyl)-amino)-methyl)-1-methyl-pyridinium trifluoroacetate trifluoroacetic acid salt

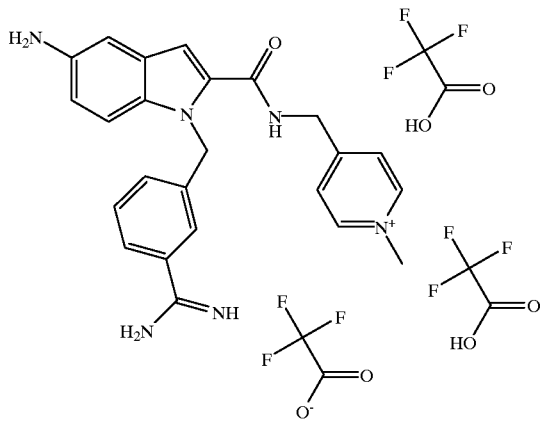

1.) 5-Amino-1-(3-cyano-benzyl)-1H-indole-2-carboxylic acid ethyl ester trifluoroacetic acid salt 5-Amino-1H-indole-2-carboxylic acid ethyl ester (343 mg, 1.68 mmol) was coupled to the resin (529 mg, 0.56 mmol) as described above. The dry indole-coupled resin was shaken in dry N,N-dimethylformamide for 5 min. After removal of the N,N-dimethylformamide a mixture of 2-tert-butylimino-2-diethylamino-1,3-dimethylperhydro-1,3,2-diazaphosphorine (405 µl; 1.4 mmol) and N,N-dimethylformamide (5 ml) was added followed by a solution of 3-cyano-benzyl bromide (220 mg, 1.12 mmol) in N,N-dimethylformamide after 1 hour. 3 hours later the mixture was removed, the resin was washed with N,N-dimethylformamide (5×) and methanol (5×) and dried in vacuo. A sample was taken and cleaved as described above. The compound obtained was characterized by HPLC and MS.

HPLC: column B. 0–60% acetonitrile in water, 30 min, 324 nm, retention time: 16.88 min. MS: 320.1 (M+H$^+$).

2.) 5-Amino-1-(3-cyano-benzyl)-1H-indole-2-carboxylic acid trifluoroacetic acid salt The resin from step 1 (331 mg) was shaken for 5 minutes with N,N-dimethylformamide (8 ml). After the removal of the N,N-dimethylformamide a mixture of benzyl-trimethyl-ammonium hydroxide (40% in methanol; 2.8 mmol, 1.27 ml) and N,N-dimethylformamide (10 ml) was sucked in and shaken for 4 h 40 min. After removal of the mixture the resin was washed with N,N-dimethylformamide (5×) and dichloromethane (3×) and dried in vacuo. A sample was taken and cleaved.

HPLC: column B. 0–60% acetonitrile in water, 30 min, 324 nm, retention time: 11.72 min. MS: 292.1 (M+H$^+$).

3.) 5-Amino-1-(3-cyano-benzyl)-1H-indole-2-carboxylic acid (4-pyridylmethyl)-amide trifluoroacetic acid salt The resin from step 2 (105 mg) was shaken for 5 minutes with N,N-dimethylformamide, before the reagent mixture consisting of 4-(aminomethyl)pyridine (34 µl, 0.33 mmol), N,N'-diisopropylcarbodiimide (49 mg, 0.39 mmol), and 1-hydroxybenzotriazole hydrate (53 mg, 0.39 mmol) in N,N-dimethylformamide (4 ml) was added. After 22 hours the reaction mixture was removed and the resin was washed with N,N-dimethylformamide, methanol, and dichloromethane and dried in vacuo. A sample was taken and cleaved.

HPLC: column B, 0–60% acetonitrile in water, 30 min, 324 nm, retention time: 9.73 min. MS: 382.1 (M+H$^+$).

4.) 5-Amino-1-(3-thiocarbamoyl-benzyl)-1H-indole-2-carboxylic acid (4-pyridyl-methyl)-amide trifluoroacetic acid salt The resin from step 3 (45 mg) was shaken in 2 ml pyridine/triethylamine (2:1) for 15 minutes. The solution was removed, a saturated solution of hydrogen sulfide in pyridine/triethylamine (2:1) (1 ml) was added and the mixture was shaken overnight.

The next day the hydrogen sulfide solution was removed. The resin was washed with acetone and dried in vacuo. A sample was taken and cleaved.

HPLC: column C, 0–60% acetonitrile in water, 30 min, 324 nm, retention time: 14.30 min. MS: 416.0 (M+H$^+$).

5.) 4-(((1-(3-Amidino-benzyl)-5-amino-1H-indole-2-carbonyl)-amino)-methyl)-1-methyl-pyridinium trifluoroacetate trifluoroacetic acid salt 5.1) To 10 mg of the resin from step 4 a solution of methyl iodide (100 µl) in acetone (0.4 ml) was added. After shaking overnight the reaction mixture was removed and the resin was washed with acetone (7×) and methanol. A solution of ammonium acetate (31 mg), acetic acid (15 µl), and methanol (300 µl) was added. The syringe was closed and heated in a water bath at 50° C. for 3 hours. After this conversion the solution was removed and the resin was washed with methanol, N,N-dimethylformamide, and dichloromethane.

5.2) To 10 mg of the resin from step 4 a solution of N,N-dimethylformamide (0.4 ml) and methyl iodide (100 µl) was added. After shaking overnight the reaction mixture was removed and the resin was washed with acetone (7×) and methanol. A solution of ammonium acetate (31 mg), acetic acid (15 [µl], and methanol (300 µl) was added. The syringe was closed and heated in a water bath at 50° C. for 3 hours. After this conversion the solution was removed and the resin was washed with methanol, N,N-dimethylformamide, and dichloromethane.

5.3) The resin from step 4 (25 mg) was shaken with acetone for 5 minutes. The acetone was replaced by a solution of methyl iodide (0.3 ml) in acetone (1.2 ml) and the syringe was shaken overnight. The next day the methyl iodide solution was removed and the resin washed with acetone and methanol. A solution of ammonium acetate (92 mg), acetic acid (45 µl), and methanol (300 µl) was added and the syringe heated at 50° C. for 3 hours. The solution was removed and the resin washed with methanol, N,N-dimethylformamide, and dichloromethane.

The resins obtained in steps 5.1–5.3 were pooled. The combined material was cleaved and then purified by preparative HPLC. After lyophilization 8 mg of a solid material was obtained. M.p. 115° C.

HPLC:column C, 0–40% acetonitrile in water, 20 min, 230 nm, retention time: 11.05 min. MS: 413.0 (M$^+$).

Examples 75 and 76

1-(3-Amidino-benzyl)-5-amino-1H-indole-2-carboxylic acid 4-amidino-benzylamide trifluoroacetic acid salt (example 75)

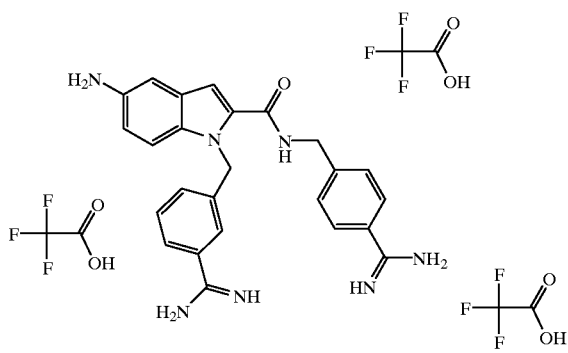

and 1-(3-Amidino-benzyl)-5-amino-1H-indole-2-carboxylic acid 3-amidino-benzylamide trifluoroacetic acid salt (example 76)

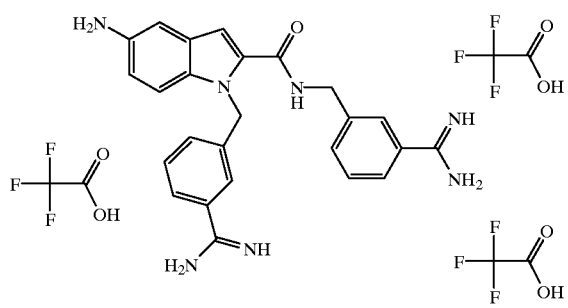

1.) 5-Amino-1-(3-cyano-benzyl)-1H-indole-2-carboxylic acid 4-cyano-benzylamide trifluoroacetic acid salt and 5-Amino-1-(3-cyano-benzyl)-1H-indole-2-carboxylic acid 3-cyano-benzylamide trifluoroacetic acid salt 1.1) The resin from example 74 step, 2 (130 mg, 0.11 mmol) was shaken with N,N-dimethylformamide for 5 minutes. After removal of the N,N-dimethylformamide a solution of diphenylphosphoryl azide (36 µl, 0.165 mmol), N,N-diisopropylethylamine (172 µl; 0.99 mmol), and 4-aminomethyl-benzonitrile hydrobromide (70 mg, 0.33 mmol) in N,N-dimethylformamide (4 ml) was added and the syringe was shaken overnight. After 16 h the reaction mixture was removed, the resin washed with N,N-dimethylformamide, methanol, and dichloromethane and dried. After drying a sample was taken and cleaved. HPLC analysis showed a conversion of 50%.

1.2) The resin from step 1.1 was shaken with N,N-dimethylformamide for 5 minutes. The removal of N,N-dimethylformamide was followed by the addition of the reagent mixture consisting of 3-aminomethyl-benzonitrile (22 mg, 0.165 mmol), 1-hydroxybenzotriazole (30 mg; 0.22 mmol), N,N'-diisopropylcarbodiimide (24 mg; 0.193 mmol), and N,N-dimethylformamide (2 ml). After shaking for 16 hours the reagent mixture was removed, the resin washed with N,N-dimethylformamide, methanol, and dichloromethane and dried. A sample was taken and cleaved.

HPLC: column C, 0–60% acetonitrile in water, 30 min, 324 nm, retention time: 23.70 min (peak showed a shoulder).

2.) 5-Amino-1-(3-thiocarbamoyl-benzyl)-1H-indole-2-carboxylic acid 4-thiocarbamoyl-benzylamide trifluoroacetic acid salt and 5-Amino-1-(3-thiocarbamoyl-benzyl)-1H-indole-2-carboxylic acid 3-thiocarbamoyl-benzylamide trifluoroacetic acid salt The resin obtained in step 1.2 was treated with hydrogen sulfide, pyridine, and triethylamine as described in example 74/4. Due to the fact that there still was some starting material present it was treated once again with hydrogen sulfide, pyridine, and triethylamine to get complete conversion. After cleavage of a small sample the compounds obtained were characterized by HPLC analysis.

HPLC: column C, 0–60% acetonitrile in water, 30 min, 324 nm, retention time: 20.17 min (53%), 20.52 min (32%).

3.) 1-(3-Amidino-benzyl)-5-amino-1H-indole-2-carboxylic acid 4-amidino-benzylamide trifluoroacetic acid salt and 1-(3-Amidino-benzyl)-5-amino-1H-indole-2-carboxylic acid 3-amidino-benzylamide trifluoroacetic acid salt The resin from step 2 was treated with methyl iodide (250 µl, 4 mmol), acetone (2 ml), ammonium acetate (210 mg, 2.7 mmol), acetic acid (100 µl), and methanol (2 ml) analogously to example (74/5.3). The compounds were cleaved from the resin. After evaporation the residue was dissolved in acetonitrile/water 15:85 (400 µl). Preparative HPLC of the residue resulted in two main fractions. Fraction I contained meta-para-amidine with an impurity of bis-meta-amidine, Fraction II contained bis-meta-amidine with an impurity of meta-para-amidine.

A second preparative HPLC of fraction I gave 10.2 mg of the meta-para-amidine (example 75) as a white solid. M.p. 146° C. (dec.).

HPLC: column C, 0–40% acetonitrile in water, 20 min, 230 nm, retention time: 12.45 min. MS: 439.9 (M+H+).

A second preparative HPLC of fraction II gave 12.5 mg of the bis-meta-amidine (example 76). M.p. 125° C. (dec.).

HPLC: column C, 0–40% acetonitrile in water, 20 min, 230 nm, retention time: 12.57 min. MS: 440.0 (M+H+).

Example 77

1-(3-Amidino-benzyl)-4-hydroxy-1H-indole-2-carboxylic acid 3-amidino-benzylamide trifluoroacetic acid salt

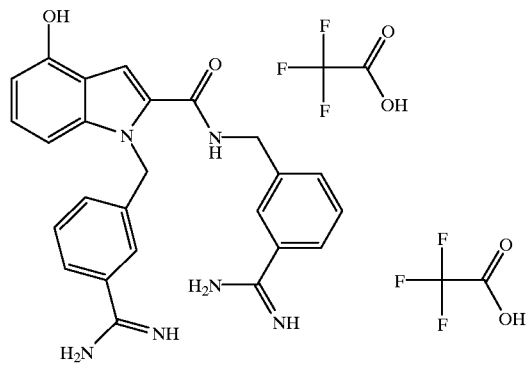

1.) 1-(3-Cyano-benzyl)-4-hydroxy-1H-indole-2-carboxylic acid ethyl ester

4-Hydroxy-1H-indole-2-carboxylic acid ethyl ester (345 mg, 1.69 mmol) was coupled to the resin (535 mg, 0.56 mmol). Then the resin was shaken in dry N,N-dimethylformamide for 5 minutes, washed with N,N-dimethylformamide and a mixture of 2-tert-butylimino-2diethylamino-1,3-dimethylperhydro-1,3,2-diazaphosphorine (405 µl, 1.4 mmol) and N,N-dimethylformamide (5 ml) was added to the resin. After shaking for 1 hour 3-cyano-benzyl bromide (220 mg, 1.12 mmol) was added. 3 hours later the mixture was removed, the resin was washed with N,N-dimethylformamide (5×) and methanol (5×) and dried in vacuo. After cleavage of a small sample the product was characterized by HPLC.

HPLC: column B, 0–80% acetonitrile in water, 40 min, 324 nm, retention time: 25.53 min.

2.) 1-(3-Cyano-benzyl)-4-hydroxy-1H-indole-2-carboxylic acid

The resin obtained in step 1 was treated with benzyl-trimethyl-ammonium hydroxide (40% in methanol, 2.5 ml, 5.6 mmol) in N,N-dimethylformamide (15 ml) analogously to the resin in example 74/2. A sample was taken and cleaved.

HPLC: column B, 0–60% acetonitrile in water, 30 min, 324 nm, retention time: 20.98 min.

3.) 1-(3-Cyano-benzyl)-4-hydroxy-1H-indole-2-carboxylic acid 3-cyano-benzylamide The resin obtained in step 2 (98 mg, 0.1 mmol) was reacted with a mixture of 3-aminomethyl-benzonitrile hydrobromide (64 mg; 0.3 mmol), N,N-diisopropylethylamine (70 µl, 0.4 mmol), 1-hydroxybenzotriazole (54 mg, 0.4 mmol), and N,N'-diisopropylcarbodiimide (44 mg, 0.35 mmol) analogously to examples 75 and 76, step 1.2.

4) 4-Hydroxy-1-(3-thiocarbamoyl-benzyl)-1H-indole-2-carboxylic acid 3-thiocarbamoyl-benzylamide The resin obtained in step 3 was treated with hydrogen sulfide, pyridine, and triethylamine as described in example 74.4.

5.) 1-(3-Amidino-benzyl)-4-hydroxy-1H-indole-2-carboxylic acid 3-amidino-benzylamide trifluoroacetic acid salt The resin obtained in step 4 was treated with methyl iodide (250 µl, 4 mmol), acetone (2 ml), ammonium acetate (210 mg, 2.7 mmol), acetic acid (100 µl), and methanol (2 ml) analogously to example 74, step 5.3. Preparative HPLC after cleavage: The residue was dissolved in water and acetonitrile to give 900 µl of volume. This solution was split in two parts and each part was separated by HPLC to yield a total amount of 11 mg of a white solid. M.p. 128–131° C. HPLC: column B, 0–40% acetonitrile in water, 20 min, 230 nm, retention time: 11.97 min. MS: 441.0 (M+H⁺).

Example 78

1-(3-Amidino-benzyl)-4-hydroxy-1H-indole-2-carboxylic acid 4-amidino-benzylamide trifluoroacetic acid salt

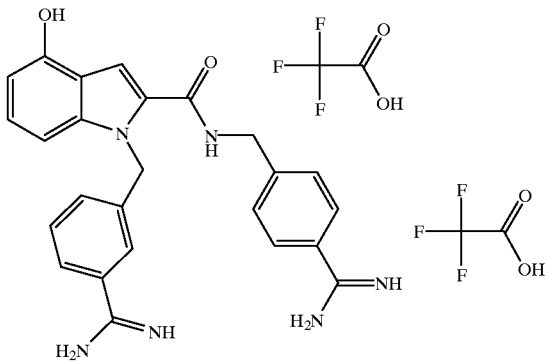

1.) 1-(3-Cyano-benzyl)-4-hydroxy-1H-indole-2-carboxylic acid 4-cyano-benzylamide 50 mg (0.05 mmol) of the resin obtained in example 77/2 was reacted with a mixture of 4-aminomethyl-benzonitrile hydrobromide (32 mg, 0.15 mmol), N,N-diisopropylethylamine (35 µl, 0.2 mmol), 1-hydroxybenzotriazole (27 mg, 0.2 mmol), and N,N'-diisopropylcarbodiimide (22 mg; 0.175 mmol), analogously to example 74/3.

2.) 4-Hydroxy-1-(3-thiocarbamoyl-benzyl)-1H-indole-2-carboxylic acid 4-thio-carbamoyl-benzylamide The resin obtained in step 1 was treated with hydrogen sulfide, pyridine, and triethylamine as described in example 74/4.

3.) 1-(3-Amidino-benzyl)-4-hydroxy-1H-indole-2-carboxylic acid 4-amidino-benzyl amide trifluoroacetic acid salt The resin obtained in step 2 was treated with methyl iodide (125 µl, 2 mmol), acetone (1 ml), ammonium acetate (105 mg, 1.35 mmol), acetic acid (50 µl), and methanol (1 ml) analogously to example 75/5.3. Preparative HPLC after cleavage: The residue was dissolved in water and acetonitrile and purified to yield 7 mg of a white solid. M.p. 155–157° C.

HPLC: column B, 0–40% acetonitrile in water, 20 min, 324 nm, retention time: 11.77 min. MS: 441.0 (M+H⁺).

Example 79

1-(3-Amidino-benzyl)-4-hydroxy-1H-indole-2-carboxylic acid [2-(2,4-dichloro-phenyl)ethyl]-amide trifluoroacetic acid salt

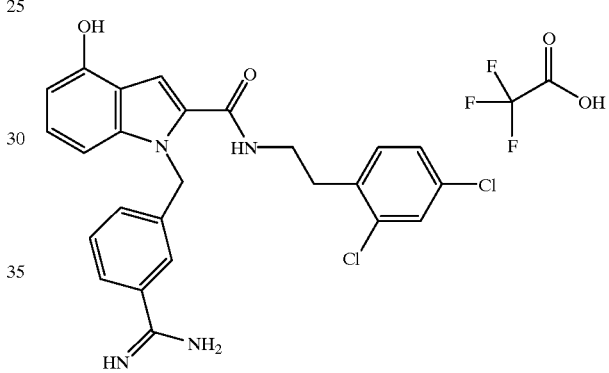

1.) 1-(3-Cyano-benzyl)-4-hydroxy-1H-indole-2-carboxylic acid [2-(2,4-dichloro-phenyl)ethyl]-amide This compound was synthesized using a substituted resin like the one described in example 77/2 but with a lower substitution (the 2-chlorotritylchloride resin used in the linking step only had a substitution of 0.67 mmol/g). This resin (300 mg, 0.201 mmol) carrying 1-(3-cyano-benzyl)-4-hydroxy-1H-indole-2-carboxylic acid was treated with N,N-dimethylformamide for five minutes. After removal of the N,N-dimethylformamide a mixture of 2-(2,4-dichloro-phenyl)-ethylamine (0.51 ml, 3.35 mmol), N,N-diisopropylethylamine (0.57 ml, 3.35 mmol), diphenylphosphoryl azide (0.72 ml, 3.35 mmol), and N,N-dimethylformamide (6 ml) was added. After shaking overnight the reaction mixture was removed and the resin washed with N,N-dimethylformamide (5×) and methanol (5×). After drying in vacuo a sample was taken and cleaved.

HPLC: column D; water/acetonitrile 90:10 to 10:90, 30 min, 324 nm, retention time: 23.10 min.

2.) 4-Hydroxy-1-(3-thiocarbamoyl-benzyl)-1H-indole-2-carboxylic acid [2-(2,4-dichloro-phenyl)-ethyl]-amide The resin from example 79/1 was similarly treated as described in example 74/4.

HPLC: column D, water/acetonitrile 90:10 to 10:90, 30 min, 324 nm, retention time: 20.74 min.

3.) 1-(3-Amidino-benzyl)-4-hydroxy-1H-indole-2-carboxylic acid [2-(2,4-dichloro-phenyl)ethyl]-amide trifluoroacetic acid salt The resin from example 79/2 was similarly treated as described in example 74/5.3. Preparative HPLC after cleavage gave 20 mg of a white solid. M.p. 144° C. HPLC: column D, water/acetonitrile 45:55, 30 min, 236 nm, retention time 9.43 min. MS: 481.2 (M+H$^+$; 2×$^{35}$Cl).

Example 80

1-(2-(4-Aminophenyl)ethyl)-1H-indole-2-carbonyl-L-arginyl amide trifluoroacetic acid salt

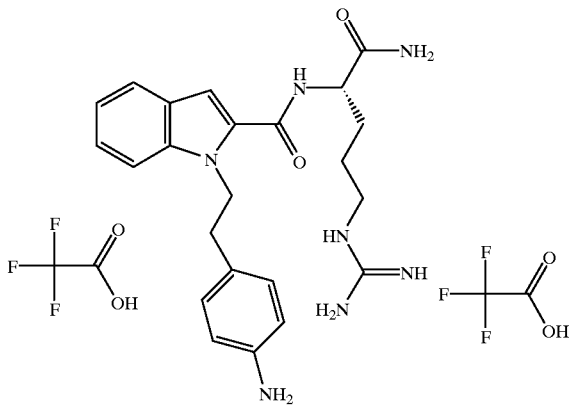

1.) 1-(2-(4-Nitrophenyl)ethyl)-1H-indole-2-carboxylic acid

1H-Indole-2-carboxylic acid ethyl ester(1.027 g, 5.4 mmol) was dissoved in 15 ml of dry dimethylformamide and stirred under nitrogen in an ice-bath. Sodium hydride (60% in paraffin oil; 274 mg, 6.85 mmol) was added and the solution stirred at room temperature for 1.5 hours. To the reaction mixture 2-(4-nitrophenyl)ethyl bromide (1.29 g, 5.6 mmol) was added and the solution was stirred overnight. The reaction mixture was heated for 4 hours at 60° C. After completion of the reaction (thin layer chromatography, chloroform/methanol/acetic acid 90:9:1) 20 ml of 2 N hydrochloric acid was added and the reaction mixture was extracted with ethyl acetate. The ethyl acetate layer was washed with water, dried with magnesium sulfate, and evaporated to give an orange-red oil. The oily product was taken up in methanol/water (15 ml), and 1.2 g of potassium hydroxide were added. The reaction mixture was stirred overnight to complete the hydrolysis. Workup was achieved by addition of 2 N hydrochloric acid and extraction with ethyl acetate. Washing of the ethyl acetate layer with water, drying with magnesium sulfate, and evaporation in vacuo gave 1(2-(4-nitrophenyl)-ethyl)-1H-indole-2-carboxylic acid. MS: 310.2.

2.) 1-(2-(4-Aminophenyl)-ethyl)-1H-indole-2-carbonyl-arginyl amide trifluoroacetic acid salt 1-(2-(4-Nitrophenyl)ethyl)-1H-indole-2-carboxylic acid (250 mg, 0.8 mmol) was coupled to 0.54 g of Rink-L-arginyl resin (sub. 0.52 mmol/g) in the presence of N,N'-diisopropylcarbodiimide/1-hydroxybenzotriazole in dimethylformamide. After completion of coupling, the resin was washed with dimethylformamide/dichloromethane and cleaved with 95% trifluoroacetic acid for 3 hours. After evaporation of the trifluoroacetic acid and lyophilization the crude 1-(2-(4-nitrophenyl)-ethyl)-1H-indole-2-carbonyl-L-arginyl amide was dissolved in methanol/water (60 ml) and hydrogenated in the presence of Raney Ni catalyst at 30 psi (2.07 hPa) for 3 hours. Filtration of catalyst, evaporation of the solvent and lyophilization of the residue gave the crude title compound which was purified by HPLC on a C$_{18}$ column (Vydac). MS: 435.2.

Example 81

1-(4-Amidinobenzyl)-1H-indole-2-carbonyl-L-arginyl amide trifluoroacetic acid salt

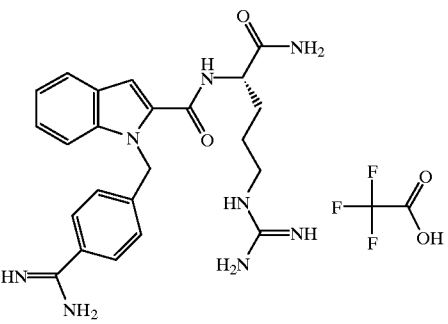

1.) 1-(4-Amidinobenzyl)-1H-indole-2-carboxylic acid hydroiodide

1H-Indole-2-carboxylic acid ethyl ester (266 mg, 1.4 mmol) and lithium hydroxide (177 mg) were dissolved in 4 ml of dry dimethylsulfoxide. The solution was sonicated for 5 minutes and then 4-cyano-benzyl bromide (266 mg, 1.37 mmol) dissolved in 1.5 ml of dimethylsulfoxide was slowly added. The reaction mixture was stirred overnight at room temperature. Workup was achieved by addition of 10 ml of 1:1 mixture of methanol and water and stirring of the reaction mixture at room temperature for 6 hours. The reaction mixture was then acidified with 2 N hydrochloric acid and extracted with ethyl acetate. The combined organic layers were washed with water, dried with magnesium sulfate and evaporated to dryness to give a residual solid. The product was purified by chromatography on silica gel with ethyl acetate/hexane 5:1 and crystallized from methanol/water to give 202 mg of a white solid having NMR spectra in line with the expected 1-(4-cyano-benzyl)-1H-indole-2-carboxylic acid.

Hydrogen sulfide gas was bubbled through a solution of 1-(4-cyano-benzyl)-1H-indole-2-carboxylic acid (202 mg) in 25 ml of pyridine/triethylamine 4:1. After stirring the green solution for 16 hours, the reaction mixture was concentrated in vacuo. The residue was dissolved in ethyl acetate and washed with 2 N hydrochloric acid. The layers were separated and the ethyl acetate layer was washed with saturated sodium chloride solution, dried over anhydrous magnesium sulfate, filtered, and concentrated to give the crude thioamide. The thioamide was dissolved in acetone (25 ml). 1.5 ml of methyl iodide were added and the reaction mixture was stirred for 8 hours. The reaction mixture was then concentrated in vacuo to dryness, the residue was dissolved in 30 ml of methanol and 2.9 g of ammonium acetate were added. The reaction mixture was sonicated and heated at 60° C. for 15 minutes followed by stirring at room temperature for 12 hours. The precipitated solid was filtered, washed with ether and dried in vacuo . The crude 1-(4-amidino-benzyl)-1H-indole-2-carboxylic acid hydroiodide was identified by mass spectrometry, and its purity was checked by HPLC. It was used in the next step without further purification 2.) 1-(4-Amidino-benzyl)-1H-indole-2-carbonyl-L-arginyl amide trifluoroacetic acid salt 1-(4-Amidino-benzyl)-1H-indole-2-carboxylic acid hydroiodide (182 mg, 0.6 mmol) was coupled to 0.5 g of Rink-L-arginyl resin (sub. 0.52 mmol/g) in the presence of N,N'-diisopropylcarbodiimide/1-hydroxybenzotriazole in dimethylformamide for 8 hours. After completion of coupling, the resin was washed with dimethylformamide/dichloromethane and cleaved with 95% trifluoroacetic acid for 3 hours. Evaporation of the trifluoroacetic acid and lyophilization of the residue gave the title compound. The crude product was purified by HPLC on a C$_{18}$ column (Vydac). MS: 448.2.

Example 82

1-(N-(4-Amidino-phenyl)-carbamoyl-methyl)-1H-indole-2-carboxylic acid ethyl ester hydroiodide

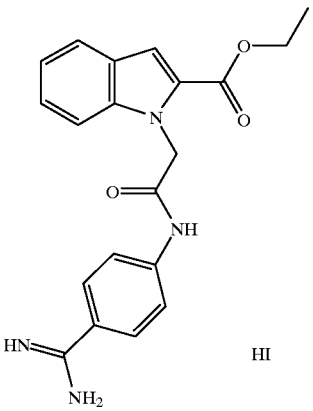

1.) 1-(tert-Butyloxycarbonyl-methyl)-1H-indole-2-carboxylic acid ethyl ester

This compound was synthesized from 1H-indole-2-carboxylic ethyl ester and tert-butyl bromoacetate using potassium tert-butoxide in dimethylformamide with a similar technique as described in example 79. The intermediate was characterized by NMR spectroscopy.

2.) 1-(Chlorocarbonyl-methyl)-1H-indole-2-carboxylic acid ethyl ester 1-(tert-Butyloxycarbonyl-methyl)-1H-indole-2-carboxylic acid ethyl ester was treated with trifluoroacetic acid in dichloromethane to give 1-(carboxy-methyl)-1H-indole-2-carboxylic ethyl ester. Reaction of the latter intermediate with oxalyl chloride in dichloromethane gave the title compound.

3.) 1-(N-(4-Cyano-phenyl)-carbamoyl-methyl)-1H-indole-2-carboxylic acid ethyl ester 1-(Chlorocarbonyl-methyl)-1H-indole-2-carboxylic acid ethyl ester was reacted with 4-cyano-aniline in dichloromethane in the presence of N,N-diisopropylethylamine. Workup of the reaction mixture gave the title compound.

4.) 1-(N-(4-Amidino-phenyl)-carbamoyl-methyl)-1H-indole-2-carboxylic acid ethyl ester 1-(N-(4-Cyano-phenyl)carbamoyl-methyl)-1H-indole-2-carboxylic acid ethyl ester was converted into the amidine using hydrogen sulfide, methyl iode, and ammonium acetate (without acetic acid) analogously to example 1/4 and 1/5 (example 80). The title compound was characterized by mass spectrometry and purified by HPLC. MS: 364.2).

Example 83

N-(3-Amidino-benzyl)-2-[1-(3-amidino-benzyl)-1H-indol-3-yl]-acetamide trifluoroacetic acid salt

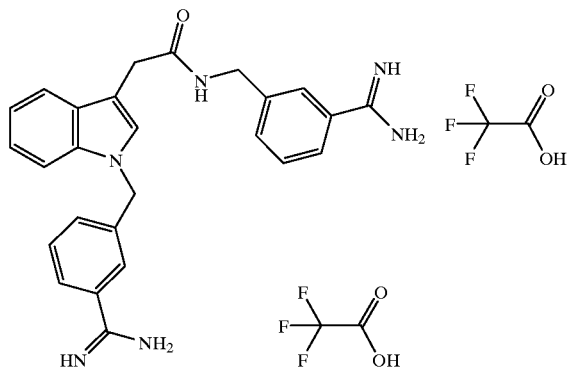

1.) N-(3-Cyano-benzyl)-2-(1H-indol-3-yl)-acetamide

To a solution of 4 g (22.8 mmol) of (1H-indol-3-yl)-acetic acid in 90 ml of dimethylformamide a solution of 3.85 g (22.8 mmol) of 3-aminomethyl-benzonitrile and 3.88 ml (22.8 mmol) of ethyl-diisopropyl-amine in 10 ml of dimethylformamide and 3.5 g (22.8 mmol) of 1-hydroxybenzotnazole hydrate were added at 0° C. After stirring for 30 minutes 5.17 g (25.1 mmol) of dicyclohexylcarbodiimide was added. After 1 hour the mixture was warmed up to room temperature and stirred for 36 hours. The precipitate was filtered off and the filtrate was concentrated in vacuo. The residue was dissolved in ethyl acetate, washed with sodium bicarbonate solution, brine and water, dried, and evaporated. The crude product was purified by flash chromatography on silica gel by using first dichloromethane/ethyl acetate (9:1, later 7:3) and second dichloromethane/methanol 9:1 to give the desired product in 71% yield as an oil. MS: 290.2 (M+H$^+$).

2.) N-(3-Amidino-benzyl)-2-[1-(3-amidino-benzyl)-1H-indol-3-yl]-acetamide trifluoroacetic acid salt The title compound was prepared from N-(3-cyano-benzyl)-2-(1H-indol-3-yl)-acetamide, 3-cyano-benzyl bromide, and 2.2 equivalents of sodium hydride analogously to example 21/1 and example 1/4 and 1/5. The crude product was purified by flash chromatography on RP$_{18}$ material with water/ethanol/trifluoroacetic acid 7:3:0.1 to give the title compound in 22% yield. M.p. 196° C. (dec.). MS: 439.3 (M$^+$).

Example 84

2-(4-Amidino-benzoyl)-9-(3-amidino-benzyl)-1,2,3,4-tetrahydro-9H-pyrido[3,4-b]indole trifluoroacetic acid salt

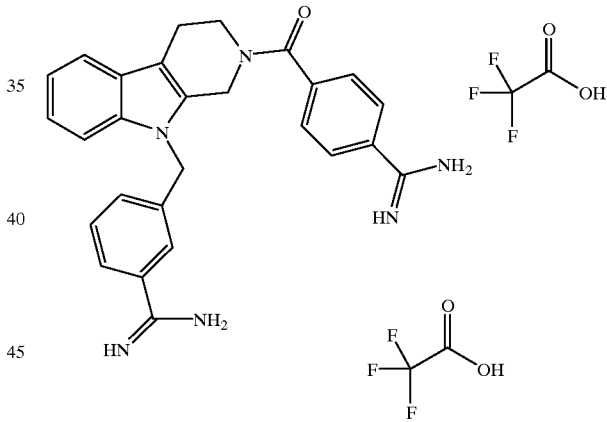

1.) 2-(4-Cyano-benzoyl)-1,2,3,4-tetrahydro-9H-pyrido[3,4-b]indole

A mixture of 175 mg of 1,2,3,4-tetrahydro-9H-pyrido[3,4-b]indole, 5 ml of dimethylformamide, 0.2 g of 4-cyano-benzoic acid, 0.35 g of diphenylphosphoryl azide and 0.4 ml of diisopropylethylamine was stirred at room temperature over night. The solvent was removed under reduced pressure and the residue was partitioned between methylene chloride and 10% aqueous sodium carbonate solution. The organic phase was washed with 1 N hydrochloric acid, dried over magnesium sulfate and evaporated. Crystallization of the residue from methylene chloride/ether yielded 245 mg of 2-(4-cyano-benzoyl)-1,2,3,4-tetrahydro-9H-pyrido[3,4-b]indole with m.p. 228–232° C.

2.) 2-(4-Cyano-benzoyl)-9-(3-cyano-benzyl)-1,2,3,4-tetrahydro-9H-pyrido[3,4-b]indole 150 mg (0.5 mmol) of 2-(4-cyano-benzoyl)-1,2,3,4-tetrahydro-9H-pyrido[3,4-b]indole were dissolved in 5 ml of dimethylformamide. 60 mg of potassium tert-butoxide were added and the mixture was stirred for 5 minutes, treated with 100 mg of 3-cyano-benzyl bromide and slowly heated up to 80° C. The mixture was acidified by addition of acetic acid and evaporated under reduced pressure. The residue was partitioned between methylene chloride and 10% aqueous sodium carbonate solution, dried and evaporated. Chromatography of the residue over 12 g of silica gel using 10% (v/v) of ethyl acetate in methylene chloride and crystallization from ethyl acetate/hexane yielded 132 mg of 2-(4-cyano-benzoyl)-9-(3-cyano-benzyl)-1,2,3,4-tetrahydro-9H-pyrido[3,4-b]indole with m.p. 178–180° C.

3.) 2-(4-Amidino-benzoyl)-9-(3-amidino-benzyl)-1,2,3,4-tetrahydro-9H-pyrido[3,4-b]indole trifluoroacetic acid salt A solution of 120 mg of 2-(4-cyano-benzoyl)-9-(3-cyano-benzyl)-1,2,3,4-tetrahydro-9H-pyrido[3,4-b]indole in 5 ml of pyridine and 2.5 ml of triethylamine was saturated with hydrogen sulfide and stirred in a sealed vial at room temperature over night. The solvents were evaporated and at the end co-evaporated azeotropically with toluene. The residue was stirred and the solids were collected and dried. The bis-thioamide obtained was combined with 10 ml of acetone and 0.4 ml of methyl iodide. The mixture was stirred over night in a sealed vial and then diluted with ether. The precipitated solids were separated, dried and dissolved in 15 ml of methanol. After addition of 0.5 g of ammonium acetate and 0.25 ml of acetic acid the mixture was stirred at 55° C. for 3 hours. The solvent was evaporated and the residue was lyophilized from acetonitrile/water containing 0.1% trifluoroacetic acid. Purification by HPLC yielded the title compound with a retention time of 18.2 minutes and the correct molecular weight of 450.2 (MS).

Analogously to the above-described compounds the following example compounds of the formula Ib were prepared which are listed in Table 2. Unless indicated otherwise in Table 2 the compounds of examples 85 to 165 were obtained as trifluoroacetic acid salts.

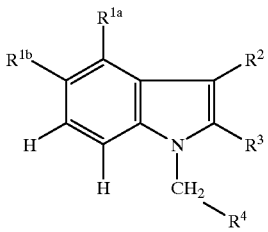

Ib

TABLE 2

Example compounds of the formula Ib

| Example no. | —$R^{1a}$ | —$R^{1b}$ | —$R^2$ | —$R^3$ | —$R^4$ | M.p. (° C.) | (a) |
|---|---|---|---|---|---|---|---|
| 85 | —H | —H | —H | (guanidino-acetamide side chain with HN=C(NH$_2$)NH-, and acetyl-NH-CH-C(O)NH$_2$) | 4-aminobenzyl | nd | c |
| 86 | —H | —H | —H | (guanidino-acetamide side chain with HN=C(NH$_2$)NH-, and acetyl-NH-CH-C(O)NH$_2$) | 4-methylpyridinium-CH$_3$, trifluoroacetate | nd | c |
| 87 | —H | —H | —H | —COOH | 4-amidinobenzyl | nd | c |

TABLE 2-continued
Example compounds of the formula Ib
| Example no. | —R¹ᵃ | —R¹ᵇ | —R² | —R³ | —R⁴ | M.p. (° C.) | (a) |
|---|---|---|---|---|---|---|---|
| 88 | —OH | —H | —H | 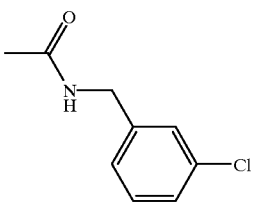 | 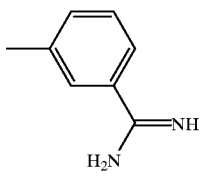 | 216 | s |
| 89 | —H | —H | —H | 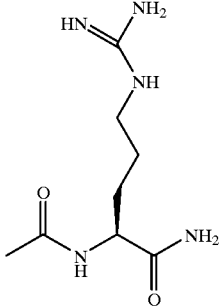 | 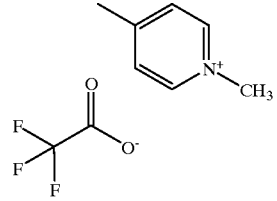 | nd | c |
| 90 | —H | —H | —H | 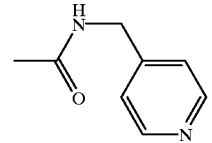 | 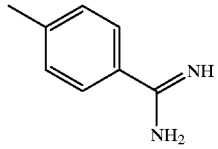 | nd | c |
| 91 | —H | —H | —H | 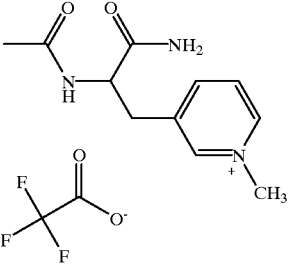 | 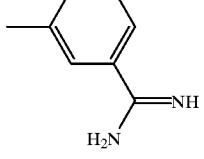 | nd | c |
| 92 | —H | —H | —H | 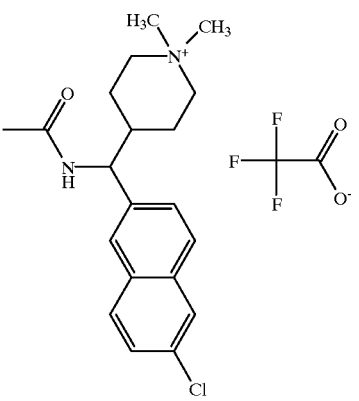 | 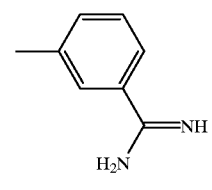 | 140–150 | c |

TABLE 2-continued

Example compounds of the formula Ib

| Example no. | —R¹ᵃ | —R¹ᵇ | —R² | —R³ | —R⁴ | M.p. (° C.) | (a) |
|---|---|---|---|---|---|---|---|
| 93 | —H | —H | —H | 3-(acetamidomethyl)benzamidine | 3-methylbenzamidine | 104 | c |
| 94 (b) | —H | —H | —H | 3-(acetamidomethyl)benzamidine | 3-methylbenzamidine | 106 | c |
| 95 | —H | —OH | —H | —COOH | 3-methylbenzamidine | 119 | c |
| 96 | —OH | —H | —H | N-(2,4-dichlorophenethyl)acetamide | 3-methylbenzamidine | 144 | s |
| 97 | —OH | —H | —H | N-(4-chlorophenethyl)acetamide | 3-methylbenzamidine | 163 | s |
| 98 | —OH | —H | —H | N-(naphthalen-1-ylmethyl)acetamide | 3-methylbenzamidine | 130 | s |
| 99 | —OH | —H | —H | N-(4-bromophenethyl)acetamide | 3-methylbenzamidine | 172 | s |

TABLE 2-continued
Example compounds of the formula Ib
| Example no. | —R$^{1a}$ | —R$^{1b}$ | —R$^2$ | —R$^3$ | —R$^4$ | M.p. (° C.) | (a) |
|---|---|---|---|---|---|---|---|
| 100 | —OH | —H | —H | 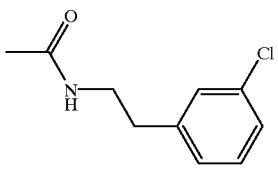 | 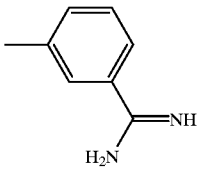 | 196 | s |
| 101 | —CH$_3$ | —H | —H | —CONH$_2$ | 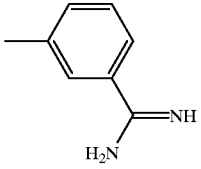 | >250 | c |
| 102 | —OH | —H | —H | 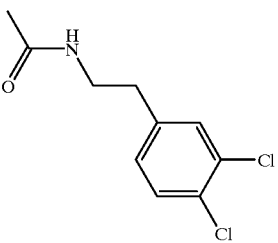 | 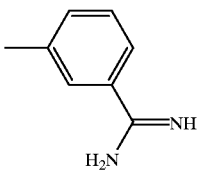 | 200 | s |
| 103 | —OH | —H | —H | 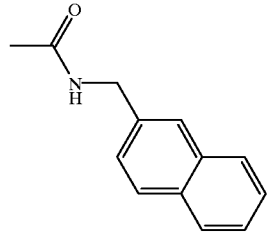 | 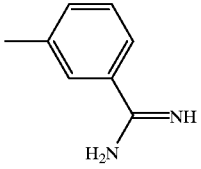 | nd | s |
| 104 | —OH | —H | —H | 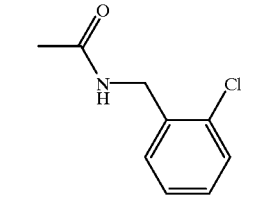 | 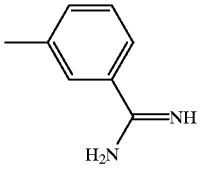 | 264 | s |
| 105 | —OH | —H | —H | —CONH$_2$ | 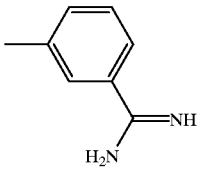 | 123 | s |

TABLE 2-continued

Example compounds of the formula Ib

| Example no. | —R¹ᵃ | —R¹ᵇ | —R² | —R³ | —R⁴ | M.p. (° C.) | (a) |
|---|---|---|---|---|---|---|---|
| 106 | —H | —H | —Cl | 4-(acetamidomethyl)-N,N,N-trimethylanilinium trifluoroacetate | 3-amidinophenyl | 57 | c |
| 107 | —CH₃ | —H | —H | 4-hydroxybenzyl acetamide | 3-amidinophenyl | 120 | c |
| 108 | —CH₃ | —H | —H | naphthalen-1-ylmethyl acetamide | 3-amidinophenyl | 252 | c |
| 109 | —OH | —H | —H | 3,4-dimethoxybenzyl acetamide | 3-amidinophenyl | nd | s |
| 110 | —OH | —H | —H | cyclohexylmethyl acetamide | 3-amidinophenyl | nd | s |

TABLE 2-continued
Example compounds of the formula Ib
| Example no. | —R¹ᵃ | —R¹ᵇ | —R² | —R³ | —R⁴ | M.p. (° C.) | (a) |
|---|---|---|---|---|---|---|---|
| 111 | —OH | —H | —H | 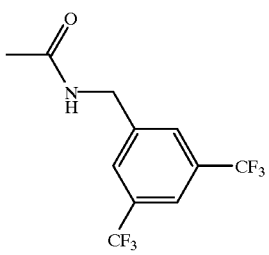 | 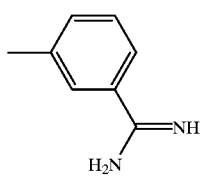 | 122 | s |
| 112 | —OH | —H | —H | 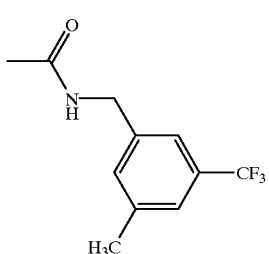 | 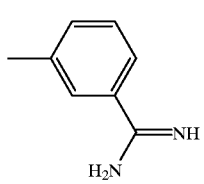 | 126 | s |
| 113 | —H | —H | —Cl | 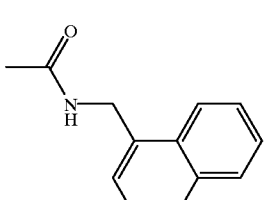 | 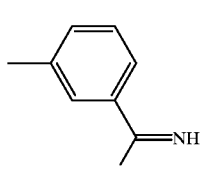 | 252 | c |
| 114 | —CH₃ | —H | —H | 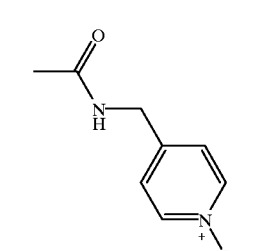 | 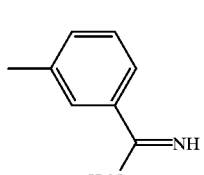 | 113 | c |
| 115 | —H | —H | —Cl | 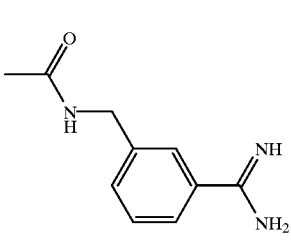 | 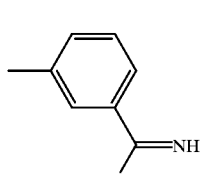 | 227 | c |
| 116 | —CH₃ | —H | —H | 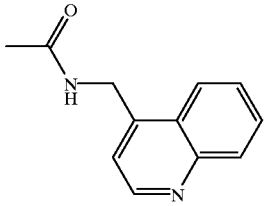 | 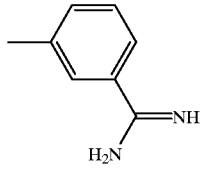 | 100 | c |

TABLE 2-continued

Example compounds of the formula Ib

| Example no. | —R¹ᵃ | —R¹ᵇ | —R² | —R³ | —R⁴ | M.p. (° C.) | (a) |
|---|---|---|---|---|---|---|---|
| 117 | —CH₃ | —H | —H | acetamidomethyl-isoquinoline | 3-methylbenzamidine | 210 | c |
| 118 | —OH | —H | —H | N-(3,5-dimethoxybenzyl)acetamide | 3-methylbenzamidine | nd | s |
| 119 | —OH | —H | —H | N-[4-(trimethylammonio)benzyl]acetamide I⁻ | 3-methyl-N'-hydroxybenzamidine | nd | s |
| 120 | —OH | —H | —H | N-(3,5-dichlorobenzyl)acetamide | 3-methylbenzamidine | 117 | s |
| 121 | —OH | —H | —H | N-(3-methylbenzyl)acetamide | 3-methylbenzamidine | 184 | s |
| 122 | —OH | —H | —H | N-(3-trifluoromethylbenzyl)acetamide | 3-methylbenzamidine | 89 | s |

TABLE 2-continued

Example compounds of the formula Ib

| Example no. | —R¹ᵃ | —R¹ᵇ | —R² | —R³ | —R⁴ | M.p. (° C.) | (a) |
|---|---|---|---|---|---|---|---|
| 123 | —H | —H | —Br | 3-(acetamidomethyl)benzamidine | 3-methylbenzamidine | 166 | c |
| 124 | —CH₃ | —H | —H | N-(3,5-dichlorobenzyl)acetamide | 3-methylbenzamidine | 220 | c |
| 125 | —CH₃ | —H | —H | N-(3,5-dimethylbenzyl)acetamide | 3-methylbenzamidine | 236 | c |
| 126 | —OH | —H | —H | N-(isoquinolin-1-ylmethyl)acetamide | 3-methylbenzamidine | 117 | s |
| 127 | —CH₃ | —H | —Br | 3-(acetamidomethyl)benzamidine | 3-methylbenzamidine | 260 | c |
| 128 | —OH | —H | —H | N-(3,5-difluorobenzyl)acetamide | 3-methylbenzamidine | 107 | s |

TABLE 2-continued
Example compounds of the formula Ib
| Example no. | —R$^{1a}$ | —R$^{1b}$ | —R$^2$ | —R$^3$ | —R$^4$ | M.p. (° C.) | (a) |
|---|---|---|---|---|---|---|---|
| 129 | —OH | —H | —H | 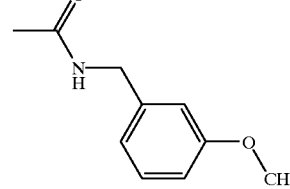 | 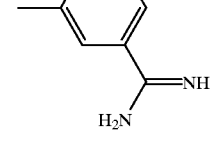 | 75 | s |
| 130 | —OH | —H | —H | 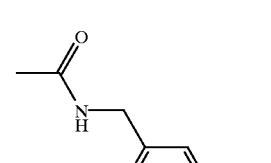 | 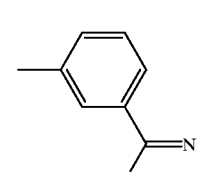 | 82 | s |
| 131 | —OH | —H | —H | 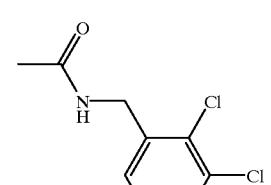 | 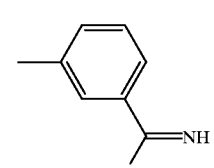 | 109 | s |
| 132 | —OH | —H | —H | 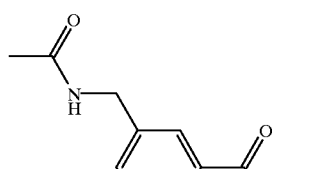 | 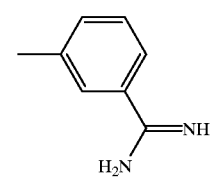 | 95 | s |
| 133 | —OH | —H | —H | 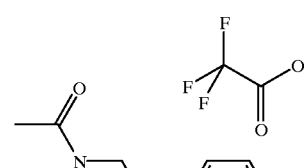 | 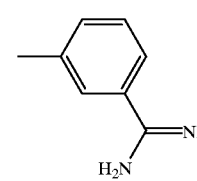 | nd | s |
| 134 | —OH | —H | —H | 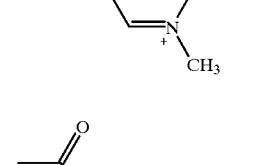 | 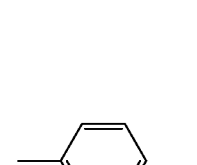 | nd | s |

TABLE 2-continued

Example compounds of the formula Ib

| Example no. | —R¹ᵃ | —R¹ᵇ | —R² | —R³ | —R⁴ | M.p. (° C.) | (a) |
|---|---|---|---|---|---|---|---|
| 135 (c) | —OH | —H | —H | 3-(acetamidomethyl)benzoic acid group | 3-amidinophenyl | 230 | c |
| 136 | —OH | —H | —H | S-methyl thioacetate group | 3-amidinophenyl | nd | s |
| 137 | —OH | —H | —H | N-(3,5-dimethylbenzyl)acetamide group | 3-amidinophenyl | nd | s |
| 138 | —OH | —H | —H | N-(3-fluoro-5-trifluoromethylbenzyl)acetamide group | 3-amidinophenyl | nd | s |
| 139 | —OH | —H | —H | N-benzylacetamide group | 3-amidinophenyl | 197 | s |
| 140 | —OH | —H | —H | N-(2,3,5-trichlorobenzyl)acetamide group | 3-amidinophenyl | 90 | s |

TABLE 2-continued
Example compounds of the formula Ib
| Example no. | —R$^{1a}$ | —R$^{1b}$ | —R$^2$ | —R$^3$ | —R$^4$ | M.p. (° C.) | (a) |
|---|---|---|---|---|---|---|---|
| 141 | —OH | —H | —H | 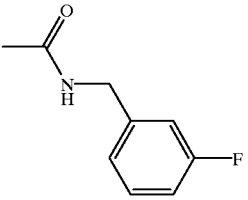 | 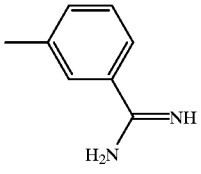 | 200 | s |
| 142 (c) | —OH | —H | —H | 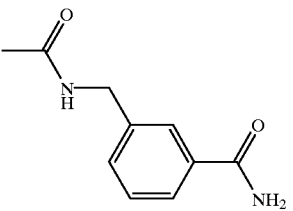 | 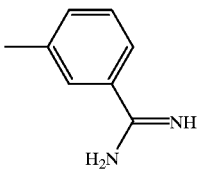 | 207 | s |
| 143 | —OH | —H | —H | 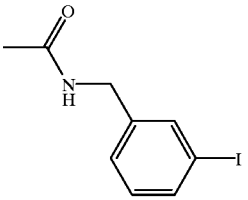 | 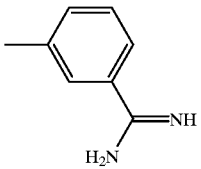 | 210 | s |
| 144 | —CH$_3$ | —H | —H | 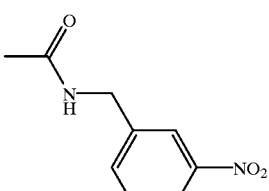 | 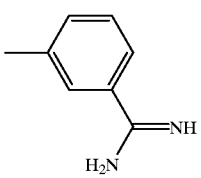 | 249 | c |
| 145 | —H | —H | —Br | 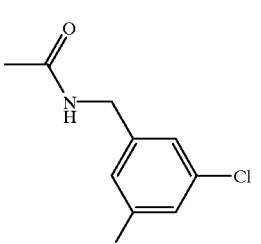 | 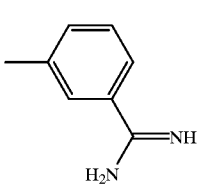 | 236 | c |
| 146 | —H | —H | —Br | 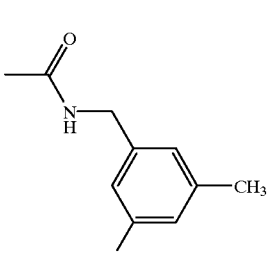 | 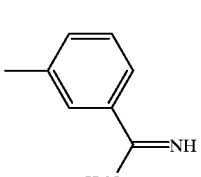 | 224 | c |

TABLE 2-continued

Example compounds of the formula Ib

| Example no. | —R¹ᵃ | —R¹ᵇ | —R² | —R³ | —R⁴ | M.p. (° C.) | (a) |
|---|---|---|---|---|---|---|---|
| 147 | —OH | —H | —H | 3,5-dichlorophenyl-NHC(O)CH₂— | 3-(amidino)phenyl- | 227 | s |
| 148 | —CH₃ | —H | —H | 3-(pyridin-yl)phenyl-CH₂NHC(O)CH₂— | 3-(amidino)phenyl- | 201 | c |
| 149 | —OH | —H | —H | (pyridin-2-yl)CH₂NHC(O)CH₂— | 3-(amidino)phenyl- | nd | s |
| 150 | —CH₃ | —H | (e) | —H | 3-cyanophenyl- | 103 | c |
| 151 (c) | —H | benzyloxymethyl | —H | 4-(N,N-dimethylamino)phenyl-CH₂NHC(O)CH₂— | 3-cyanophenyl- | 166 | c |
| 152 (c) | —OCH₃ | —H | —H | 2-(pyridin-4-yl)ethyl-NHC(O)CH₂— | 3-(thioamido)phenyl- | 170 | c |
| 153 (d) | —OCH₃ | —H | —H | 2-(pyridin-4-yl)ethyl-NHC(O)CH₂— | 3-(thioamido)phenyl- | 160 | c |

TABLE 2-continued

Example compounds of the formula Ib

| Example no. | —R¹ᵃ | —R¹ᵇ | —R² | —R³ | —R⁴ | M.p. (° C.) | (a) |
|---|---|---|---|---|---|---|---|
| 154 (c) | —H | benzyloxymethyl (PhCH₂O-CH₂-) | —H | acetamido-CH₂-C₆H₄-N(CH₃)₂ | 3-methyl-thiobenzamide | 169 | c |
| 155 (c) | —H | benzyloxymethyl | —H | acetamido-CH₂-C₆H₄-N⁺(CH₃)₃ I⁻ | 3-methyl-benzonitrile | 87 | c |
| 156 (c) | —H | —H | —H | acetamido-CH₂-(4-Cl-C₆H₄) | 4-methyl-thiobenzamide | 191 | c |
| 157 (c) | —H | —H | —H | acetamido-CH₂-C₆H₅ | 4-methyl-thiobenzamide | 196 | c |
| 158 (d) | —H | —NH₂ | —H | acetamido-CH₂-C₆H₄-N(CH₃)₂ | 3-methyl-thiobenzamide | 170 | c |

TABLE 2-continued

Example compounds of the formula Ib

| Example no. | —R¹ᵃ | —R¹ᵇ | —R² | —R³ | —R⁴ | M.p. (° C.) | (a) |
|---|---|---|---|---|---|---|---|
| 159 (c) | —OCH₃ | —H | —H | (acetamidomethyl-N-methylpyridinium acetate) | 3-cyanophenyl | 128 | c |
| 160 (c) | —H | —H | —H | (α-phenyl-α-(4-pyridyl)methyl acetamide) | 4-cyanophenyl | 237 | c |
| 161 | —OH | —H | —H | (N-(2-naphthyl)glycinamide acetyl) | 3-amidinophenyl | 233 | s |
| 162 | —OH | —H | —H | (N-methyl-N-(1-naphthyl)ethylenediamine acetyl) | 3-amidinophenyl | 166 | s |
| 163 | —OH | —H | —H | (N-(1-naphthyl)ethylenediamine acetyl) | 3-amidinophenyl | 128 | s |

TABLE 2-continued

Example compounds of the formula Ib

| Example no. | —R$^{1a}$ | —R$^{1b}$ | —R$^2$ | —R$^3$ | —R$^4$ | M.p. (° C.) | (a) |
|---|---|---|---|---|---|---|---|
| 164 | —OH | —H | —H | 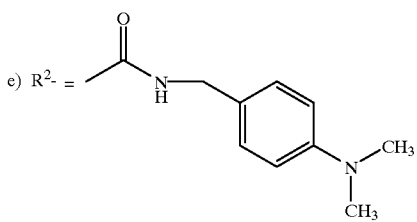 | 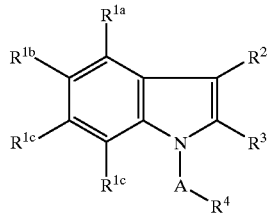 | 177 | s |
| 165 | —OH | —H | —H | (adamantylmethyl acetamide structure) | (m-tolyl amidine structure) | 165 | s | e) R$^2$- = (4-dimethylaminobenzyl acetamide structure)

Analogously to the above-described compounds also the compound of example 166 was prepared.

Example 166

1-{3-4-(Amidino)phenyl]-2-propynyl}-N-[(4-pyridyl)methyl]-1H-indole-2-carboxamide trifluoroacetic acid salt

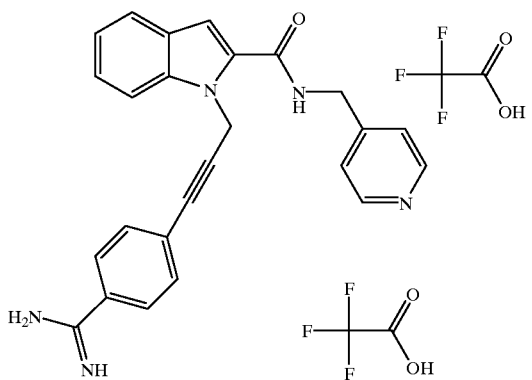

The disclosure of all publications mentioned above is expressly incorporated herein by reference in their entireties to the same extent as if each publication were incorporated by reference individually.

What is claimed is:

1. Compounds of the formula I,

I (indole structure with R$^{1a}$, R$^{1b}$, R$^{1c}$, R$^{1d}$, R$^2$, R$^3$, A, R$^4$)

wherein two of the residues R$^{1a}$, R$^{1b}$, R$^{1c}$ and R$^{1d}$ independent of one another are hydrogen, F, Cl, Br, I, (C$_1$–C$_4$)-alkyl, CF$_3$, phenyl, phenyl-(C$_1$–C$_4$)-alkyl-, (C$_1$–C$_4$)-alkoxy, phenyloxy-, phenyl-(C$_1$–C$_4$)-alkoxy-, OH, NO$_2$, —NR$^{5a}$R$^{5b}$, —NR$^{5b}$—SO$_2$—R$^{6a}$, —S—R$^{6b}$, —SO$_n$—R$^{6c}$ where n is 1 or 2, —SO$_2$—NR$^{5a}$R$^{5b}$, —CN or —CO—R$^7$, and are identical or different, and the other two of the residues R$^{1a}$, R$^{1b}$, R$^{1c}$ and R$^{1d}$ are hydrogen;

R$^{5a}$ is hydrogen, (C$_1$–C$_4$)-alkyl, phenyl, phenyl-(C$_1$–C$_4$)-alkyl-, formyl, ((C$_1$–C$_4$)-alkyl)carbonyl-, phenylcarbonyl-, phenyl-((C$_1$–C$_4$)-alkyl)carbonyl-, ((C$_1$–C$_4$)-alkoxy)carbonyl- or phenyl-((C$_1$–C$_4$)-alkoxy)carbonyl-;

R$^{5b}$ is hydrogen, (C$_1$–C$_4$)-alkyl, phenyl or phenyl-(C$_1$–C$_4$)-alkyl-;

R$^{6a}$ is (C$_1$–C$_4$)-alkyl, phenyl, phenyl-(C$_1$–C$_4$)-alkyl- or phenyl-NH—;

R$^{6b}$ is (C$_1$–C$_4$)-alkyl, phenyl or phenyl-(C$_1$–C$_4$)-alkyl-;

R$^{6c}$ is hydroxy, (C$_1$–C$_4$)-alkyl, phenyl or phenyl-(C$_1$–C$_4$)-alkyl-;

$R^7$ is hydroxy, $(C_1-C_4)$-alkoxy, phenyl-$(C_1-C_4)$-alkoxy- or —$NR^{5a}R^{5b}$;

where all residues $R^{5a}$, $R^{5b}$, $R^{6a}$, $R^{6b}$, $R^{6c}$ and $R^7$ if present more than one time in the molecule, are independent of one another and can each be identical or different;

and where phenyl present in the residues $R^{1a}$, $R^{1b}$, $R^{1c}$, $R^{1d}$, $R^{5a}$, $R^{5b}$, $R^{6a}$, $R^{6b}$, $R^{6c}$ and $R^7$ denotes an unsubstituted phenyl residue or a phenyl residue which is substituted by one or two identical or different substituents selected from the series consisting of $(C_1-C_4)$-alkyl, F, Cl, Br, $CF_3$, $(C_1-C_4)$-alkoxy, $NO_2$, OH, $NH_2$ and CN;

one of the residues $R^2$ and $R^3$ is —$(CH_2)_p$—CO—$R^8$ and the other is hydrogen, F, Cl, Br, $(C_1-C_4)$-alkyl or —$(CH_2)_p$—CO—$R^8$, or $R^2$ and $R^3$ together form a group of the formula —$CH_2$—$CH_2$—N(—CO—$R^{20}$)—$CH_2$— wherein $R^{20}$ is phenyl, phenyl-$(C_1-C_4)$-alkyl-, pyridyl or pyridyl-$(C_1-C_4)$-alkyl- and where each phenyl residue is unsubstituted or substituted by $R^{15a}$ and each pyridyl residue is unsubstituted or substituted at the nitrogen atom by $R^{14}$;

p is 0, 1 or 2;

$R^8$ is —$NR^9R^{10}$, —$OR^{10}$ or —S—$(C_1-C_4)$-alkyl, where residues $R^8$ if present more than one time in the molecule, are independent of each other and can be identical or different;

$R^9$ is hydrogen, $(C_1-C_4)$-alkyl-, hydroxycarbonyl-$(C_1-C_4)$-alkyl-, $((C_1-C_4)$-alkoxy)carbonyl-$(C_1-C_4)$-alkyl- or aminocarbonyl-$(C_1-C_4)$-alkyl-;

$R^{10}$ is hydrogen, $(C_1-C_{10})$-alkyl-, phenyl, naphthyl, phenyl-$(C_1-C_4)$-alkyl-, naphthyl-$(C_1-C_4)$-alkyl-, pyridyl or the residue Het, where the $(C_1-C_{10})$-alkyl-residue and each phenyl and naphthyl residue is unsubstituted or substituted by one, two or three identical or different residues $R^{11}$, and where the pyridyl residue is unsubstituted or substituted at the nitrogen atom by $R^{14}$, and where Het is unsubstituted or substituted by $R^{15a}$;

or $R^9$ and $R^{10}$ together with the nitrogen atom to which they are bonded form a 5-membered or 6-membered saturated heterocyclic ring which can contain an additional nitrogen atom in the ring and which is unsubstituted or substituted by $R^{15a}$ or by —CO—$R^7$;

Het is the residue of a 5-membered or 6-membered saturated heterocyclic ring containing 1 or 2 identical or different ring heteroatoms selected from the series consisting of nitrogen, oxygen and sulfur;

$R^{11}$ is —$N(R^{12})_2$, —$OR^{12}$, —CO—$N(R^{13})_2$, —CO—$R^7$, $R^{15b}$, $(C_1-C_{14})$-alkyl, phenyl which is unsubstituted or substituted by one, two or three identical or different residues $R^{15b}$, naphthyl which is unsubstituted or substituted by one, two or three identical or different residues $R^{15b}$, quinolinyl which is unsubstituted or substituted by one, two or three identical or different residues $R^{15b}$ and/or substituted at the nitrogen atom by $R^{14}$, isoquinolinyl which is unsubstituted or substituted by one, two or three identical or different residues $R^{15b}$ and/or substituted at the nitrogen atom by $R^{14}$, pyridyl which is unsubstituted or substituted at the nitrogen atom by $R^{14}$, or Het which is unsubstituted or substituted by $R^{15a}$, where residues $R^{11}$ if present more than one time in the molecule, are independent of each other and can be identical or different;

each residue $R^{12}$ independent of the denotation of another residue $R^{12}$ is hydrogen, $(C_1-C_4)$-alkyl, phenyl, phenyl-$(C_1-C_4)$-alkyl-, naphthyl, naphthyl-$C_1-C_4)$-alkyl-, pyrrolidinyl, piperidinyl, pyrrolidinyl-$(C_1-C_4)$-alkyl- or piperidinyl-$(C_1-C_4)$-alkyl-, where each pyrrolidinyl residue and each piperidinyl residue is unsubstituted or substituted at the nitrogen atom by phenyl-$(C_1-C_4)$-alkyl- or $R^{15a}$;

each residue $R^{13}$ independent of the denotation of another residue $R^{13}$ is hydrogen, $(C_1-C_4)$-alkyl, phenyl, phenyl-$(C_1-C_4)$-alkyl-, naphthyl or naphthyl-$(C_1-C_4)$-alkyl-, or the two residues $R^{13}$ together with the nitrogen atom to which they are bonded form a 5-membered or 6-membered saturated heterocyclic ring which can contain an additional nitrogen atom or oxygen atom in the ring where the additional nitrogen atom in the ring is unsubstituted or substituted by $(C_1-C_4)$-alkyl or phenyl-$(C_1-C_4)$-alkyl-;

$R^{14}$ is $(C_1-C_6)$-alkyl, $(C_1-C_6)$-alkenyl, $(C_1-C_6)$-alkynyl, phenyl-$(C_1-C_6)$-alkyl- or $((C_1-C_6)$-alkoxy)carbonyl-$(C_1-C_5)$-alkyl-, where phenyl present in $R^{14}$ denotes an unsubstituted phenyl residue, the substitution by these residues at the nitrogen atom of the heterocyclic residue leading to a positively charged group having $X^-$ as the counterion; or $R^{14}$ is oxido this substitution at the nitrogen atom of the heterocyclic residue leading to an N-oxide; and where residues $R^{14}$ if present more than one time in the molecule, are independent of each other and can be identical or different;

$R^{15a}$ is $(C_1-C_6)$-alkyl, $((C_1-C_6)$-alkyl$)$-C(=NH)—, —$(CH_2)_t$—$N(R^{16})_2$, —$(CH_2)_t$—$N^+(R^{16a})_2(—O^-)$, —$(CH_2)_t$—$N^+(R^{16a})_3X^-$, —$(CH_2)_t$—$NHR^{17}$, —$(CH_2)_t$—CN, —$(CH_2)_t$—CS—$N(R^{18})_2$, —$(CH_2)_t$—$C(=NR^{17})$—$NHR^{17}$ or —$(CH_2)_t$—NH—$C(=NR^{17})$—$NHR^{17}$, where $((C^1-C_6)$-alkyl$)$-C(=NH)— is bonded to a ring nitrogen atom, and where residues $R^{15a}$ if present more than one time in the molecule, are independent of each other and can be identical or different;

$R^{15b}$ is $(C_1-C_6)$-alkyl, hydroxy, $(C_1-C_4)$-alkoxy, F, Cl, Br, I, $NO_2$, —$(CH_2)_t$—$N(R^{16})_2$, —$(CH_2)_t$—$N^+(R^{16a})_2(—O^-)$, —$(CH_2)_t$—$N^+(R^{16a})_3X^-$, —$(CH_2)_t$—$NHR^{17}$, —$(CH_2)_t$—CO—$OR^{18}$, —$(CH_2)_t$—CO—$N(R^{18})_2$, —$(CH_2)_t$—CN, —$(CH_2)_t$—CS—$N(R^{18})_2$, —$(CH_2)_t$—$C(=NR^{17})$—$NHR^{17}$ or —$(CH_2)_t$—NH—$C(=NR^{17})$—$NHR^{17}$, where alkyl can be substituted 1, 2, 3, 4, 5, 6, or 7 times by fluoro, and where residues $R^{15b}$ if present more than one time in the molecule, are independent of each other and can be identical or different;

t is 0, 1, 2 or 3, where numbers t, if present more than one time in the molecule, are independent of each other and can be identical or different;

each residue $R^{16}$ independent of the denotations of another residue $R^{16}$ is hydrogen, $(C_1-C_6)$-alkyl, $(C_1-C_6)$-alkenyl, $(C_1-C_6)$-alkynyl, phenyl-$(C_1-C_6)$-alkyl- or $((C_1-C_6)$-alkoxy)carbonyl-$(C_1-C_6)$-alkyl-, where phenyl present in $R^{16}$ denotes an unsubstituted phenyl residue, and where groups containing residues $R^{16}$ if present more than one time in the molecule, are independent of each other and can be identical or different;

each residue $R^{16a}$ independent of the denotations of another residue $R^{16a}$ is $(C_1-C_6)$-alkyl, $(C_1-C_6)$-alkenyl, $(C_1-C_6)$-alkynyl, phenyl-$(C_1-C_6)$-alkyl- or $((C_1-C_6)$-alkoxy)carbonyl-$(C_1-C_6)$-alkyl-, where phenyl present in $R^{16a}$ denotes an unsubstituted phenyl residue, and where groups containing residues $R^{16a}$ if present more than one time in the molecule, are independent of each other and can be identical or different;

each residue $R^{17}$ independent of the denotation of another residue $R^{17}$ is hydrogen, $(C_1-C_6)$-alkyl, $(C_1-C_6)$-alkylcarbonyl-, $(C_1-C_6)$-alkoxycarbonyl-, $(C_1-C_6)$-alkylcarbonyloxy-$(C_1-C_6)$-alkoxycarbonyl-, phenylcarbonyl-, phenoxycarbonyl-, phenyl-$(C_1-C_6)$-alkoxycarbonyl-, hydroxy, $(C_1-C_6)$-alkoxy, phenyl-$(C_1-C_6)$-alkoxy- or amino, and additionally in the groups —$(CH_2)_t$—$C(=NR^{17})$—$NHR^{17}$ and —$(CH_2)_t$—NH—$C(=NR^{17})$—$NHR^{17}$ the two residues $R^{17}$ together with the $C(=N)$—NH group to which they are bonded, can form a 5-membered or 6-membered heterocyclic ring, and where phenyl present in $R^{17}$ denotes an unsubstituted phenyl residue, and where groups containing residues $R^{17}$ if present more than one time in the molecule, are independent of each other and can be identical or different;

each residue $R^{18}$ independent of the denotation of another residue $R^{18}$ is hydrogen or $(C_1-C_4)$-alkyl;

A is a direct linkage, a divalent —$(C_1-C_4)$-alkyl- residue which is saturated or which contains a double bond or a triple bond, —CO—, —$SO_r$— wherein r is 1 or 2, —CO—$(C_1-C_4)$-alkyl-, —$(C_1-C_4)$-alkyl-CO— or —$(C_1-C_4)$-alkyl-CO—NH— wherein the nitrogen is bonded to $R^4$;

$R^4$ is phenyl which is substituted by one residue $R^{15c}$ and which can additionally be substituted by one or two substituents from the series consisting of $(C_1-C_4)$-alkyl, F, Cl and Br, or $R^4$ is pyridyl which is unsubstituted or substituted at the nitrogen atom by $R^{14}$, or $R^4$ is the residue Het which is substituted by $R^{15d}$;

$R^{15c}$ is —$(CH_2)_t$—$N(R^{16})_2$, —$(CH_2)_t$—$N^+(R^{16a})_2(-O^-)$, —$(CH_2)_t$—$N^+(R^{16a})_3X^-$, —$(CH_2)_t$—$NHR^{17}$, —$(CH_2)_t$—CN, —$(CH_2)_t$—CS—$N(R_{18})_2$, —$(CH_2)_t$—$C(=NR^{17})$—$NHR^{17}$ or —$(CH_2)_t$—NH—$C(=NR^{17})$—$NHR^{17}$;

$R^{15d}$ is $((C_1-C_6)$-alkyl$)$-$C(=NH)$—, —$(CH_2)_t$—$N(R^{16})_2$, —$(CH_2)_t$—$N^+(R^{16a})_2(-O^-)$, —$(CH_2)_t$—$N^+(R^{16a})_3X^-$, —$(CH_2)_t$—$NHR^{17}$, —$(CH_2)_t$—CN, —$(CH_2)_t$—CS—$N(R^{18})_2$, —$(CH_2)_t$—$C(=NR^{17})$—$NHR^{17}$ or —$(CH_2)_t$—NH—$C(=NR^{17})$—$NHR^{17}$, where $((C_1-C_6)$-alkyl$)$-$C(=NH)$— is bonded to a ring nitrogen atom;

$X^-$ is a physiologically acceptable anion;

in all their stereoisomeric forms and mixtures thereof in any ratio, and their physiologically acceptable salts.

2. Compounds of the formula I as claimed in claim 1, wherein A is a divalent —$(C_1-C_4)$-alkyl- residue, in all their stereoisomeric forms and mixtures thereof in any ratio, and their physiologically acceptable salts.

3. Compounds of the formula I as claimed in claim 1, wherein $R^4$ is phenyl substituted by one residue $R^{15c}$, in all their stereoisomeric forms and mixtures thereof in any ratio, and their physiologically acceptable salts.

4. Compounds of the formula I as claimed in claim 1, wherein $R^{15c}$ is —$(CH_2)_t$—$C(=NR^{17})$—$NHR^{17}$, in all their stereoisomeric forms and mixtures thereof in any ratio, and their physiologically acceptable salts.

5. Compounds of the formula I as claimed in claim 1, wherein A is a methylene residue —$CH_2$—, and $R^4$ is phenyl which is substituted by —$C(=NR^{17})$—$NHR^{17}$ in the meta position, in all their stereoisomeric forms and mixtures thereof in any ratio, and their physiologically acceptable salts.

6. Compounds of the formula I as claimed in claim 1, wherein $R^3$ is —CO—$R^8$, in all their stereoisomeric forms and mixtures thereof in any ratio, and their physiologically acceptable salts.

7. Compounds of the formula I as claimed in claim 1, wherein $R^2$ is hydrogen, Cl, or Br, in all their stereoisomeric forms and mixtures thereof in any ratio, and their physiologically acceptable salts.

8. Compounds of the formula I as claimed in claim 1, wherein the residues $R^{1c}$ and $R^{1d}$ are hydrogen, in all their stereoisomeric forms and mixtures thereof in any ratio, and their physiologically acceptable salts.

9. Compounds of the formula I as claimed in claim 1, wherein one of the residues $R^{1a}$ and $R^{1b}$ is hydrogen and the other is selected from hydrogen, methyl, F, Cl, Br, I, hydroxy, $(C_1-C_4)$-alkoxy, phenyl-$(C_1-C_4)$-alkoxy-, and —$NHR^{5a}$, in all their stereoisomeric forms and mixtures thereof in any ratio, and their physiologically acceptable salts.

10. A process of preparing compounds of the formula I as claimed in claim 1, comprising condensing a compound of the formula VII with a compound of the formula $HR^{8'}$ to give a compound of the formula VIII, and optionally converting the compound of the formula VIII into a compound of the formula I,

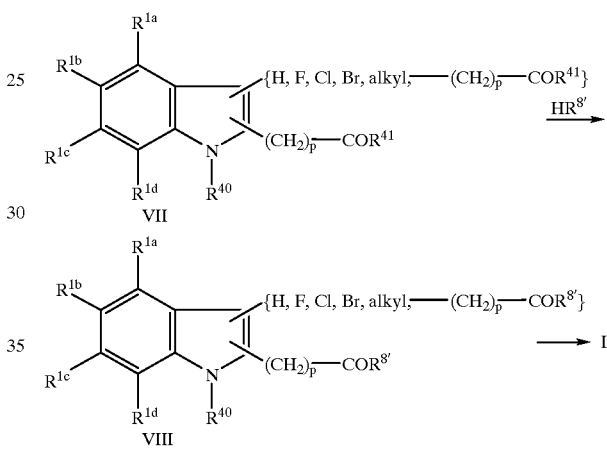

where the residues $R^{8'}$, which are identical or different, are optionally the same as $R^8$ indicated in claim 1, but where in $R^{8'}$ functional groups are optionally groups that are subsequently transformed into the final functional groups present in $R^8$, and where the residue $R^{40}$ optionally denotes the group —A—$R^4$ or optionally denotes a group which is subsequently transformed into the group —A—$R^4$, and where the groups —$COR^{41}$ which are identical or different, can be carboxylic acid groups or derivatives thereof, and where the groups $R^{1a}$, $R^{1b}$, $R^{1c}$ and $R^{1d}$ are defined as in claim 1 or functional groups in $R^{1a}$, $R^{1b}$, $R^{1c}$ and $R^{1d}$ are optionally present in protected form or in the form of precursor groups.

11. A pharmaceutical composition, comprising at least one compound of the formula I as claimed in any one of claims 1 to 9 or their physiologically acceptable salts together with a pharmaceutically acceptable carrier.

12. A pharmaceutical, comprising at least one compound of the formula I as claimed in any one of claims 1 to 9 or its physiologically acceptable salts.

13. A method for inhibiting factor Xa, comprising combining at least one compound of the formula I as claimed in claim 1 or its physiologically acceptable salts with factor Xa.

14. A method for inhibiting blood clotting, comprising combining at least one compound of the formula I as claimed in claim 1 or its physiologically acceptable salts with blood.

15. A method for treating or preventing cardiovascular disorders or thromboembolic conditions, comprising administering to a patient in need thereof an effective amount of at least one compound of the formula I as claimed in claim 1 or its physiologically acceptable salts.

16. A method for treating or preventing thromboses, cardiac infarction, angina pectoris, restenoses, or reocclusion, comprising administering to a patient in need thereof an effective amount of at least one compound of the formula I as claimed in any one of claims 1 to 9 or its physiologically acceptable salts.

* * * * *